(12) United States Patent
Rothberg et al.

(10) Patent No.: US 11,538,556 B2
(45) Date of Patent: Dec. 27, 2022

(54) MACHINE LEARNING ENABLED PULSE AND BASE CALLING FOR SEQUENCING DEVICES

(71) Applicant: Quantum-Si Incorporated, Guilford, CT (US)

(72) Inventors: Jonathan M. Rothberg, Guilford, CT (US); Michael Meyer, Guilford, CT (US); Umut Eser, North Haven, CT (US)

(73) Assignee: Quantum-Si Incorporated, Guilford, CT (US)

( * ) Notice: Subject to any disclaimer, the term of this patent is extended or adjusted under 35 U.S.C. 154(b) by 1008 days.

(21) Appl. No.: 16/258,299

(22) Filed: Jan. 25, 2019

(65) Prior Publication Data

US 2019/0237160 A1 Aug. 1, 2019

Related U.S. Application Data

(60) Provisional application No. 62/622,754, filed on Jan. 26, 2018.

(51) Int. Cl.
*G01N 33/48* (2006.01)
*G01N 33/50* (2006.01)
(Continued)

(52) U.S. Cl.
CPC ......... *G16B 30/10* (2019.02); *G01N 21/6428* (2013.01); *G06N 3/0472* (2013.01);
(Continued)

(58) Field of Classification Search
CPC ........ G16B 30/10; G16B 40/10; G16B 40/20; G16B 45/00; G01N 21/6428; G06N 3/0472; G06N 20/00; C12Q 1/6874
See application file for complete search history.

(56) References Cited

U.S. PATENT DOCUMENTS 5,961,924 A 10/1999 Reichert et al.
6,787,308 B2 9/2004 Balasubramanian et al.
(Continued)

FOREIGN PATENT DOCUMENTS

CN 1328604 A 12/2001
CN 102482718 A 5/2012
(Continued)

OTHER PUBLICATIONS

Hale, Fibre Optic Sensors using Adiabatically Tapered Single Mode Fibres. Dissertation submitted to the University of Cambridge. Feb. 1994. 209 pages.
(Continued)

*Primary Examiner* — Russell S Negin
(74) *Attorney, Agent, or Firm* — Wolf, Greenfield & Sacks, P.C.

(57) ABSTRACT

A method includes obtaining, from one or more sequencing devices, raw data detected from luminescent labels associated with nucleotides during nucleotide incorporation events; and processing the raw data to perform a comparison of base calls produced by a learning enabled, automatic base calling module of the one or more sequencing devices with actual values associated with the raw data, wherein the base calls identify one or more individual nucleotides from the raw data. Based on the comparison, an update to the learning enabled, automatic base calling module is created using at least some of the obtained raw data, and the update is made available to the one or more sequencing devices.

24 Claims, 34 Drawing Sheets

(51) Int. Cl.

| | | |
|---|---|---|
| *G16B 30/10* | (2019.01) | |
| *G16B 30/20* | (2019.01) | |
| *G06N 20/00* | (2019.01) | |
| *G16B 45/00* | (2019.01) | |
| *G16B 40/10* | (2019.01) | |
| *G16B 40/20* | (2019.01) | |
| *G01N 21/64* | (2006.01) | |
| *G06N 3/04* | (2006.01) | |
| *G16B 40/30* | (2019.01) | |
| *C12Q 1/6869* | (2018.01) | |
| *C12Q 1/6874* | (2018.01) | |

(52) U.S. Cl.
CPC ............ *G06N 20/00* (2019.01); *G16B 30/20* (2019.02); *G16B 40/10* (2019.02); *G16B 40/20* (2019.02); *G16B 45/00* (2019.02); *C12Q 1/6869* (2013.01); *C12Q 1/6874* (2013.01); *G16B 40/30* (2019.02)

(56) References Cited

U.S. PATENT DOCUMENTS

| | | | |
|---|---|---|---|
| 6,917,726 | B2 | 7/2005 | Levene et al. |
| 7,175,811 | B2 | 2/2007 | Bach et al. |
| 7,426,322 | B2 | 9/2008 | Hyde |
| 7,738,086 | B2 | 6/2010 | Shepard et al. |
| 7,820,983 | B2 | 10/2010 | Lundquist et al. |
| 7,834,329 | B2 | 11/2010 | Lundquist et al. |
| 7,838,847 | B2 | 11/2010 | Lundquist et al. |
| 8,053,742 | B2 | 11/2011 | Lundquist et al. |
| 8,207,509 | B2 | 6/2012 | Lundquist et al. |
| 8,274,040 | B2 | 9/2012 | Zhong et al. |
| 8,278,728 | B2 | 10/2012 | Murshid |
| 8,465,699 | B2 | 6/2013 | Fehr et al. |
| 8,471,219 | B2 | 6/2013 | Lundquist et al. |
| 8,471,230 | B2 | 6/2013 | Zhong et al. |
| 8,502,169 | B2 | 8/2013 | Rigneault et al. |
| 8,618,507 | B1 | 12/2013 | Lundquist et al. |
| 9,029,802 | B2 | 5/2015 | Lundquist et al. |
| 9,157,864 | B2 | 10/2015 | Fehr et al. |
| 9,222,123 | B2 | 12/2015 | Zhong et al. |
| 9,222,133 | B2 | 12/2015 | Lundquist et al. |
| 9,223,084 | B2 | 12/2015 | Grot et al. |
| 9,372,308 | B1 | 6/2016 | Saxena et al. |
| 9,587,276 | B2 | 3/2017 | Lundquist et al. |
| 9,606,060 | B2 | 3/2017 | Chen et al. |
| 9,658,161 | B2 | 5/2017 | Saxena et al. |
| 9,666,748 | B2 | 5/2017 | Leobandung |
| 9,719,138 | B2 | 8/2017 | Zhong et al. |
| 9,759,658 | B2 | 9/2017 | Rothberg et al. |
| 9,765,395 | B2 | 9/2017 | Goldsmith |
| 9,885,657 | B2 | 2/2018 | Rothberg et al. |
| 9,946,017 | B2 | 4/2018 | Saxena et al. |
| 10,018,764 | B2 | 7/2018 | Grot et al. |
| 10,048,208 | B2 | 8/2018 | Rothberg et al. |
| 10,068,053 | B2 | 9/2018 | Kermani et al. |
| 10,090,429 | B2 | 10/2018 | Leobandung |
| 10,108,778 | B2 | 10/2018 | Colwell et al. |
| 10,138,515 | B2 | 11/2018 | Fehr et al. |
| 10,185,803 | B2 | 1/2019 | Frey et al. |
| 10,216,895 | B2 | 2/2019 | Liu |
| 10,217,048 | B2 | 2/2019 | Glode et al. |
| 10,280,457 | B2 | 5/2019 | Zhong et al. |
| 10,310,178 | B2 | 6/2019 | Saxena et al. |
| 10,487,356 | B2 | 11/2019 | Lundquist et al. |
| 10,578,788 | B2 | 3/2020 | Grot et al. |
| 10,655,172 | B2 | 5/2020 | Rank et al. |
| 10,711,299 | B2 | 7/2020 | Rothberg et al. |
| 10,724,090 | B2 | 7/2020 | McCaffrey et al. |
| 2002/0182716 | A1 | 12/2002 | Weisbuch et al. |
| 2003/0044781 | A1 | 3/2003 | Korlach et al. |
| 2003/0174992 | A1 | 9/2003 | Levene et al. |
| 2009/0024331 | A1 | 1/2009 | Tomaney et al. |
| 2010/0065726 | A1 | 3/2010 | Zhong et al. |
| 2011/0165652 | A1 | 7/2011 | Hardin et al. |
| 2013/0023423 | A1 | 1/2013 | Kavanagh et al. |
| 2013/0116153 | A1 | 5/2013 | Bowen et al. |
| 2014/0235474 | A1 | 8/2014 | Tang et al. |
| 2015/0299767 | A1 | 10/2015 | Armour et al. |
| 2016/0041095 | A1 | 2/2016 | Rothberg et al. |
| 2016/0084761 | A1 | 3/2016 | Rothberg et al. |
| 2016/0133668 | A1 | 5/2016 | Rothberg et al. |
| 2017/0146479 | A1 | 5/2017 | Levine et al. |
| 2017/0349944 | A1 | 12/2017 | Rothberg et al. |
| 2019/0292590 | A1 | 9/2019 | Zhong et al. |
| 2020/0291467 | A1 | 9/2020 | Rothberg et al. |
| 2022/0065785 | A1 | 3/2022 | Cao et al. |

FOREIGN PATENT DOCUMENTS

| | | |
|---|---|---|
| CN | 102782159 A | 11/2012 |
| JP | H08-506664 A | 7/1996 |
| JP | 2005-512086 A | 4/2005 |
| JP | 2009-080122 A | 4/2009 |
| JP | 2013-025660 A | 2/2013 |
| JP | 2015-521468 A | 7/2015 |
| JP | 2017-531356 A | 10/2017 |
| WO | WO 00/09753 A1 | 2/2000 |
| WO | WO 2005/120204 A2 | 12/2005 |
| WO | WO 2011/153962 A1 | 12/2011 |
| WO | WO 2013/148400 A1 | 10/2013 |
| WO | WO 2014/190230 A1 | 11/2014 |
| WO | WO 2015/074004 A1 | 5/2015 |
| WO | WO 2016/022998 A2 | 2/2016 |

OTHER PUBLICATIONS

Mogensen et al., A Microfluidic Device with an Integrated Waveguide Beam Splitter for Velocity Measurements of Flowing Particles by Fourier Transformation. Analytical Chemistry. Sep. 15, 2003;75(18):4931-4936.

Taitt et al., Evanescent wave fluorescence biosensors. Biosens Bioelectron. Jun. 2005;20(12):2470-87. Epub Dec. 8, 2004.

International Search Report and Written Opinion for International Application No. PCT/US2019/015098 dated Apr. 30, 2019.

Albrecht et al., Deep learning for single-molecule science. Nanotechnology. 2017;28(42):423001.

Baylor et al., TFX: A TensorFlow-Based Production-Scale Machine Learning Platform. Knowledge Discovery and Data Mining. ACM. 2017;1387-95.

Sutskever et al., Sequence to Sequence Learning with Neural Networks. arXiv. 2014;1-9.

Teng et al., Chiron: Translating nanopore raw signal directly into nucleotide sequence using deep learning. BioRxiv. 2017.

Prober et al., A system for rapid DNA sequencing with fluorescent chain-terminating dideoxynucleotides. Science. Oct. 16, 1987;238(4825):336-41.

Sauer et al., New fluorescent dyes in the red region for biodiagnostics. Journal of fluorescence. Sep. 1995;5(3):247-61.

Sauer et al., New fluorescent labels for time-resolved detection of biomolecules. Journal of fluorescence. Sep. 1993;3(3):131-9.

Seeger et al., Biodiagnostics and polymer identification with multiplex dyes. Berichte der Bunsengesellschaft für physikalische Chemie. Dec. 1993;97(12):1542-7.

Smith et al., Fluorescence detection in automated DNA sequence analysis. Nature. Jun. 1986;321(6071):674-9.

International Search Report and Written Opinion for International Application No. PCT/US2017/035420 dated Nov. 6, 2017.

International Preliminary Report on Patentability for International Application No. PCT/US2017/035420 dated Dec. 13, 2018.

Cao et al., A simple statistical algorithm for biological sequence compression. 2007 Data Compression Conference (DCC '07). (IEEE, Utah), pp. 43-52.

Killick et al., Optimal detection of changepoints with a linear computational cost. Journal of the American Statistical Association. 2012;107(500):1590-8. DOI:10.1080/01621459.2012.737745.

Extended European Search Report for European Application No. 21199556.8 dated May 11, 2022.

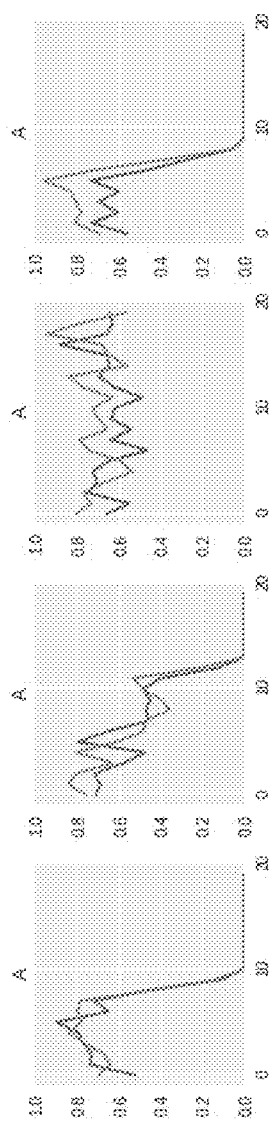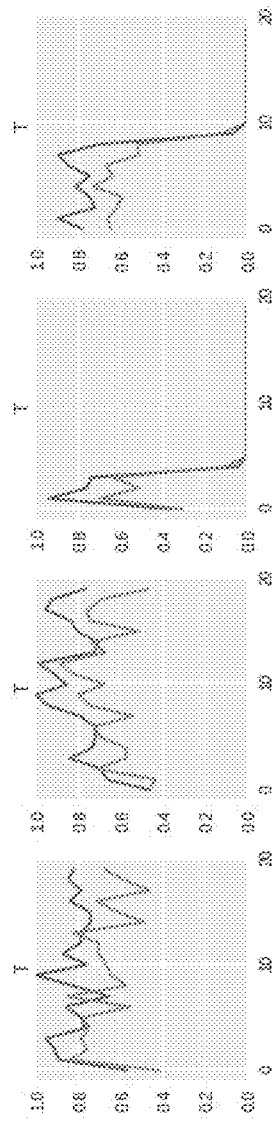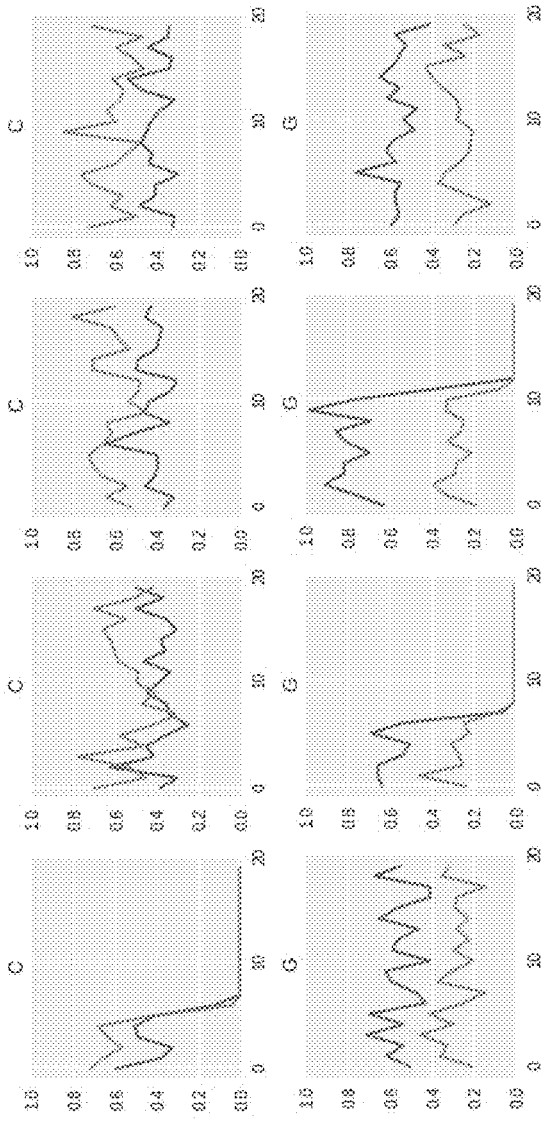
FIG. 16A
FIG. 16B
FIG. 16C
FIG. 16D

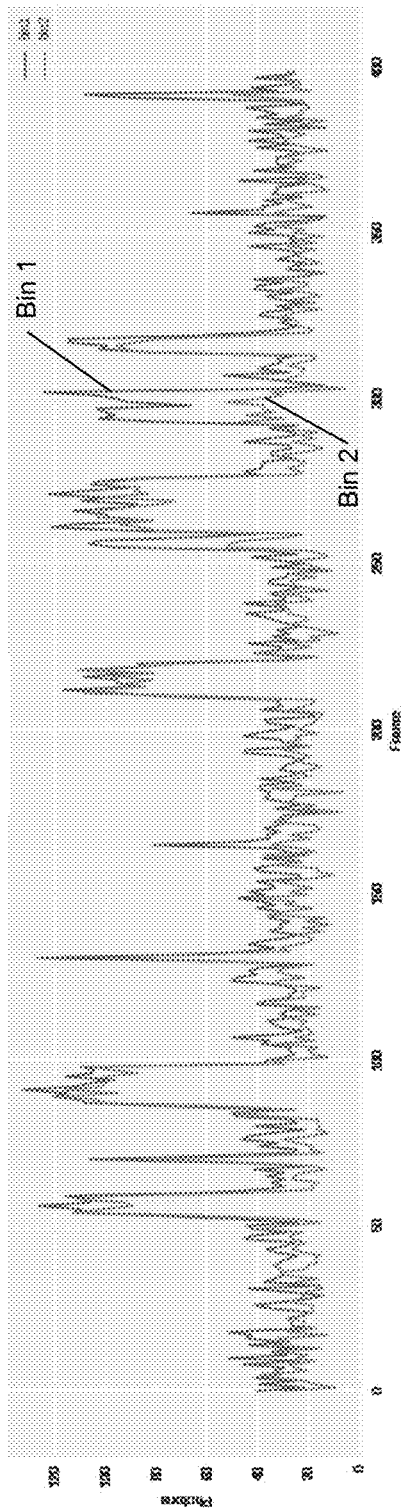
FIG. 25
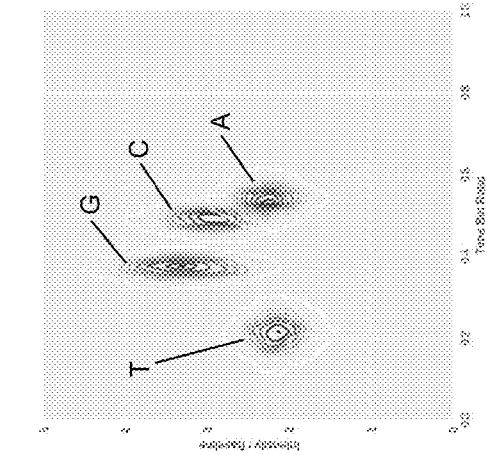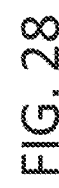
FIG. 28
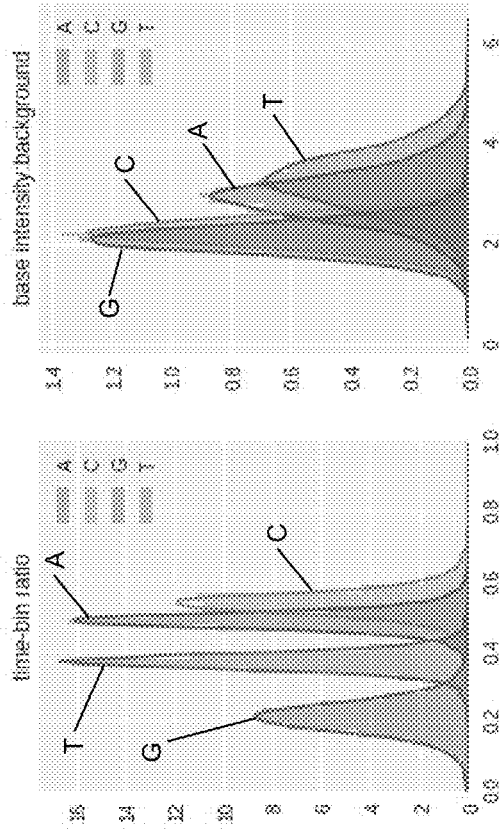
FIG. 27
FIG. 26

MACHINE LEARNING ENABLED PULSE AND BASE CALLING FOR SEQUENCING DEVICES

CROSS-REFERENCE TO RELATED APPLICATIONS

This application claims the benefit under 35 U.S.C. § 119 to U.S. Provisional Application Ser. No. 62/622,754, titled "MACHINE LEARNING ENABLED PULSE AND BASE CALLING FOR SEQUENCING DEVICES", and filed on Jan. 26, 2018, which is incorporated by reference herein in its entirety.

BACKGROUND

The present disclosure relates generally to automated pulse and base calling methods for biological sequencing and, more specifically to machine learning enabled pulse and base calling for sequencing devices.

Sequencing of nucleic acids (e.g., deoxyribonucleic acid (DNA), ribonucleic acid (RNA)) includes identifying individual of nucleotides in a target nucleic acid. Some nucleic acid sequencing methods include identifying individual nucleotides as they are incorporated into nucleic acid strand complementary to the target nucleic acid. The series of nucleotides for the complementary strand identified during the sequencing process may then allow for identification of the nucleotide sequence for the target nucleic acid strand.

SUMMARY

According to one aspect, a method for identifying nucleotides of a nucleic acid is provided. The method comprises: using at least one computer hardware processor to perform: accessing data obtained from detected light emissions by luminescent labels associated with nucleotides during nucleotide incorporation events for the nucleic acid; and providing the data as input to a trained deep learning model to obtain output identifying nucleotides of the nucleic acid.

According to one embodiment, the deep learning model comprises a convolutional neural network. According to one embodiment, the deep learning model comprises a connectionist temporal classification (CTC)-fitted neural network model.

According to one embodiment, the output identifying nucleotides of the nucleic acid comprises, for each of a plurality of nucleotides, a respective time series of values indicating probabilities that the nucleotide was incorporated into the nucleic acid. According to one embodiment, the output identifying nucleotides of the nucleic acid comprises, for each of a plurality of nucleotides, a probability that the nucleotide was incorporated into the nucleic acid; and the method further comprises identifying a first one of the plurality of nucleotides in the nucleic acid when the probability that the first nucleotide was incorporated into the nucleic acid exceeds a threshold probability.

According to one embodiment, providing the data as input to the trained deep learning model comprises: organizing the data into a plurality of time periods; and providing data for each of the time periods as an input to the trained deep learning model to obtain a corresponding output indicating at least one nucleotide of the nucleic acid. According to one embodiment, an output corresponding to a respective time period provided as input to the trained deep learning model indicates, for each of a plurality nucleotides, a value indicating a probability that the nucleotide was incorporated into the nucleic acid in the time period.

According to one embodiment, providing the data as input to the trained deep learning model comprises: identifying a plurality of portions of the data, each portion corresponding to a respective one of the nucleotide incorporation events; and providing each of the plurality of portions of the data as an input to the trained deep learning model to obtain an output corresponding to the portion of the data. According to one embodiment, the output corresponding to the portion of the data identifies a nucleotide that was incorporated into the nucleic acid.

According to one embodiment, the method further comprises: accessing training data obtained from detected light emissions by luminescent labels associated with nucleotides during nucleotide incorporation events for a plurality of nucleic acids; and training a deep learning model using the training data and information specifying at least some of the nucleotides in the plurality of nucleic acids to obtain the trained deep learning model.

According to one embodiment, the light emissions are responsive to a series of light pulses, and the data includes, for each of at least some of the light pulses, a respective number of photons detected in each of a plurality of intervals of a time period after the light pulse.

According to another aspect, a system for identifying nucleotides of a nucleic acid. The system comprises: at least computer hardware processor; and at least one non-transitory computer-readable storage medium storing instructions that, when executed by the at least one computer hardware processor, cause the at least one computer hardware processor to perform: accessing data obtained from detected light emissions by luminescent labels associated with nucleotides during nucleotide incorporation events for the nucleic acid; and providing the data as input to a trained deep learning model to obtain output identifying nucleotides of the nucleic acid.

According to another aspect, at least one non-transitory computer-readable storage medium storing instructions is provided. The instructions, when executed by at least one computer hardware processor, cause the at least one computer hardware processor to perform: accessing data obtained from detected light emissions by luminescent labels associated with nucleotides during nucleotide incorporation events for the nucleic acid; and providing the data as input to a trained deep learning model to obtain output identifying nucleotides of the nucleic acid.

According to another aspect, a method for training a deep learning model for identifying nucleotides of a nucleic acid is provided. The method comprises: using at least one computer hardware processor to perform: accessing data obtained from detected light emissions by luminescent labels associated with nucleotides during nucleotide incorporation events for a plurality of nucleic acids; and training the deep learning model using the data and information specifying at least some of the nucleotides in the plurality of nucleic acids.

According to one embodiment, training the deep learning model using the data and the information specifying at least some of the nucleotides of the plurality of nucleic acids comprises: providing at least a portion of the data as input to the deep learning model to obtain an output identifying nucleotides of at least one of the plurality of nucleic acids; and training the deep learning model based on a difference between the nucleotides of the at least one nucleic acid identified by the output and nucleotides of the at least one nucleic acid specified by the information.

According to one embodiment, the method further comprises: retraining the deep learning model to obtain an updated deep learning model; and propagating updates to the deep learning model to one or more sequencing devices.

According to one embodiment, the deep learning model comprises a convolutional neural network. According to one embodiment, the deep learning model comprises a connectionist temporal classification (CTC)-fitted neural network model.

According to one embodiment, the information specifying at least some of the nucleotides in the plurality of nucleic acids comprises a sequence of nucleotides of at least one of the plurality of nucleic acids and the data includes data corresponding to nucleotide incorporation events for the at least one nucleic acid, and training the deep learning model comprises: reversing the sequence of nucleotides of the at least one nucleic acid; and training the deep learning model using the data corresponding to incorporation events for the at least one nucleic acid and the reversed sequence of nucleotides of the at least one nucleic acid.

According to one embodiment, the method further comprises: accessing data obtained from detected light emissions by luminescent labels associated with nucleotides during nucleotide incorporation events for a nucleic acid; and providing the data as input to the trained deep learning model to obtain output identifying nucleotides of the nucleic acid.

According to one embodiment, the method further comprises: retraining the deep learning model using the data obtained from detected light emissions by luminescent labels associated with nucleotides during nucleotide incorporation events for the nucleic acid and the output identifying nucleotides of the nucleic acid.

According to one embodiment, accessing the data comprises obtaining data collected by a plurality of photodetectors. According to one embodiment, the light emissions are responsive to a series of light pulses, and the data includes, for each of at least some of the light pulses, a respective number of photons detected in each of a plurality of intervals of a time period after the light pulse.

According to another aspect, a system for training a deep learning model for identifying nucleotides of a nucleic acid is provided. The system comprises: at least computer hardware processor; and at least one non-transitory computer-readable storage medium storing instructions that, when executed by the at least one computer hardware processor, cause the at least one computer hardware processor to perform: accessing data obtained from detected light emissions by luminescent labels associated with nucleotides during nucleotide incorporation events for a plurality of nucleic acids; and training the deep learning model using the data and information specifying at least some of the nucleotides in the plurality of nucleic acids.

According to another aspect, at least one non-transitory computer-readable storage medium storing instructions is provided. The instructions, when executed by at least one computer hardware processor, cause the at least one computer hardware processor to perform: accessing data obtained from detected light emissions by luminescent labels associated with nucleotides during nucleotide incorporation events for the nucleic acid; and providing the data as input to a trained deep learning model to obtain output identifying nucleotides of the nucleic acid.

According to another aspect, a method for identifying nucleotides of a nucleic acid is provided. The method comprises: using at least one computer hardware processor to perform: accessing data obtained from detected light emissions by luminescent labels associated with nucleotides, the light emissions responsive to a series of light pulses, the data including, for each of at least some of the light pulses, a respective number of photons detected in each of a plurality of intervals in a time period after the light pulse; and providing the data as input to a trained machine learning model to obtain output identifying nucleotides of the nucleic acid.

According to one embodiment, the data includes data indicating a respective number of photons in each of a first and second time interval in a first time period after a first light pulse in the series of light pulses. According to one embodiment, the data further includes a respective number of photons in each of a first and second time interval in a second time period after a second light pulse in the series of light pulses.

According to one embodiment, providing the data as input to the trained machine learning model comprises arranging the data into a data structure having columns wherein: a first column holds the number of photons in each of a first and second time interval in a first time period after a first light pulse in the series of light pulses, and a second column holds the number of photons in each of a first and second time interval in a second time period after a second light pulse in the series of light pulses. According to one embodiment, providing the data as input to the trained machine learning model comprises arranging the data in an image, wherein each pixel of the image specifies a number of photons detected in an interval of a time period after one of the at least some pulses. According to one embodiment, providing the data as input to the trained machine learning model comprises arranging the data into a data structure having rows wherein each of the rows holds numbers of photons in a respective interval corresponding to the at least some light pulses.

According to one embodiment, providing the data as input to the trained machine learning model comprises: identifying a plurality of portions of the data, each portion corresponding to a respective one of the nucleotides of the nucleic acid; and providing each of the plurality of portions of the data as an input to the trained machine learning model to obtain an output corresponding to the portion of the data. According to one embodiment, identifying a portion of the data as corresponding to a respective nucleotide of the nucleic acid comprises: comparing a number of photons in a first one of the plurality of intervals in the portion of data to a number of photons in at least one of the plurality of intervals separate from the first interval in the portion of data.

According to one embodiment, the machine learning model comprises a deep learning model. According to one embodiment, the deep learning model comprises a convolutional neural network. According to one embodiment, the machine learning model comprises a connectionist temporal classification (CTC)-fitted neural network model.

According to one embodiment, the method further comprises: accessing training data obtained from detected light emissions by luminescent labels associated with nucleotides during nucleotide incorporation events for a plurality of nucleic acids; and training a machine learning model using the training data and information specifying at least some of the nucleotides in the plurality of nucleic acids to obtain the trained machine learning model.

According to another aspect, a system for identifying nucleotides of a nucleic acid is provided. The system comprises: at least computer hardware processor; and at least one non-transitory computer-readable storage medium storing instructions that, when executed by the at least one computer hardware processor, cause the at least one computer hardware processor to perform: accessing data obtained from detected light emissions by luminescent labels associated with nucleotides, the light emissions responsive to a series of light pulses, the data including, for each of at least some of the light pulses, a respective number of photons detected in each of a plurality of intervals in a time period after the light pulse; and providing the data as input to a trained machine learning model to obtain output identifying nucleotides of the nucleic acid.

According to another aspect, at least one non-transitory computer-readable storage medium storing instructions is provided. The instructions that, when executed by at least one computer hardware processor, cause the at least one computer hardware processor to perform: accessing data obtained from detected light emissions by luminescent labels associated with nucleotides, the light emissions responsive to a series of light pulses, the data including, for each of at least some of the light pulses, a respective number of photons detected in each of a plurality of intervals in a time period after the light pulse; and providing the data as input to a trained machine learning model to obtain output identifying nucleotides of the nucleic acid.

According to another aspect, a method includes obtaining, with a processing device, raw data detected from luminescent labels associated with nucleotides during nucleotide incorporation events; and applying a machine learning technique to automatically identify one or more individual nucleotides from the raw data.

According to another aspect, a method includes obtaining, from one or more sequencing devices, raw data detected from luminescent labels associated with nucleotides during nucleotide incorporation events; and processing, using a computing device, the raw data to perform a comparison of base calls produced by a learning enabled, automatic base calling module of the one or more sequencing devices with actual values associated with the raw data, wherein the base calls identify one or more individual nucleotides from the raw data; based on the comparison, creating an update to the learning enabled, automatic base calling module using at least some of the obtained raw data; and making the update available to the one or more sequencing devices.

BRIEF DESCRIPTION OF THE DRAWINGS

Various aspects and embodiments of the application will be described with reference to the following figures. It should be appreciated that the figures are not necessarily drawn to scale. Items appearing in multiple figures are indicated by the same reference number in all the figures in which they appear.

FIGS. 16A-16D illustrate, respectively, four different example normalized 2D matrix representations of pulse trace data for each of the four base types, in accordance with some embodiments of the technology described herein.

FIG. 25 is a 400-frame segment of a real data trace for comparison with simulated data traces, in accordance with some embodiments of the technology described herein.

FIG. 26 is a fitted distribution of background-subtracted time-bin ratio, taken from real data, in accordance with some embodiments of the technology described herein.

FIG. 27 is a fitted distribution of base intensity, as a ratio above baseline, taken from real data, in accordance with some embodiments of the technology described herein.

FIG. 28 is an intersection of the distributions of FIG. 26 and FIG. 27, in accordance with some embodiments of the technology described herein.

DETAILED DESCRIPTION

Figure 1:
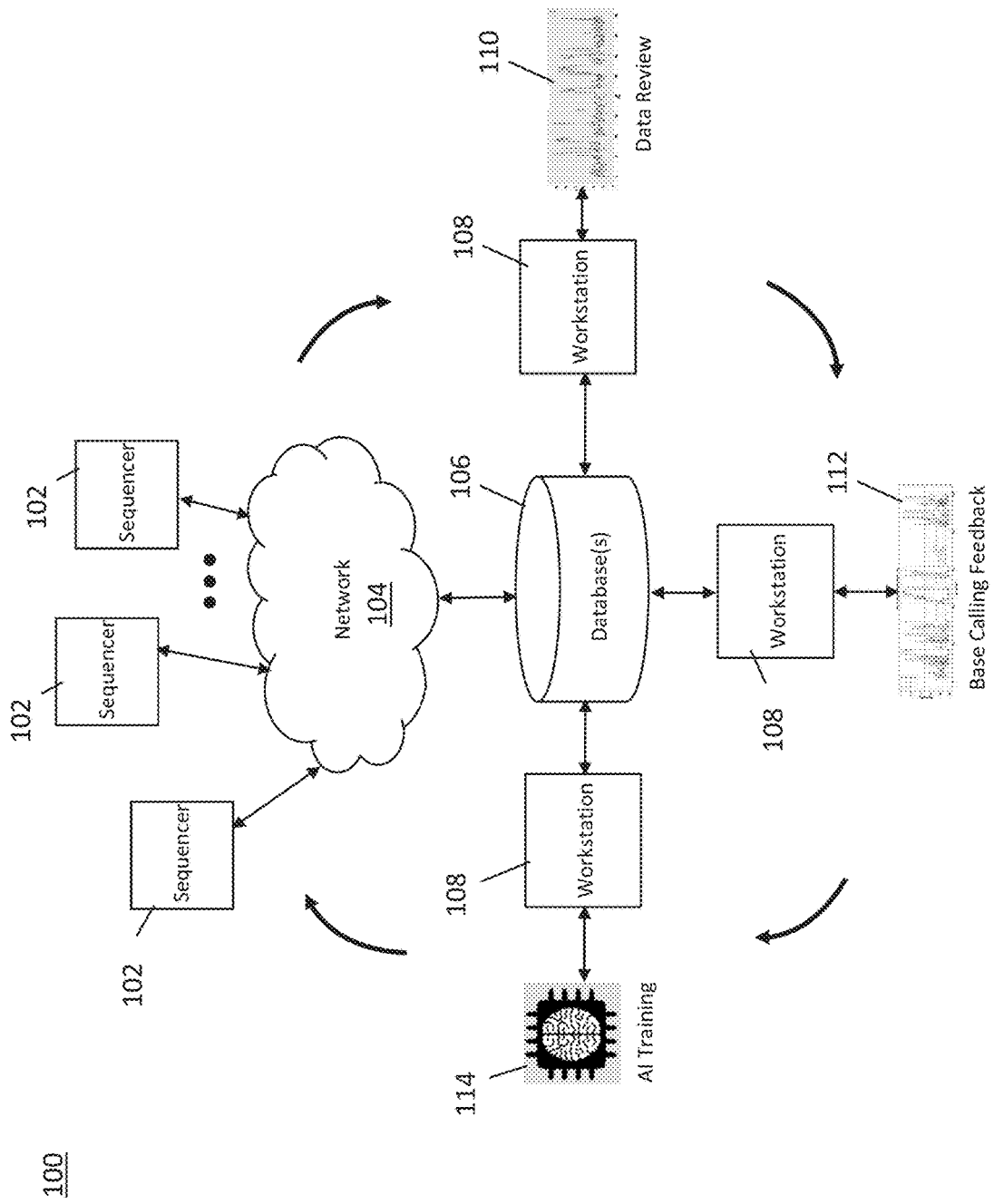
FIG. 1 is a schematic diagram of an exemplary ecosystem in which sequencing devices using learning enabled base calling may be employed, in accordance with some embodiments of the technology described herein.

Embodiments described herein relate generally to sequencing of nucleic acids, such as DNA and RNA, and in particular to techniques for automatically identifying nucleotides based upon data acquired from a sensor. Nucleic acid sequencing allows for the determination of the order and position of nucleotides in a target nucleic acid. Some nucleic acid sequencing methods are based on sequencing by synthesis, in which the identity of a nucleotide is determined as the nucleotide is incorporated into a newly synthesized strand of nucleic acid that is complementary to the target nucleic acid. During sequencing, a polymerizing enzyme (e.g., DNA polymerase) may couple (e.g., attach) to a priming location of a target nucleic acid molecule and add or incorporate nucleotides to the primer via the action of the polymerizing enzyme, which can be generally referred to as a primer extension reaction.

The inventors have developed novel techniques for identification of nucleotides of a nucleic acid (e.g., DNA and/or RNA) using machine learning models. Conventional techniques that use machine learning models to identify nucleotides of a nucleic acid may require human (e.g., domain expert) involvement to identify "informative" features to extract from data collected about nucleotide incorporation of a nucleic acid. The inventors have recognized that it is difficult to identify a set of features that can be used by a machine learning model to identify nucleotides of a nucleic acid reliably, as doing so involves what is often termed "feature engineering"—repeated trial and error of candidate feature sets. In the end, such "feature engineering" may not determine the best features to use for identifying nucleotides, leading to suboptimal identification performance.

The inventors have developed machine learning techniques for identifying nucleotides of a nucleic acid that do not require manually determining individual features to use for identifying nucleotides. Rather, in some embodiments, deep learning techniques are used to automatically learn which information in the collected data is informative for the nucleotide identification task by training a deep learning model to process sensor data directly (or with minor pre-processing), and using the trained deep learning model to identify nucleotides based on detected light emissions by luminescent labels during nucleotide incorporation events.

Accordingly, some embodiments provide for a method for identifying nucleotides (e.g., adenosine, thymine, guanine, and/or cytosine) of a nucleic acid. The method comprises: (1) accessing data obtained from detected light emissions by luminescent labels associated with nucleotides (e.g., responsive to light pulses) during nucleotide incorporation events for the nucleic acid; and (2) providing the data as input to a trained deep learning model (e.g., a recurrent neural network, a convolutional neural network, and/or a connectionist temporal classification-fitted neural network model) to obtain output identifying nucleotides of the nucleic acid.

In some embodiments, the output identifying nucleotides of the nucleic acid comprises, for each of a plurality of nucleotides, a respective time series of values indicating probabilities that the nucleotide was incorporated into the nucleic acid. In some embodiments, the output identifying nucleotides of the nucleic acid comprises, for each of a plurality of nucleotides, a probability that the nucleotide was incorporated into the nucleotide; and the method further comprises identifying a first one of the plurality of nucleotides in the nucleic acid when the probability that the first nucleotide was incorporated into the nucleic acid exceeds a threshold probability.

In some embodiments, the computer hardware processor may provide the data as input to the trained deep learning model by organizing the data into time periods, and providing data for each of the time periods as input to the trained deep learning model to obtain a corresponding output indicating at least one nucleotide of the nucleic acid. In some embodiments, the output corresponding to a respective time period of data provided as input to the trained deep learning model indicates, for each of a plurality of nucleotides, a probability that the nucleotide was incorporated into the nucleic acid during the time period.

In some embodiments, providing the data as input to the trained deep learning model comprises: identifying a plurality of portions of the data, each portion corresponding to a respective one of the nucleotide incorporation events, and providing each of the plurality of portions of the data as an input to the trained deep learning model to obtain a corresponding output corresponding to the portion of the data. In some embodiments, the output corresponding to the portion of the data identifies a nucleotide that was incorporated into the nucleic acid.

In some embodiments, a method for identifying nucleotides (e.g., adenosine, thymine, guanine, and/or cytosine) of a nucleic acid is provided. The method comprises using at least one hardware processor to perform: accessing data obtained from detected light emissions by luminescent labels associated with nucleotides (e.g., adenosine, thymine, guanine, and/or cytosine), the light emissions responsive to a series of light pulses, the data including, for each of at least some of the light pulses, a respective number of photons detected in each of a plurality of intervals in a time period after the light pulse; and providing the data as input to a trained machine learning model (e.g., a convolutional neural network and/or a connectionist temporal classification-fitted neural network model) to obtain output identifying nucleotides of the nucleic acid.

In some embodiments, the data includes data indicating a respective number of photons in each of a first and second time interval in a first time period after a first light pulse in the series of light pulses. In some embodiments, the data further includes a respective number of photons in each of a first and second time interval in a second time period after a second light pulse in the series of light pulses. In some embodiments, providing the data as input to the trained machine learning model comprises arranging the data into a data structure (e.g., a matrix) having columns wherein: a first column holds the number of photons in each of a first and second time interval in a first time period after a first light pulse in the series of light pulses, and a second column holds the number of photons in each of a first and second time interval in a second time period after a second light pulse in the series of light pulses. In some embodiments, providing the data as input to the trained machine learning model comprises arranging the data into a data structure (e.g., a matrix) having rows wherein each of the rows holds numbers of photons in a respective interval corresponding to the at least some light pulses. In some embodiments, providing the data as input to the trained machine learning model comprises arranging the data in an image, wherein each pixel of the image specifies a number of photons detected in an interval of a time period after one of the at least some pulses.

In some embodiments, providing the data as input to the trained machine learning model comprises: identifying a plurality of portions of the data, each portion corresponding to a respective one of the nucleotides of the nucleic acid, and providing each of the plurality of portions of the data as an input to the trained machine learning model to obtain an output corresponding to the portion of the data. In some embodiments, identifying a portion of the data as corresponding to a respective nucleotide of the nucleic acid comprises: comparing a number of photons in a first one of the plurality of intervals in the portion of data to a number of photons in at least one of the plurality of intervals separate from the first interval in the portion of data.

In some embodiments, a method for training a deep learning model (e.g., a convolution neural network, and/or a connectionist-temporal classification-fitted neural network) for identifying nucleotides (e.g., adenosine, thymine, guanine, and/or cytosine) of a nucleic acid is provided. The method comprises: using a computer hardware processor to perform: accessing data obtained from detected light emissions by luminescent labels associated with nucleotides during nucleotide incorporation events for a plurality of nucleic acids; and training the deep learning model using the data and information specifying at least some of the nucleotides in the plurality of nucleic acids.

In some embodiments, training the deep learning model using the data and the information specifying at least some of the nucleotides of the plurality of nucleic acids comprises: providing at least a portion of the data as input to the deep learning model to obtain an output identifying nucleotides of at least one of the plurality of nucleic acids; and training the deep learning model based on a difference between the nucleotides of the at least one nucleic acid identified by the output and nucleotides of the at least one nucleic acid specified by the information.

In some embodiments, the method further comprises: comprising retraining the deep learning model to obtain an updated deep learning model; and propagating updates to the deep learning model to one or more sequencing devices. In some embodiments, the information specifying at least some of the nucleotides in the plurality of nucleic acids comprises a sequence of nucleotides of at least one of the plurality of nucleic acids and the data includes data corresponding to nucleotide incorporation events for the at least one nucleic acid, and training the deep learning model comprises: reversing the sequence of nucleotides of the at least one nucleic acid; and training the deep learning model using the data corresponding to incorporation events for the at least one nucleic acid and the reversed sequence of nucleotides of the at least one nucleic acid.

The techniques described herein integrate deep learning models into sequencing devices to improve sequencing of nucleic acids (e.g., DNA and/or RNA). The techniques train a deep learning model to identify features from sequencing data (e.g., detected light emissions of luminescent labels)

obtained from incorporation of nucleotides into nucleic acids (e.g., by a photodetector). The trained deep learning model may then be integrated into a sequencing device and used to identify nucleotides of a nucleic acid during synthesis of the nucleic acid. Integration of the trained deep learning model improves the accuracy with which nucleotides of a nucleic acid are identified, and thus improves the reliability and accuracy with which the sequencing device sequences nucleic acids.

Each nucleotide may be associated with a luminescent molecule (e.g., fluorophore) that emits light in response to excitation, and which is used to label each type of nucleotide to discriminate among the different types of nucleotides. For example, a set of four labels may be used to label the nucleobases present in DNA such that each marker of the set is associated with a different nucleobase, e.g., a first label being associated with adenine (A), a second label being associated with cytosine (C), a third label being associated with guanine (G), and a fourth label being associated with thymine (T). A label may be coupled to a nucleotide through bonding of the label to the nucleotide either directly or indirectly via a linker molecule.

As the primer extension reaction occurs, a nucleotide and its respective luminescent labels are retained by the polymerizing enzyme during incorporation of the nucleotide into the synthesized complementary nucleic acid. The luminescent label can be excited by pulses of light during the period in which the nucleotide is incorporated into the synthesized nucleic acid and emits light characteristic of the label. In some embodiments, the label is attached, either directly or indirectly through a linker molecule, to a terminal phosphate of a nucleotide such that the label is detached or released from the nucleotide via the action of the polymerizing enzyme during incorporation of the nucleotide (e.g., cleavage of a phosphate bond). Sensing and analyzing the light emitted by the luminescent label in response to the excitation can allow identifying the nucleotide that was incorporated. As the primer extension reaction occurs, excitation, sensing and analysis is performed for each subsequent nucleotide added to the synthesized nucleic acid. The sequence of the target nucleic acid can be determined from the complementary sequence of the synthesized nucleic acid.

The light emitted by the luminescent label may have a number of characteristics that can be used to distinguish the label from other labels, and thus identify a nucleotide. These characteristics include intensity (e.g., probability of emitting light), a temporal characteristic (e.g., rate of decay of the probability of photon emission after excitation, pulse duration for incorporation and/or inter-pulse duration before and/or after incorporation), a spectral characteristic (e.g., wavelength(s) of light emitted), or any combination thereof. The light emitted by the luminescent label may be detected by a photodetector that can detect one of more of these characteristics. An example of a suitable photodetector is described in U.S. patent application Ser. No. 14/821,656 entitled "INTEGRATED DEVICE FOR TEMPORAL BINNING OF RECEIVED PHOTONS," filed on Aug. 7, 2015, and which is hereby incorporated by reference in its entirety. As described therein, the photodetector may have the capability of detecting the arrival times of photons, which can allow for determining temporal characteristics of the light emitted by the labels. Detecting temporal characteristics of the emitted light can in turn allow for discriminating between labels that emit light with different temporal characteristics. One example of a temporal characteristic is luminance lifetime. A luminescent molecule, such as a fluorophore, may emit photons in response to excitation. The probability of the luminescent molecule emitting a photon decreases with time after the excitation occurs. The rate of decay in the probability may be exponential. The "lifetime" is characteristic of how fast the probability decays over time. A fast decay is said to have a short lifetime, while a slow decay is said to have a long lifetime. Detecting temporal characteristics of the light emitted by luminescent molecules can allow distinguishing luminescent molecules that have different lifetimes. Labeling different nucleotides with luminescent molecules having different lifetimes can allow distinguishing between the nucleotides based upon a temporal characteristic of the light detected.

The photodetector described in the aforementioned U.S. patent application Ser. No. 14/821,656 can detect the time of arrival of photons with nanosecond or picosecond resolution, and can time-bin the arrival of incident photons. Since the emission of photons is probabilistic, the label may be excited a plurality of times and any resulting photon emissions may be time-binned. Performing such a measurement a plurality of times allows populating a histogram of times at which photons arrived after an excitation event. This information can be analyzed to calculate a temporal characteristic of the emitted light, which in turn can allow distinguishing the label from another label based on the temporal characteristic.

Embodiments of systems, devices and methods described herein provide an ecosystem of sequencing instruments that are able to analyze data from a photodetector to sequence a nucleic acid based on the characteristics of the detected light. In some embodiments, these techniques may be implemented to analyze a stream of data from the photodetector, which may allow for sequencing of the nucleic acid in real-time while data is collected by the photodetector. In some embodiments, these techniques may be implemented to analyze data from the photodetector at a later point in time after acquisition. These techniques may, for example, be implemented by a learning-enabled "pulse caller" and/or a learning-enabled "base caller," which may be software and/ or hardware modules of the sequencing instruments or other devices. Additional details regarding pulse and base calling are described in further detail hereinafter; however, generally speaking a "pulse caller" analyzes the raw sensor data to identify time periods when pulses of luminescence from the label occur, signifying a dye-conjugated nucleotide being incorporated into the oligonucleotide strand by the polymerase. A "base caller" analyzes characteristics of the light detected during the time periods identified by the pulse caller to determine, or "call" the identity of the nucleotides. As more data is acquired by the deployed sequencing instruments during use, one or more data processing techniques may be employed in order to analyze the performance of the learning-enabled pulse/base callers and, as a result, update or replace the architectures with improved versions thereof (which improved versions may also be subject to continuing analysis and retraining). Conventional techniques for analyzing data may involve using models based on first-principle calculations of expected physics and chemistry of a system. In contrast, the machine learning techniques of some embodiments of the technology described herein may allow for updates in the model based on observed system behavior, including observed system behavior derived from acquired data, which may differ from assumptions used to generate a static model.

The techniques described herein may allow for analysis of the data that involves identifying the bases directly from the raw intensity traces, which may eliminate or reduce the need to include a pulse calling step.

Referring initially to FIG. 1, a schematic diagram of an exemplary ecosystem 100 is depicted, in which sequencing devices using learning enabled base calling may be employed. More details with respect to example learning architectures that may be used by the sequencing devices are described in further detail hereinafter. In any case, sequencing instruments/devices ("sequencer") 102 may be deployed in one or more locations and may be connected to a network 104 in a wired or wireless fashion, depending on location and physical resource conditions. Whether in real time or at a later point in time after acquisition, sequencing data obtained from the sequencing devices 102 may be uploaded, via one or more networks 104 and stored in one or more databases 106. In some embodiments, sequencing data may be uploaded as raw time-intensity traces for individual time bins. For example, the data may include a time-intensity trace for a first bin of a photodetector having photon counts over time detected by the first bin and a time-intensity trace for a second bin of a photodetector having photon counts over time detected by the second bin. In some embodiments, the representation may be computed by passing raw time-intensity traces through a function designed to reduce a size of the data. The function may extract features from the time-intensity traces such that the extracted features identify content information of the time-intensity traces and are included in the resulting representation. The representation may have a format that allows for subsequent implementation of a base caller. Such a technique may be applied prior to uploading of the data, and the reduced size of the data may improve the uploading process.

The sequencing data may be accessible via one or more workstations 108 for analysis, annotation and training to improve, for example, accuracy of one or more learning enabled base calling methods utilized by the sequencing devices 102. Advantageously, periodic updates to the base calling algorithms may be made available to the sequencing devices 102, for example, by downloading via the one or more networks 104. It should be appreciated that other computing device(s) (e.g., a single computing device, multiple computing devices co-located in a single physical location or located in multiple physical locations remote from one another, one or more computing devices part of a cloud computing system, etc.) may perform some or all aspects of the base calling algorithms, as aspects of the technology described herein are not limited in this respect. In such embodiments, the other computing device(s) may receive periodic updates to the base calling algorithms. Although FIG. 1 depicts multiple workstations 108 used to perform various functions such as data review 110, base calling feedback 112, and AI training 114, it will be appreciated that a single workstation 108 may perform one, several, or all such functions. The specific depiction in FIG. 1 is useful for representing a virtuous circle (or cycle) in such an ecosystem 100 whereby devices 102 improve in performance over time as more and more data is collected, which data is in turn used to train and improve the artificial intelligence used by the devices 102.

Figure 2:
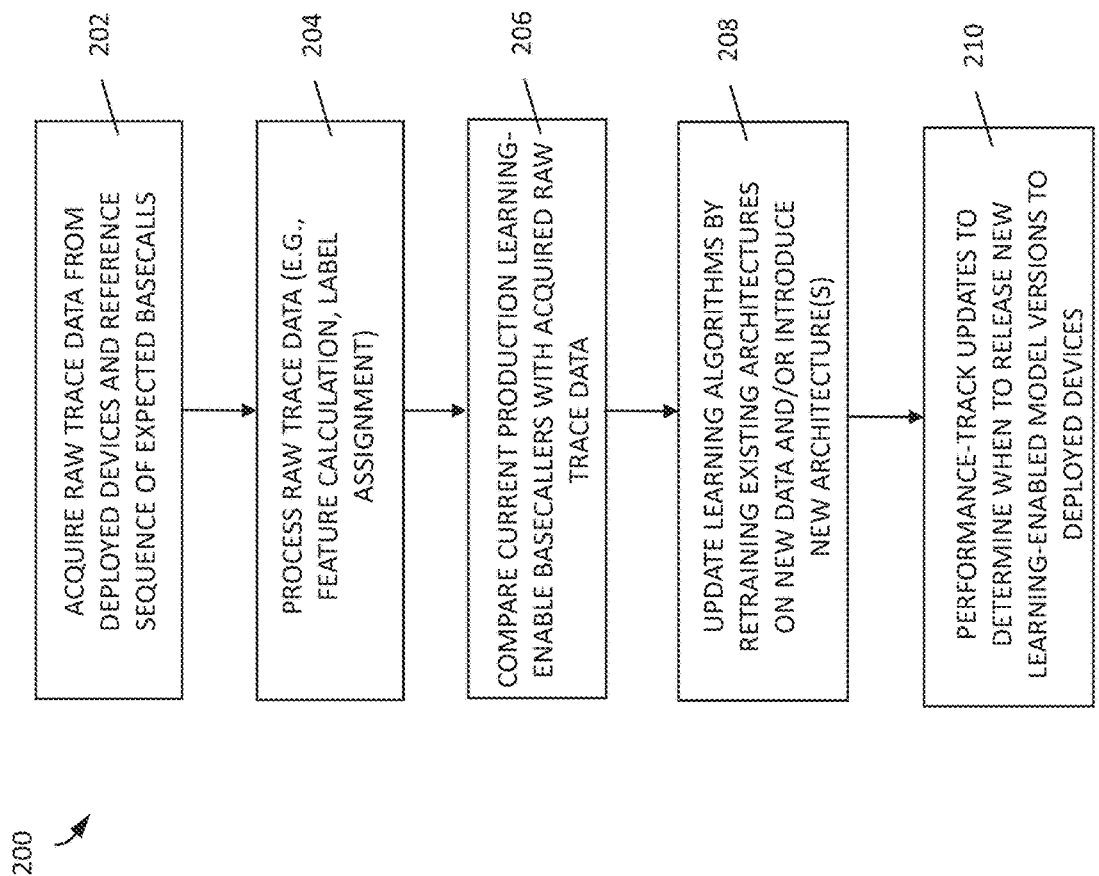
FIG. 2 is a high-level flow diagram that illustrates an exemplary process for implementing a virtuous circle within the exemplary ecosystem of FIG. 1, in accordance with some embodiments of the technology described herein.

Referring now to FIG. 2, there is shown a high-level flow diagram that illustrates an exemplary process for implementing a virtuous circle suggested within the exemplary ecosystem 100 of FIG. 1. As indicated at operation 202, raw trace data (e.g., first and second time bin photon counts) is acquired from the deployed sequencing devices along with the reference sequence of expected base calls provided by the user (when such information is available), and which data may be transmitted to a central repository (e.g., database 106 in FIG. 1). Here, a user may be, for example, a customer who agrees to transmit anonymous sequencing data or an R & D technician performing sequencing runs for any of a variety of diagnostic purposes. The raw data may be viewed and downloaded using, for example, a workstation 108 in FIG. 1.

Then, as shown at operation 204, raw data from the deployed sequencing devices may be processed into a form amenable to learning. This may entail, for example, feature calculation (in the event models requiring pre-calculated features are to be used) and label assignment. In this context. "labels" refer to the true values of base calls corresponding to each trace of photon intensities. The labels may, in one embodiment, be discretized to include a one-to-one mapping of individual bases to temporal pulse-events derived using a previous iteration of pulse/base-calling models (learning-enabled or otherwise). Alternatively, the labels can be derived through pulse/base calling with a previous model and sequence alignment to the given reference genome, such that pulses or trace segments can be associated with one or more reference bases. In still another approach, unsupervised methods may be used, in which only the reference sequence is saved, without attempting to coordinate with specific areas of the trace during processing, and instead using an edit distance-based cost function during model training (e.g., a Neural Hash Function). It is envisioned that raw data may be processed, for example, as one-off job or on a schedule for newly deposited data to produce processed data.

At operation 206, current production learning-enabled pulse/base callers may be benchmarked against incoming data to track their performance over time. With this comparison information, updates to the learning algorithms may be made as indicated at operation 208. Such updates may be implemented by, for example, retraining an existing architecture on new data or introducing new architectures to be trained on some or all of the available up-to-date data. Model training may be queued by selecting processed data and a model architecture, thereby producing a trained model with stored weights. The retraining and supplemental training of existing architectures on new data may be performed automatically as data is acquired, and as indicated at operation 210, performance tracked to determine if and/or when a new version of the model with updated hyper-parameters and/or weights should be released and uploaded to customer sequencing devices or to the cloud to handle distributed analysis of customer data. Here, model evaluation may be queued by selecting a trained model and processed data, thereby producing predictions and/or benchmarks. Such benchmarks may in turn be viewed and/or sorted, for example, by accuracy or other metric, and a "leaderboard" may be established for models (e.g., using a same test set, for different instruments/dye sets, etc.).

One ancillary benefit of creating such a system for tracking base caller progress is that the system may be designed as a general framework to support any number of learning projects. For example, the system may be applied to any task where it is desired to track the performance of models in light of constantly accruing new data. For instance, the system may be used to train learning enabled single nucleotide polymorphisms (SNP) callers, cancer prognosis predictors, etc.

It will be appreciated that the accuracy of the learning enabled pulse/base calling algorithms described herein should increase as more data becomes available to train a model to learn these complex patterns. As described in further detail herein, additional techniques may be employed with respect to additional data generation. For example, a data simulator may be created to produce essentially unlimited amounts of data that mimics some of the readily observable macro properties of actual sequencing data. Training a model on such simulated data allows presetting of some of the model weights before more in-depth training is applied using real data. After this "pre-training," a model is exposed to a multitude of examples of how to call pulses, which is a significant challenge. The model would then only have to fine tune its ability to call bases given some of the more nuanced properties of real data. In addition (and as also outlined in further detail below), data augmentation techniques may be applied to real data, including looking at both the forward and reverse of each trace (thereby doubling the data), and expanding datasets to include time-translations of each signal window.

In some embodiments, learning-enabled pulse/base callers may be updated iteratively. In some embodiments, a student-teacher training approach may be implemented to periodically retrain one or more models used by a sequencer. The model(s) may be retrained using data and labels obtained from a previous version of the model. For example, a model for a sequencer may be trained using a set of training data to obtain a first trained model. The first trained model may be referred to as a "teacher model." The teacher model may then be used for identifying nucleotides of one or more nucleic acids using trace data from incorporation events for the nucleic acid(s). One or more outputs of the model identifying the nucleotides of the nucleic acid(s) and the corresponding trace data may then be used as training data to retrain the model to obtain a second trained model. The second trained model may be referred to as a "student model" of the teacher model. The student model may identify nucleic acids more accurately than the teacher model. This process may be performed periodically to update the model(s) of a sequencer. This may account for changes in physical characteristics of wells of the sequencer, and iteratively improve accuracy of the sequencer.

Figure 3:
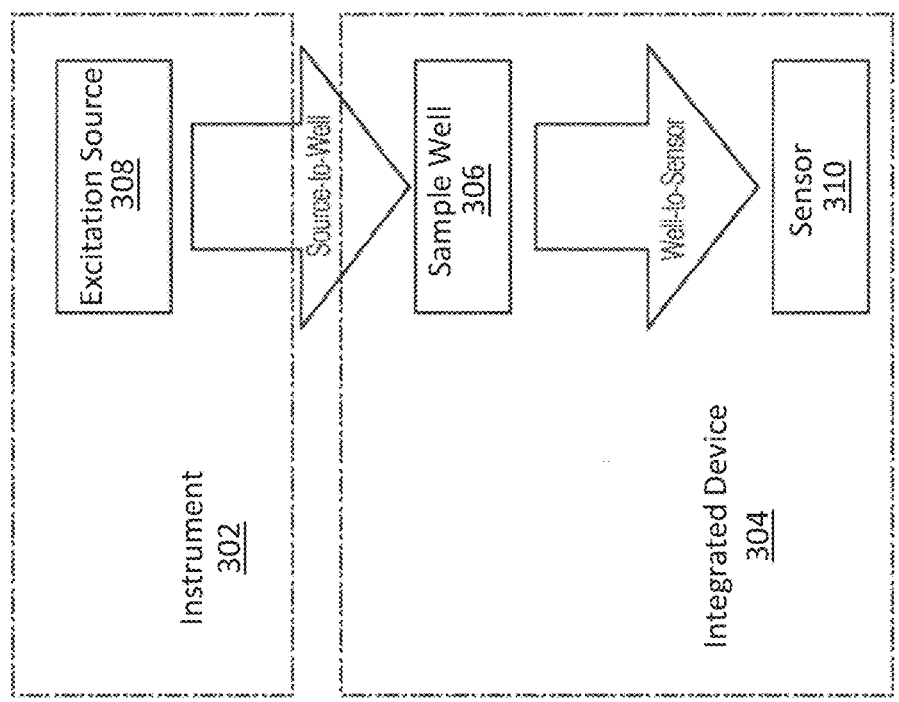
FIG. 3 is a schematic diagram of an exemplary sequencing system which may be used in conjunction with embodiments of a method of implementing a machine learning enabled base caller, in accordance with some embodiments of the technology described herein.

Referring now to FIG. 3, there is shown a schematic diagram of an exemplary sequencing system 300 (e.g., a sequencer 102 of FIG. 1) which may be used in conjunction with embodiments of the automated, machine learning enabled pulse and base calling techniques described hereinafter. It should be understood however, that the techniques described herein may be implemented in other types of sequencing systems. Generally speaking, the exemplary sequencing system 300 includes an instrument 302 that is configured to interface with an integrated device 304 having a plurality of sample wells, where an individual sample well 306 is configured to receive a sample from a specimen (not shown) placed on the surface of the integrated device 304. A specimen may contain multiple samples, and in some embodiments, different types of samples. The plurality of sample wells may have a suitable size and shape such that at least a portion of the sample wells receive one sample from a specimen. In some embodiments, the number of samples within a sample well may be distributed among the sample wells such that some sample wells contain one sample with others contain zero, two or more samples.

In some embodiments, a specimen may contain multiple single-stranded DNA templates, and individual sample wells on a surface of an integrated device may be sized and shaped to receive a single-stranded DNA template. Single-stranded DNA templates may be distributed among the sample wells of the integrated device such that at least a portion of the sample wells of the integrated device contain a single-stranded DNA template. The specimen may also contain tagged dNTPs which then enter in the sample well and may allow for identification of a nucleotide as it is incorporated into a strand of DNA complementary to the single-stranded DNA template in the sample well. In such an example, the "sample" may refer to both the single-stranded DNA and the tagged dNTP currently being incorporated by a polymerase. In some embodiments, the specimen may contain single-stranded DNA templates and tagged dNTPS may be subsequently introduced to a sample well as nucleotides are incorporated into a complementary strand of DNA within the sample well. In this manner, timing of incorporation of nucleotides may be controlled by when tagged dNTPs are introduced to the sample wells of an integrated device.

Excitation energy is provided from an excitation source 308 of the instrument 302 separate from the pixel array of the integrated device. The excitation energy is directed at least in part by elements of the integrated device towards one or more pixels (not shown in FIG. 1) to illuminate an illumination region within the sample well 306. A label may then emit emission energy when located within the illumination region and in response to being illuminated by excitation energy. In some embodiments, one or more excitation sources 308 are part of the instrument of the system where components of the instrument 302 and the integrated device 304 are configured to direct the excitation energy towards one or more pixels.

Emission energy emitted by a sample may then be detected by one or more sensors 310 within a pixel of the integrated device 304. Characteristics of the detected emission energy may provide an indication for identifying the marked associated with the emission energy. Such characteristics may include any suitable type of characteristic, including an arrival time of photons detected by a sensor, an amount of photons accumulated over time by a sensor, and/or a distribution of photons across two or more sensors. In some embodiments, a sensor 310 may have a configuration that allows for the detection of one or more timing characteristics associated with a sample's emission energy (e.g., fluorescence lifetime). The sensor 310 may detect a distribution of photon arrival times after a pulse of excitation energy propagates through the integrated device, and the distribution of arrival times may provide an indication of a timing characteristic of the sample's emission energy (e.g., a proxy for fluorescence lifetime). In some embodiments, the one or more sensors provide an indication of the probability of emission energy emitted by the label (e.g., fluorescence intensity). In some embodiments, a plurality of sensors may be sized and arranged to capture a spatial distribution of the emission energy. Output signals from the one or more sensors may then be used to distinguish a label from among a plurality of labels, where the plurality of labels may be used to identify a sample within the specimen.

Figure 4:
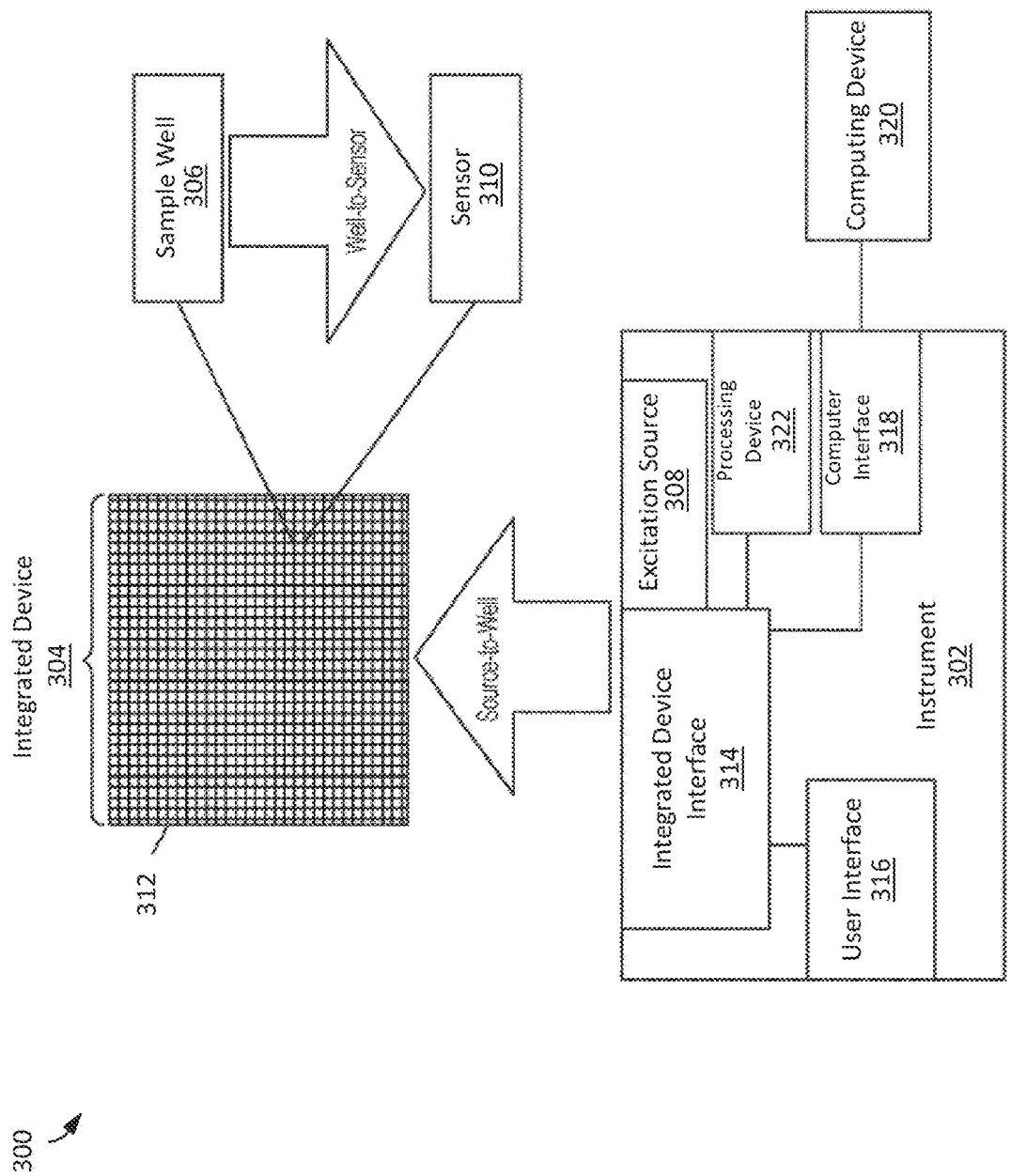
FIG. 4 is a more detailed schematic diagram of the exemplary sequencing system illustrated in FIG. 3, in accordance with some embodiments of the technology described herein.

By way of further illustration, FIG. 4 is a more detailed schematic diagram of the exemplary sequencing system 300 of FIG. 3. Again, the system 300 includes an integrated device 304 that interfaces with an instrument 302. In some embodiments, instrument 302 may include one or more excitation sources 308 integrated as part of instrument 302. In some embodiments, an excitation source 308 may be external to both instrument 302 and integrated device 304, such that instrument 302 may be configured to receive excitation energy from the excitation source 308 and direct it to the integrated device 304. The integrated device 304 may interface with the instrument 302 using any suitable socket for receiving the integrated device 304 and holding it in precise optical alignment with the excitation source 308.

The excitation source 308 may also be located within the instrument and configured to provide excitation energy to the integrated device 304. As also illustrated schematically in FIG. 4, the integrated device 304 has multiple individual pixels, where at least a portion of the pixels 312 may perform independent analysis of a sample. Such pixels 312 may be referred to as "passive source pixels" since a pixel receives excitation energy from a source 308 separate from the pixel, where the source excites a plurality of pixels. A pixel 312 has both a sample well 306 configured to receive a sample and a sensor 310 for detecting emission energy emitted by the sample in response to illuminating the sample with excitation energy provided by the excitation source 308. A sample well 306 may retain the sample in proximity to a surface of integrated device 304 to provide ease in delivery of excitation energy to the sample and detection of emission energy from the sample.

Optical elements for guiding and coupling excitation energy from the excitation source 308 to the sample well 306 of the integrated device 304 may be incorporated in both the integrated device 304 and the instrument 302. Such source-to-well elements may include, for example, one or more grating couplers located on the integrated device 304 to couple excitation energy to the integrated device 304 and waveguides to deliver excitation energy from instrument 302 to sample wells 306 in pixels 312. In some embodiments, elements located on the integrated device 304 may act to direct emission energy from the sample well 306 towards the sensor 310. The sample wells 306, a portion of the excitation source-to-well optics, and the sample well-to-sensor optics are located on the integrated device 304. The excitation source 308 and a portion of the source-to-well components are located in the instrument 302. In some embodiments, a single component may play a role in both coupling excitation energy to a sample well 306 and delivering emission energy from the sample well 306 to sensor 310. Examples of suitable components for coupling excitation energy to a sample well and/or directing emission energy to a sensor, to include in an integrated device, are described in (1) U.S. patent application Ser. No. 14/821,688 entitled "INTEGRATED DEVICE FOR PROBING, DETECTING AND ANALYZING MOLECULES," filed on Aug. 7, 2015; and (2) U.S. patent application Ser. No. 14/543,865 entitled "INTEGRATED DEVICE WITH EXTERNAL LIGHT SOURCE FOR PROBING, DETECTING, AND ANALYZING MOLECULES," filed on Nov. 17, 2014, and both of which are incorporated by reference in their entirety.

With respect to plurality of pixels 312 in the embodiment of FIG. 4, an individual pixel 312 is associated with its own individual sample well 306 and at least one sensor 310. The plurality of pixels 312 may be arranged in an array, and there may be any suitable number of pixels in the array. The number of pixels in integrated device 304 may be in the range of approximately 10,000 pixels to 1,000,000 pixels or any value or range of values within that range. In some embodiments, the pixels may be arranged in an array of 512 pixels by 512 pixels. Integrated device 304 and instrument 302 may include multi-channel, high-speed communication links (not shown) for handling data associated with large pixel arrays (e.g., more than 10,000 pixels).

As further illustrated in FIG. 4, the instrument 302 interfaces with integrated device 304 through an integrated device interface 314. The integrated device interface 314 may include, for example, components to position and/or align the integrated device 304 to the instrument 302 to facilitate or improve coupling of excitation energy from excitation source 308 to the integrated device 304. The excitation source 308 may be any suitable light source that is arranged to deliver excitation energy to at least one sample well. Examples of suitable excitation sources are described in the aforementioned U.S. patent application Ser. No. 14/821,688. In some embodiments, the excitation source 308 includes multiple excitation sources that are combined to deliver excitation energy to the integrated device 304. Such multiple excitation sources may be configured to produce multiple excitation energies or wavelengths. The integrated device interface 314 may receive readout signals from the sensors 310 in the pixels 312 of the integrated device 304. The integrated device interface 314 may be designed such that the integrated device 304 attaches to the instrument 302 by securing the integrated device 304 to the integrated device interface 314.

Referring still to FIG. 4, the instrument 302 further includes a user interface 316 for controlling the operation of instrument 302. The user interface 316 is configured to allow a user to input information into the instrument, such as for example commands and/or settings used to control the functioning of the instrument. In some embodiments, the user interface 316 may include buttons, switches, dials, and a microphone for voice commands. Additionally, the user interface 316 may allow a user to receive feedback on the performance of the instrument and/or integrated device, such as proper alignment and/or information obtained by readout signals from the sensors on the integrated device. In some embodiments, the user interface 316 may provide feedback using a speaker to provide audible feedback, and indicator lights and/or display screen for providing visual feedback. In some embodiments, the instrument 302 includes a computer interface 318 used to connect with an external computing device 320. Any suitable computer interface 318 and computing device 320 may be used. For example, the computer interface 318 may be a USB interface or a FireWire interface. The computing device 320 may be any general purpose computer, such as a laptop or desktop computer. The computer interface 318 facilitates communication of information between the instrument 302 and the computing device 320. Input information for controlling and/or configuring the instrument 302 may be provided through the computing device 320 in communication with the computer interface 318 of the instrument 302. In addition, output information may be received by the computing device 320 through the computer interface 318. Such output information may include, for example, feedback about performance of the instrument 302 and/or integrated device 312 and information from the readout signals of the sensor 310. The instrument 302 may also include a processing device 322 for analyzing data received from the sensor 310 and/or sending control signals to the excitation source 308. In some embodiments, the processing device 322 may comprise a general purpose processor, a specially-adapted processor (e.g., a central processing unit (CPU) such as one or more microprocessor or microcontroller cores, a field-programmable gate array (FPGA), an application-specific integrated circuit (ASIC), a custom integrated circuit, a digital signal processor (DSP), or a combination thereof.) In some embodiments, the processing of data from the sensor 310 may be performed by both the processing device 322 and the external computing device 320. In other embodiments, the computing device 320 may be omitted and processing of data from the sensor 310 may be performed entirely by the processing device 322.

Figure 5A:
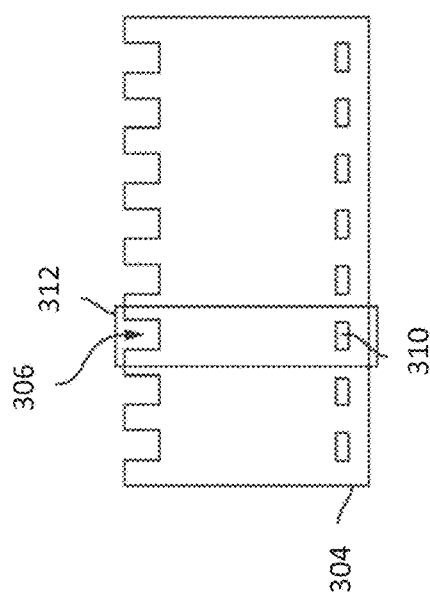
FIG. 5A and FIG. 5B are cross-sectional views illustrating an integrated device of the exemplary sequencing machine in further detail, in accordance with some embodiments of the technology described herein.

Referring now to FIG. 5A, there is shown a cross-sectional schematic diagram of the integrated device 304 illustrating a row of pixels 312. Each pixel 312 includes a sample well 306 and a corresponding sensor 310. The sensor 310 may be aligned and positioned to the sample well 306 such that the sensor 310 receives emission energy emitted by a sample (not shown) within sample well 312. Examples of suitable sensors are described in the aforementioned U.S. patent application Ser. No. 14/821,656.

Figure 5B:
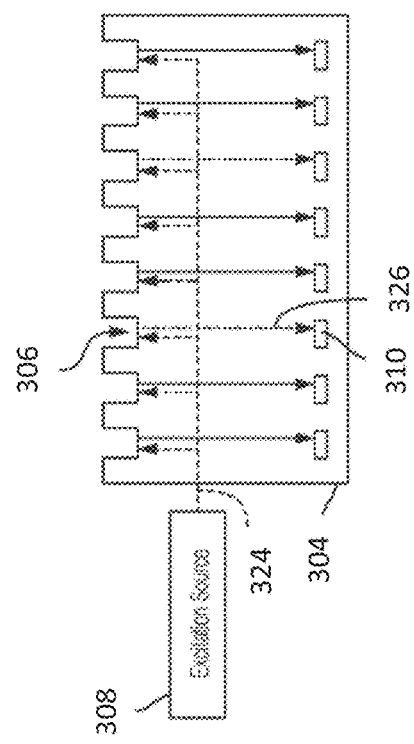

As discussed previously, an excitation source 308 coupled to the integrated device 304 may provide excitation energy to one or more pixels of the integrated device 304. By way of further illustration, FIG. 5B is a cross-sectional schematic diagram illustrating coupling of the excitation source 308 to the integrated device 304 to provide excitation energy 324 (the path of which is shown in dashed lines) to the sample wells 306 of the integrated device 304. Components (not shown) located off of the integrated device 304 may be used to position and align the excitation source 308 to the integrated device. Such components may include, for example, optical components such as lenses, mirrors, prisms, apertures, attenuators, and/or optical fibers. Additional mechanical components may also be included in the instrument 302 to allow for control of one or more alignment components. Such mechanical components may include, for example, actuators, stepper motors, and/or knobs.

The integrated device 304 includes components that direct the excitation energy 324 towards pixels 312 therein. More specifically, within each pixel 312, excitation energy is coupled to the sample well 306 associated with the pixel. Although FIG. 5B illustrates excitation energy coupling to each sample well 306 in a row of pixels 312, in some embodiments, it is possible that excitation energy may not couple to all of the pixels 312 in a given row. In some embodiments, excitation energy may couple to a portion of pixels 312 or sample wells 306 in a row of pixels 312 of the integrated device 304. The excitation energy 324 may illuminate a sample located within a sample well 306. The sample may reach an excited state in response to being illuminated by the excitation energy. When a sample is in an excited state, the sample may emit emission energy 326 as shown in FIG. 5B, which emission energy 326 may in turn be detected by a sensor 310. In some embodiments, the sensor 310 may include multiple sub-sensors.

A sample to be analyzed may be introduced into the sample well 306 of pixel 312. The sample may be a biological sample or any other suitable sample, such as a chemical sample. Further, the sample may include multiple molecules and the sample well 306 may be configured to isolate a single molecule. In some instances, the dimensions of the sample well 306 may act to confine a single molecule within the sample well, thereby allowing measurements to be performed on the single molecule. An excitation source 308 may be configured to deliver excitation energy into the sample well 306, so as to excite the sample or at least one luminescent marker attached to the sample or otherwise associated with the sample while it is within an illumination area within the sample well 306.

When an excitation source delivers excitation energy to a sample well, at least one sample within the well may luminesce, and the resulting emission may be detected by a sensor 310. As used herein, the phrases "a sample may luminesce" or "a sample may emit radiation" or "emission from a sample" mean that a luminescent tag, marker, or reporter, the sample itself, or a reaction product associated with the sample may produce the emitted radiation.

One or more components of the integrated device 304 may direct emission energy towards a sensor 310. The emission energy or energies may be detected by the sensor 310 and converted to at least one electrical signal. The electrical signals may be transmitted along conducting lines in the circuitry of the integrated device 304 connected to the instrument 302 through the integrated device interface 314, such as already described in connection with FIG. 4. The electrical signals may be subsequently processed and/or analyzed by a suitable computing device either located on the instrument 302 or off the instrument 302, such as computing device 320 and/or the processing device 322 shown in FIG. 4.

In operation, parallel analyses of samples within the sample wells are carried out by exciting the samples within the wells using the excitation source and detecting signals from sample emission with the sensors. Emission energy from a sample may be detected by a corresponding sensor and converted to at least one electrical signal. The resulting signal, or signals, may be processed on the integrated device in some embodiments, or transmitted to the instrument for processing by the processing device and/or computing device. Signals from a sample well may be received and processed independently from signals associated with the other pixels.

In some embodiments, a sample may be labeled with one or more markers, and emission associated with the markers is discernable by the instrument. For example the sensor may be configured to convert photons from the emission energy into electrons to form an electrical signal that may be used to discern a lifetime that is dependent on the emission energy from a specific marker. By using markers with different lifetimes to label samples, specific samples may be identified based on the resulting electrical signal detected by the sensor.

A sample may contain multiple types of molecules and different luminescent markers may uniquely associate with a molecule type. During or after excitation, the luminescent marker may emit emission energy. One or more properties of the emission energy may be used to identify one or more types of molecules in the sample. Properties of the emission energy used to distinguish among types of molecules may include a fluorescence lifetime value, intensity, and/or emission wavelength. A sensor may detect photons, including photons of emission energy, and provide electrical signals indicative of one or more of these properties. In some embodiments, electrical signals from a sensor may provide information about a distribution of photon arrival times across one or more time intervals. The distribution of photon arrival times may correspond to when a photon is detected after a pulse of excitation energy is emitted by an excitation source. A value for a time interval may correspond to a number of photons detected during the time interval. Relative values across multiple time intervals may provide an indication of a temporal characteristic of the emission energy (e.g., lifetime). Analyzing a sample may include distinguishing among markers by comparing values for two or more different time intervals within a distribution. In some embodiments, an indication of the intensity may be provided by determining a number of photons across all time bins in a distribution.

The term "nucleic acid," as used herein, generally refers to a molecule comprising one or more nucleic acid subunits. A nucleic acid may include one or more subunits selected from adenosine (A), cytosine (C), guanine (G), thymine (T) and uracil (U), or variants thereof. In some examples, a nucleic acid is deoxyribonucleic acid (DNA) or ribonucleic acid (RNA), or derivatives thereof. A nucleic acid may be single-stranded or double stranded. A nucleic acid may be circular.

The term "nucleotide," as used herein, generally refers to a nucleic acid subunit, which can include A, C, G, T or U, or variants or analogs thereof. A nucleotide can include any subunit that can be incorporated into a growing nucleic acid strand. Such subunit can be an A, C, G, T, or U, or any other subunit that is specific to one or more complementary A, C, G, T or U, or complementary to a purine (i.e., A or G, or variant or analogs thereof) or a pyrimidine (i.e., C, T or U, or variant or analogs thereof).

A nucleotide generally includes a nucleoside and at least 1, 2, 3, 4, 5, 6, 7, 8, 9, 10, or more phosphate ($PO_3$) groups. A nucleotide can include a nucleobase, a five-carbon sugar (either ribose or deoxyribose), and one or more phosphate groups. Ribonucleotides are nucleotides in which the sugar is ribose. Deoxyribonucleotides are nucleotides in which the sugar is deoxyribose. A nucleotide can be a nucleoside monophosphate or a nucleoside polyphosphate. A nucleotide can be a deoxyribonucleoside polyphosphate, such as, e.g., a deoxyribonucleoside triphosphate, which can be selected from deoxyadenosine triphosphate (dATP), deoxycytidine triphosphate (dCTP), deoxyguanosine triphosphate (dGTP), deoxyuridine triphosphate (dUTP) and deoxythymidine triphosphate (dTTP) dNTPs, that include detectable labels (e.g., fluorophores).

With respect to the sensor 310, a photodetector may time bin the arrival of incident photons from a label in response to exposing the label to an excitation source 308 (e.g., by a laser pulse). A label may be repeatedly excited, and the arrival of incident photons from the label may be time binned. As an example, during a 10 ms measurement period, laser excitation pulses may be emitted at a frequency of 100 MHz to excite the label. The label may emit a photon with a low probability (e.g., 1 photon emission in 10,000 excitations). If the label is excited a number of times (e.g., 1 million times) within a 10 ms period, approximately 100 photons may be received. In some instances, a label may not become excited after exposure to an excitation source and not emit a photon after an excitation event, which may contribute to the low probability of emission. As discussed above, the arrival times of the incident photons with respect to the excitation may be time-binned. As such, a photodetector may provide signals representing the number of photons in each time bin.

Figure 6:
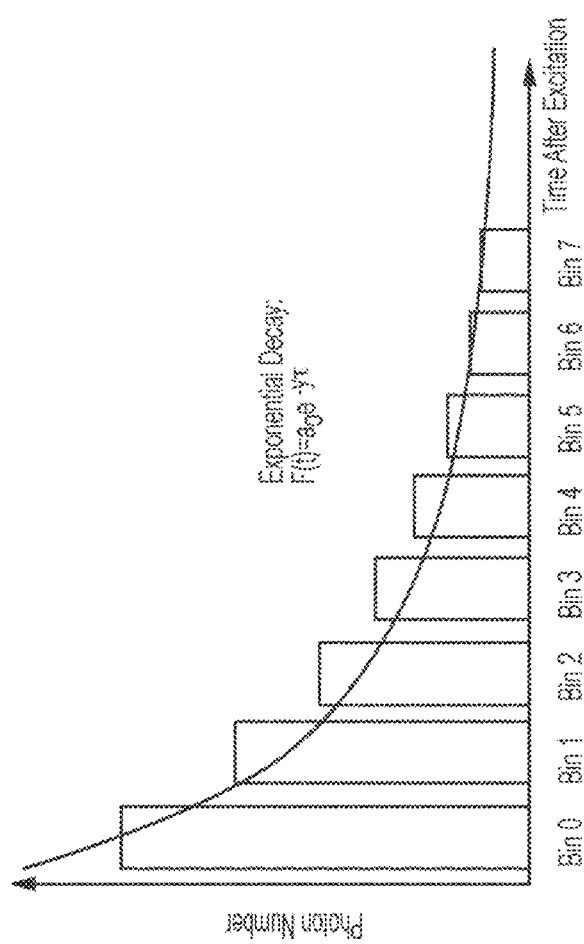
FIG. 6 is a plot of probability of photon emission over time after excitation and the distribution of the number of photons in time bins detected by a photodetector, in accordance with some embodiments, in accordance with some embodiments of the technology described herein.

To further illustrate, FIG. 6 is a graph that shows an example in which a photodetector time-bins the arrival of incident photons into eight time bins. Because the probability of photon emission decays over time, earlier time bins have more photons than the later time bins. By repeatedly exciting the label and detecting the timing of photons emitted, a histogram can be populated that approximates the decay in the probability of photon emission over time, as shown in FIG. 6.

The intensity of the light received over the measurement period (e.g., 10 ms) may be calculated by the pulse caller by summing the values representing the number of photons received in each time bin. For example, if the photodetector bins the arrival of incident photons into eight time bins, as shown in FIG. 6, the number of photons received in the eight time bins are summed to determine the intensity. However, any number of time bins may be used. If the photodetector has two time bins, the values representing the number of photons received in both time bins are summed to determine the intensity. For example, if the first time bin has 100 photons and second time bin has 50 photons, these values may be summed to determine an intensity of 150 photons. Alternatively, a separate time bin may exist for the purpose of measuring the total photon intensity.

The determination of the intensity of the light received may be performed for subsequent measurement periods in the data stream from the photodetector. For example, if the photodetector performs measurements in 10 ms periods, the intensity may be determined for each measurement period by summing the time bins in each 10 ms period. As a result, data representing the intensity of the light received over time can be determined.

Figure 7:
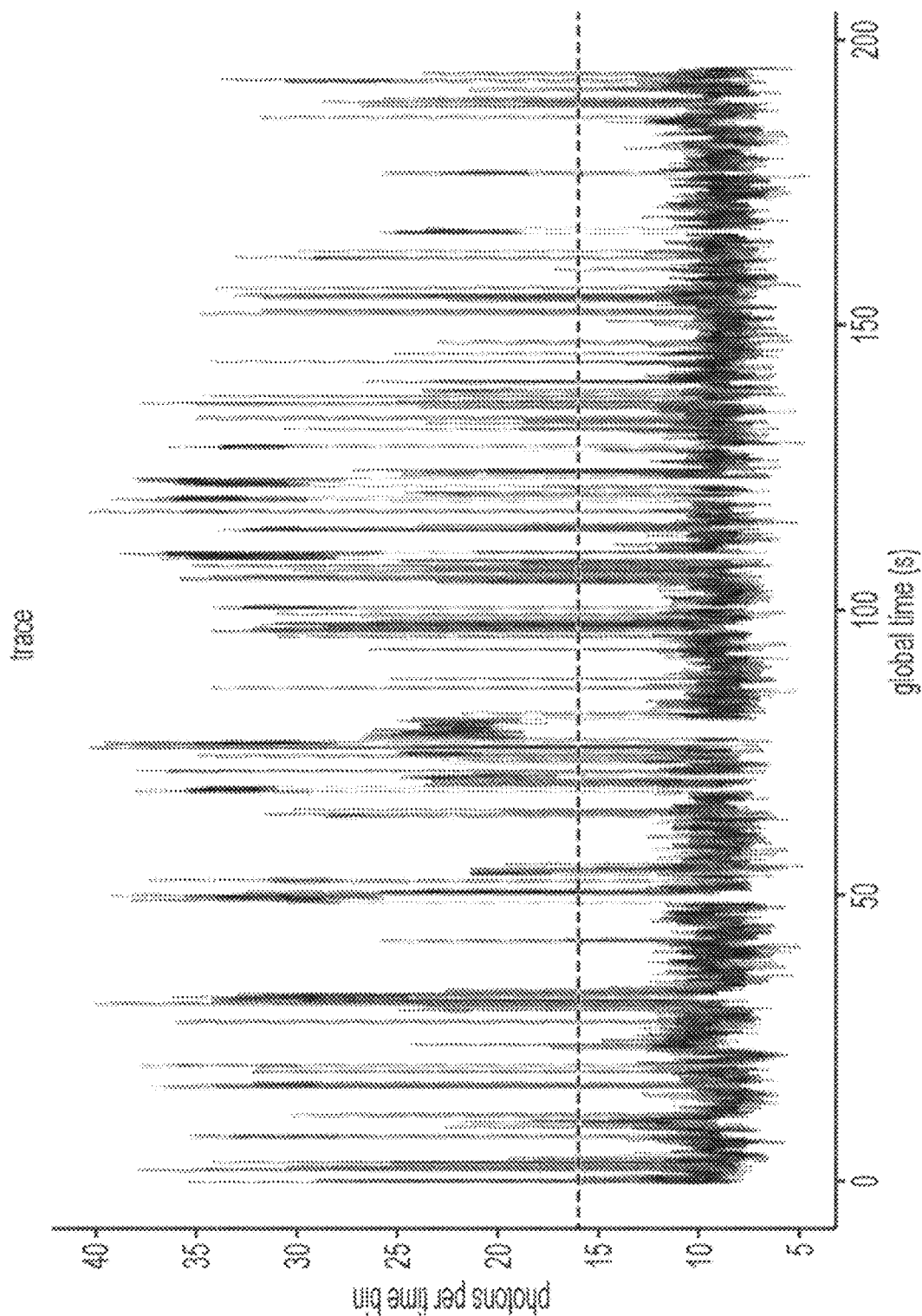
FIG. 7 is a plot of intensity of light detected by a photodetector over time during sequencing of a nucleic acid, in accordance with some embodiments of the technology described herein.

Before discussing approaches to, and embodiments for, learning enabled pulse/base calling architectures, it may be useful by way of background to consider non-learning enabled, automated approaches to identifying nucleotides from raw sensor data as obtained above. Accordingly, FIG. 7 illustrates several minutes of an example trace representing the intensity of the light received as a function of time. Because there is significant baseline and variance in the trace and true pulses often have a low signal-to-noise ratio, identifying pulses corresponding to incorporation events can be challenging. Thus, one possible approach to determining nucleotides is to run a pulse-finding algorithm on the intensity vs. time data to identify times when bursts of light are emitted corresponding to incorporation events.

More specifically, one possible approach is to run a changepoint algorithm on the trace data that determines when shifts in the mean and variance of the signal occur, e.g., when changing from background (i.e., interpulse) to signal (i.e. pulse) and vice versa. After each changepoint is identified, a threshold separates interpulse regions (regions between pulses) from pulse regions on the basis of changepoint level (e.g., intensity). This threshold can be determined manually, with histogramming, kernel density estimation, or k-means clustering. Another possible approach is to analyze the mean/median and variance of the trace, and then define pulses as increases of a certain number of standard deviations or more above the mean/median. Yet another possible approach is to use a state machine, which is either in a pulse or interpulse state, and is judged to alternate between the two. Thresholds define transitions between the two states. In some embodiments, additional filtering of called pulses may occur, such as removing pulses that do not meet a minimum or maximum duration thresholds (as very short pulses and very long pulses are often false positives). The latter two approaches have an additional benefit in that they can be operated on the data as it is being acquired, whereas a changepoint algorithm may need all of the data in order to operate.

In addition to identifying pulses corresponding to nucleotide incorporation events based on the intensity of the light emitted, other characteristics of the light emitted may be used to identify pulses in addition to, or as alternative to intensity. For example, pulses may be identified based on temporal characteristic(s) of the emitted light as an alternative to or in addition to using intensity. Different nucleotides may be labeled with molecules that emit light with different temporal characteristics, and the temporal characteristics may be analyzed to determine when incorporation events begin and end. As a specific example, different luminescent labels may have different "lifetimes" or rates at which the probability of photon emission in response to excitation decays over time. A change in the measured lifetime may indicate the start or end of an incorporation event.

In yet another approach, both intensity and temporal characteristic(s) may be used to identify the times at which incorporation events occur. As an example, changes in a temporal characteristic may be used to refine the identification of pulses based on intensity. First, intensities of light may be obtained for each incorporation event, and may be calculated by summing the time bins in each set of time bins, as discussed above. However, the intensities need not be obtained by summing the time bins, and may be measured and/or determined in a different way. Then, a pulse-finding algorithm may be run on the intensity vs. time data to identify times when bursts of light are emitted corresponding to incorporation events. Next, temporal parameter(s) for the light emitted during incorporation events is/are determined. The identified pulses may be evaluated and possibly refined based on the temporal parameter(s). For example, if a long pulse is identified (e.g., having a length greater than a threshold amount), the temporal parameter(s) of the light emitted during the pulse may be evaluated. If the temporal parameter shifts significantly during the pulse (e.g., changes by more than a threshold amount, or an amount that may indicate a different nucleotide), the initial pulse-call may be revised to identify two separate pulses instead of one long pulse. The time at which the shift in temporal parameter occurs may correspond to a temporal boundary between the two pulses. If the temporal parameter does not shift significantly during the pulse (e.g., does not change or changes by a relatively small amount), the initial pulse-call may be left unchanged. Accordingly, the results of initial pulse-calling based upon intensity can be evaluated and/or refined using temporal parameter(s).

In still other approaches, initial pulse-calling may be performed using temporal parameter(s), and pulses may be refined using intensity information. Regardless of which type of pulse-finding algorithm is implemented, the pulse caller identifies the times at which pulses corresponding to incorporation events occur. For each pulse, the pulse-caller may identify the start-time and the stop-time, the start-time and the duration, or the stop-time and the duration. The times at which such pulses occur may be analyzed to identify the luminescent label, and thus its associated nucleotide.

After performing pulse calling on a stream of data from the photodetector, a base caller algorithm may then be utilized to analyze one or more characteristics of the light for each incorporation event. In one approach, the pulse caller may pass the times at which pulses occur to the base caller. Optionally, the pulse caller may pass additional information to the base caller, such as the information regarding the number of photons received in each time bin, the calculated intensity for each measurement period, or any other suitable information. Then, intensities may be obtained for each incorporation event such as for example by summing the time bins in each set of time bins, as discussed above. Alternatively, the base caller may receive the intensities directly from the pulse caller.

An intensity may be normalized for the duration of the incorporation event identified by the pulse caller. For example, if an incorporation event lasts for twice as long as a measurement interval, the intensity may be calculated by summing the time bins for the two measurement intervals and dividing by 2. For instance, if an incorporation event last 20 ms, the measurement period is 10 ms, and photons are grouped into two time bins, the intensity may be calculated by summing the photons collected in the two time bins of the first measurement as well as the photons collected in the two time bins of the second measurement, then dividing by two. Such a calculation may also be considered to be the calculation of an average intensity over the 20 ms incorporation event.

In addition, a temporal parameter may be determined for each incorporation event. The temporal parameter may represent the decay in the probability of photon emission by a label over time following excitation. Any suitable temporal parameter may be used. For example, the luminance lifetime may be calculated by fitting an exponential to the time bins (e.g., as shown in FIG. 6), and the luminance lifetime may be used as the temporal parameter. The photon count for different time bins (or a value representative thereof) may be compared to determine a temporal parameter representing the decay in the probability of photon emission over time. For example, if the arrival of incident photons is binned into two time bins, the ratio of the photon count for the two bins may be calculated, and the ratio may be used as the temporal parameter. In one sense, the ratio of the bins may be a proxy for calculating a luminance lifetime. The ratio may be calculated in any suitable way. For example, if two time bins are used, the photon count for the time bin closest in time to the excitation event may be divided by the photon count for the second time bin to produce the ratio. The photon count of the time bins or the value representative thereof may be normalized (e.g., by the summed intensity over a set of time bins), and the normalized values may be used to determine the temporal parameter. Alternatively, the time bin with the maximum photon count may be used as the temporal parameter. To determine the time bin with the maximum photon count, the photon counts for the time bins may be compared with one another. As an example with two time bins, the photon count for a first time bin may be compared with the photon count for a second time bin. The bin with the higher photon count may be selected as a temporal parameter, and may be used for discriminating luminescent molecules. For example, one luminescent molecule may have a relatively short lifetime, which may result in the first time bin (closest in time to the excitation event) having the maximum photon count, and another luminescent molecule may have a relatively long lifetime, which may result in another time bin (farther in time from the excitation event) having the maximum photon count.

Figure 8:
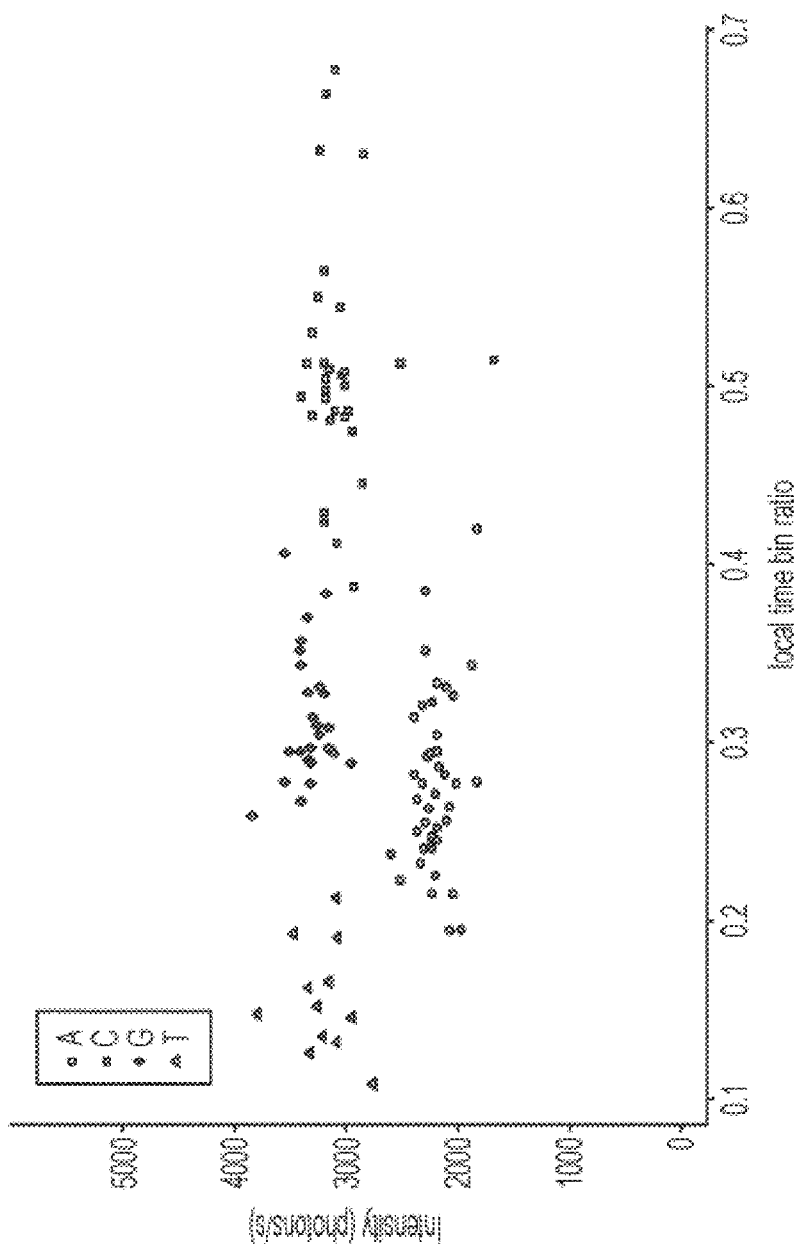
FIG. 8 is a plot of intensity versus time bin ratio as a temporal parameter for nucleotide incorporation events showing clusters of points for different nucleotides, in accordance with some embodiments of the technology described herein.

By way of further illustration, FIG. 8 is a graph depicting the intensity and temporal parameter for each incorporation event, plotted as a point in two-dimensional space, with intensity and temporal parameter being on respective axes. In this example, the temporal parameter is plotted on the horizontal (x) axis and intensity is plotted on the vertical (y) axis. Four different labels may be used for the nucleotides that can be distinguished from one another based upon the intensity, the temporal parameter, or both. As will be noted from FIG. 8, plotting the measured intensity and temporal parameter for each incorporation event results in four clusters of points corresponding to the four nucleotides A, C, G and T.

In one approach, a clustering algorithm may be run on the points to assign the points for each incorporation event to one of four clusters. For example, the clustering algorithm may perform k-means clustering of the pulses in n-dimensional space, where k is 4 (A, C, G, T), and n is the number of metrics being used for base-calling. Alternatively, more than four clusters may be assigned, that is clustering may be performed in which k is greater than 4. This may be desirable upon recognition that in some cases the clusters may not be well-resolved, and it may be advantageous to group the points into more than four clusters. In such a case, more than one cluster may be assigned to the same nucleotide. Furthermore, filtering may be performed to eliminate points that are outliers. For example, if a point has a temporal parameter and/or intensity that is outside of an expected range, it may be excluded from the clustering algorithm and/or may not be assigned to any nucleotide group.

Any suitable number of points may be provided to the clustering algorithm, such as greater than 50, greater than 100, greater than 500, etc. The result of the clustering algorithm is to group each point into one of the four (or more) clusters. In the example of FIG. 8, n=2 since two metrics, intensity and temporal parameter, are used. Thus, a two-dimensional example with intensity and time bin ratio as a temporal parameter is plotted in FIG. 8. It should be appreciated, however, other metrics may be used.

Another two-dimensional example involves obtaining both a temporal parameter and a spectral parameter, with the spectral parameter being on the vertical (y) axis of FIG. 8 rather than intensity. In this example, spectral information is obtained regarding the light emitted for each incorporation event, and used for distinguishing the nucleotides. It should also be appreciated that any number of metrics may be used, not limited to two. For example, spectral information for an incorporation event may be obtained in addition to intensity and a temporal parameter, which can be plotted as points in three-dimensional space, with intensity, temporal parameter, and spectral information being on respective axes.

After grouping the points, it may be beneficial to further refine the groups, potentially with more metrics than were used in the initial grouping step. For this purpose a support vector machine (SVM) or other supervised classifier can be used, and clustering labels may be used as initial training data. This process may be repeated, using the results from the most recent iteration of the classifier as the training for the next iteration, until it converges. Although a clustering algorithm may be used to assign points to clusters, points may be assigned to groups without using a clustering algorithm. Boundaries between groups of points may also be determined without running a clustering algorithm.

Following clustering, the clusters of points may be assigned to nucleotides. This assignment may be performed based on known characteristics of the labels. For example, in the plot of FIG. 8, it may be known that the label for a T has a high intensity and the lowest lifetime, the label for A has a low intensity and a moderate lifetime, the label for G has a high intensity and a moderate lifetime, and the label for C has the highest lifetime and a high intensity. The clusters of points may be assigned to bases using the position of the clusters relative to one another. For example, the cluster with the lowest lifetime may be assigned to T, the cluster with the highest lifetime may be assigned to C, the cluster with the lowest intensity may be assigned to A, and the remaining cluster may be assigned to G. The points in each cluster may be assigned the nucleotide of their cluster. By storing information about the time each measurement of intensity and temporal characteristic was performed, the nucleotide strand can be sequenced.

In some embodiments, the above described approaches may also be applied to instrument calibration. In some embodiments, after an initial calibration is performed, it may not be necessary to run a clustering algorithm to assign all the points to nucleotides. Instead, calibration criteria may be determined for assigning a point to a nucleotide type. For example, cluster centroids identified by performing a clustering algorithm (e.g., k-means) during calibration may be used to identify nucleotides of a nucleic acid. In some embodiments, a sequencer may be calibrated (e.g., a sequencing device) by performing clustering using data associated with known nucleotides of nucleic acids. For example, a computer system may use trace data associated with nucleotides of one or more known DNA or RNA sequences. The system may be configured to perform a clustering algorithm using the data to obtain cluster centroids that can be used to identify nucleotides. By performing the clustering algorithm with data points associated with known nucleotides, the system may obtain cluster centroids that more accurately distinguish between different nucleotides. The cluster centroids obtained from the calibration may be used for identifying unknown nucleotides. For example, the system may determine a distance (e.g., Euclidean distance) of a data point from each of the centroids determined from calibration, and identify a nucleotide for the data point based on the determined distances. For example, the nucleotide may be identified as one associated with the centroid that is closes to the data point.

Figure 9:
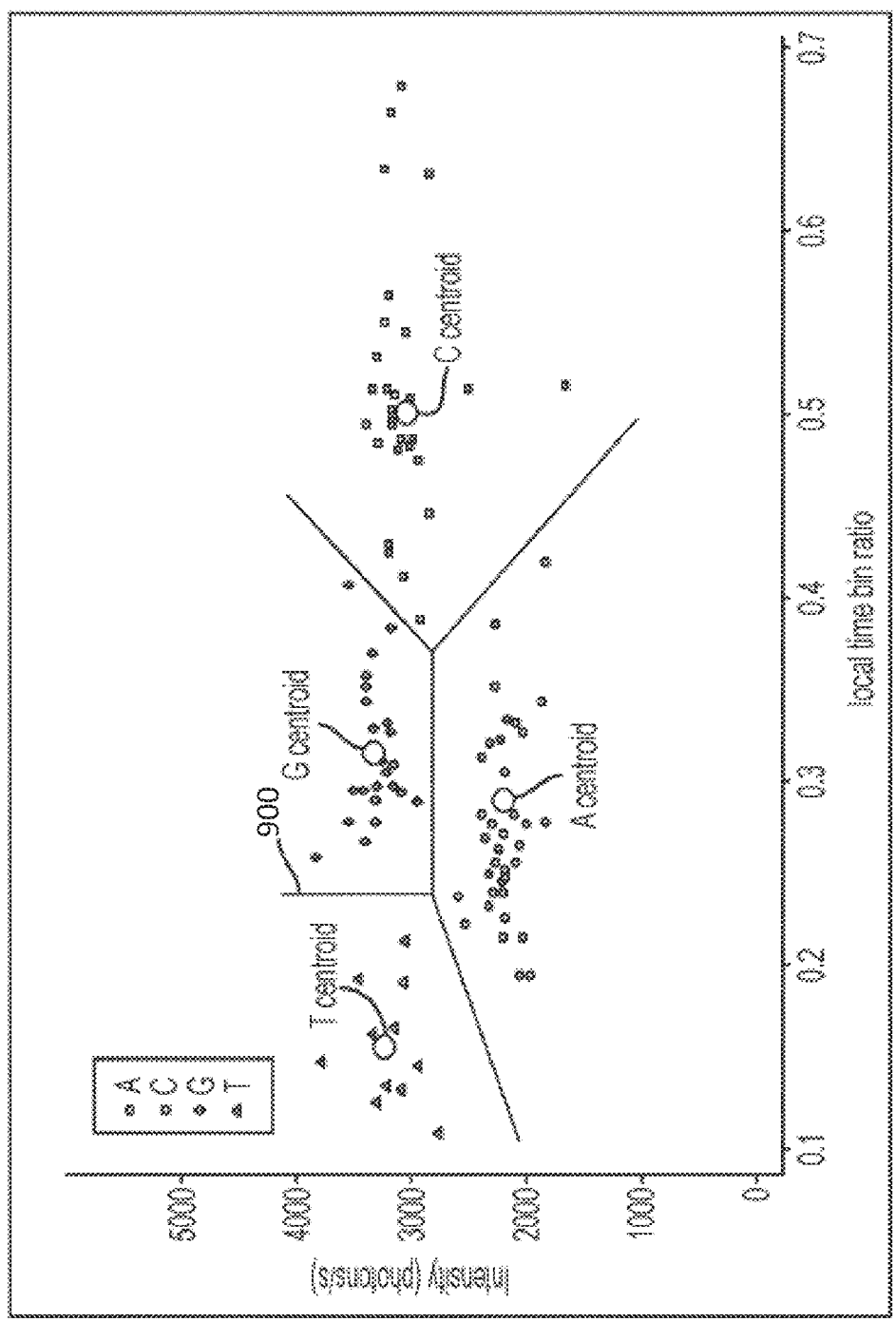
FIG. 9 is a plot showing boundaries and centroid positions for the clusters shown in FIG. 8, in accordance with some embodiments of the technology described herein.

As an example, following the clustering or the assigning of the nucleotides, boundaries between the different types of nucleotides may be determined. The boundaries may be functions defining regions of a phase space as illustrated in FIG. 9. Axes of the phase space may include intensity, temporal parameter, emission wavelength, and/or excitation wavelength of the excitation laser pulses. As an example, line segments or curves in two-dimensional space may be selected that delineate the boundaries 900 between the different nucleotides, as shown in FIG. 9. In higher-dimensional space, the boundaries may be surfaces or higher-dimensional objects (termed "hyperplanes"). Once boundaries 900 are determined, the points can be assigned to nucleotides by evaluating their positions with respect to the boundaries, and clustering need not be performed. Accordingly, in some embodiments, a sequencing instrument may be calibrated to delineate the boundaries 900. The calibration process may be performed using the same set of labels as during sequencing of a nucleic acid. As another example of performing calibration, the centroids of the clusters may be determined, which can allow assigning the points to nucleotides based on which cluster has a centroid that is closest to an individual point. Regardless of the type of calibration criteria that are determined, the calibration criteria are then stored (e.g., in a memory of the instrument) for later use.

In some embodiments, calibration of a sequencer may be performed for each individual well. A computer system may be configured to perform a clustering algorithm (e.g., k-means) for a respective well using data obtained from incorporation of nucleotides in the well. This may provide the sequencer with models that are fine-tuned to respective wells of the sequencer. In some embodiments, calibration of a sequencer may be performed for multiple wells. The system may be configured to perform a clustering algorithm using data obtained from incorporation of nucleotides in multiple wells of the sequencer. In some embodiments, the system may be configured to obtain a generalized model that may be used for the multiple wells. In some embodiments, the system may be configured to refine the generalized model for individual wells. For example, the system may modify cluster centroids of the generalized model for a respective well based on data obtained from incorporation of nucleotides in the well. Calibrating a single model for multiple wells may have the advantage of requiring less data from each individual well, and thus may require less run time to collect data to use for calibration than required for training a separate model for each individual well. Another advantage of using a generalized model is that storing a single model may require less memory than required for storing separate models for each well of a sequencer.

Calibration may be performed at any suitable time. For example, calibration may be desirable prior to first using the instrument, upon using a new set of labels, upon a change in environmental conditions in which the instrument is used, or after a period of use to account for aging of components of the instrument. The calibration may also be performed in response to a request from a user, such as by pressing a button on the instrument or sending a calibration command to the instrument from another device, or automatically based on a schedule or on an as-needed basis in response to the instrument software determining the performance is sub-optimal. Once the calibration criteria are obtained, sequencing can be performed more quickly by evaluating the detected points with respect to the calibration criteria.

Figure 10:
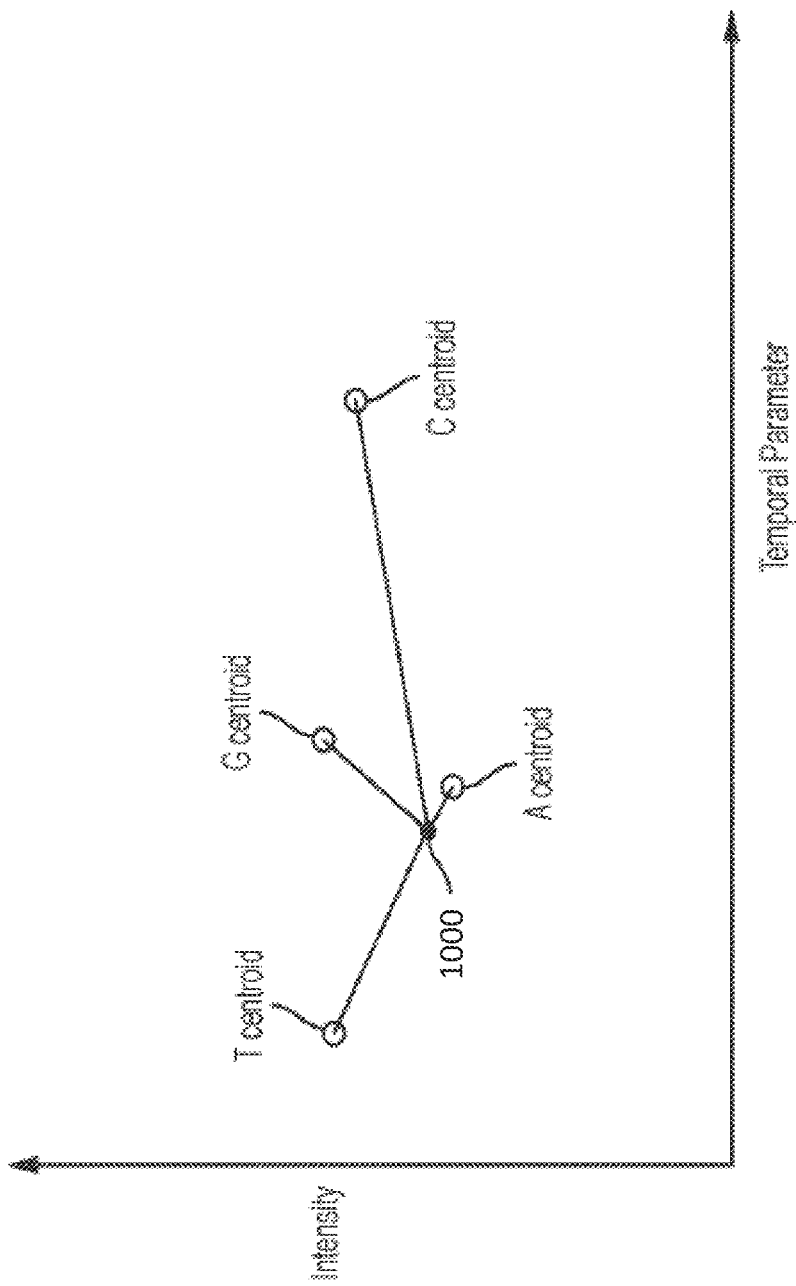
FIG. 10 is a plot of intensity versus temporal parameter illustrating relative distances of a point corresponding to a nucleotide incorporation event to centroid positions for different nucleotides, in accordance with some embodiments of the technology described herein.

More specifically, an algorithm may be used by a base caller to identify nucleotides based on one or more calibration criteria. Similar to base calling described above, the parameters of the light (e.g., intensity and a temporal parameter) are determined such that nucleotides may be identified by evaluating the measured parameters of the light (e.g., intensity and temporal parameter) using the stored calibration information. For example, if the stored calibration information includes one or more boundaries between nucleotide clusters, the points can be assigned to nucleotides by comparing the points to the boundaries, which is more computationally efficient than performing clustering. As another example, the points can be assigned to nucleotides by calculating the distance of a point to each of the four centroids of the nucleotide clusters, then assigning the point to the nucleotide with the centroid that is the closest. This technique is illustrated in FIG. 10, which shows a point 1000 representing a measured intensity and temporal parameter. Also shown in FIG. 10 are the centroids for the labels corresponding to the four nucleotides. To determine which centroid is closet, the distance from point 1000 to each of the four centroids may be calculated, and the nucleotide is assigned based on which centroid is located the shortest distance from the point 1000. As shown in the example of FIG. 10, point 1000 is closest to the centroid for the label corresponding to the nucleotide "A." Accordingly, point 1000 is determined to correspond to the nucleotide "A."

Identifying nucleotides in this manner can include performing clustering on a first portion of points associated with incorporation events and using calibration criteria to perform base calls on a second portion of points. The first portion may include any suitable number of points to provide a desired level of accuracy in the calibration criteria.

In addition, a confidence level that a point corresponds to a particular type of nucleotide may be determined. As an example, the distance of a point from a centroid of a region, such as the centroids shown in FIG. 9, may be used to determine a confidence level for the point. Points having a small distance to the centroid may have a high confidence level indicating that the point is very likely correctly identified as corresponding to a nucleotide, while points having a larger distance from the centroid, or which are barely closer to one centroid than another are less likely to be correctly identified. In this example, the confidence level may be quantified based upon the distance between the point and the centroid, or based on comparing the distance between the point and the centroid with the distance between the point and one or more other centroids. As another example, if the calibration criteria includes one or more boundaries between clusters, the confidence level may be quantified by determining the distance between the point and one or more boundaries. Points that are closer to a boundary may be given a lower confidence level. In some embodiments, the confidence level for each nucleotide identification may be stored in addition to storing the nucleotide identification itself.

The confidence level may also depend on the calibration criteria and how well the calibration criteria fit the calibration data. The more accurately the calibration criteria fit the calibration data, the higher the confidence levels may be for different points. In particular, the confidence level may depend on the time duration of the incorporation event associated with a point because the confidence level can depend on the signal-to-noise ratio of the pulse identified by the pulse caller. As an example, a long time duration may indicate that the pulse caller failed to identify two subsequent incorporation events, such as incorporation events of the same nucleotide type. In some embodiments, the base caller may communicate with the pulse caller to request that the pulse caller reevaluate the time duration of the incorporation event.

In some instances, previously-derived boundaries (e.g., an SVM model) may be applied to new pulse calls to determine the appropriate nucleotide incorporated at each pulse call event. Pulse call metrics are first scaled, then, the previously derived boundaries can be applied to classify that incorporation event. In order to derive boundaries that generalize across the pulse call data from multiple pixels, it may be necessary to scale (or normalize) each set of pulse call data from each pixel in the array prior to including those data in the calibration dataset. By scaling the intensity metric, by clustering only on intensity, and using one or more of those clusters as the mean or median of intensity, one can normalize the intensity metric of all incoming pulse calls. This scaling, or normalization, is applied both during the calibration phase, as well as during the base calling phase using the stored calibration data. This has the benefit of not requiring boundaries be generated for each pixel in the array (which is a performance improvement), and enables scaling to very large arrays where all the data may not typically fit into RAM at once. A further benefit is a reduction in runtime, since a smaller number of pulses would need to be separated by intensity and scaled or normalized to the calibration data set. This approach also allows for fewer pulses to be stored and grouped, prior to establishing the scaling or normalization factors, thus allowing outputting base calls in near real time as the data is acquired from the pixel array.

To this point, various examples for non-learning enabled, algorithmic based pulse and base calling techniques have been described, and additional information regarding the same may be found in co-pending U.S. patent application Ser. No. 15/611,573 entitled "PULSE CALLER AND BASE CALLER," filed on Jun. 1, 2017, and the contents of which are incorporated herein in their entirety. It is now further appreciated that such processes may also benefit from, and be improved by, various machine learning and/or deep learning techniques.

Accordingly, further disclosed herein are embodiments of a learning enabled base caller which, among other aspects, uses previous runs to train a model for base calling in future runs. This, in turn, may enable improvement in performance over time of deployed devices, as such deployed devices benefit from data they generate with each use. Moreover, the embodiments described herein improve base calling accuracy, which may also make standard bioinformatics applications better.

Figure 11:
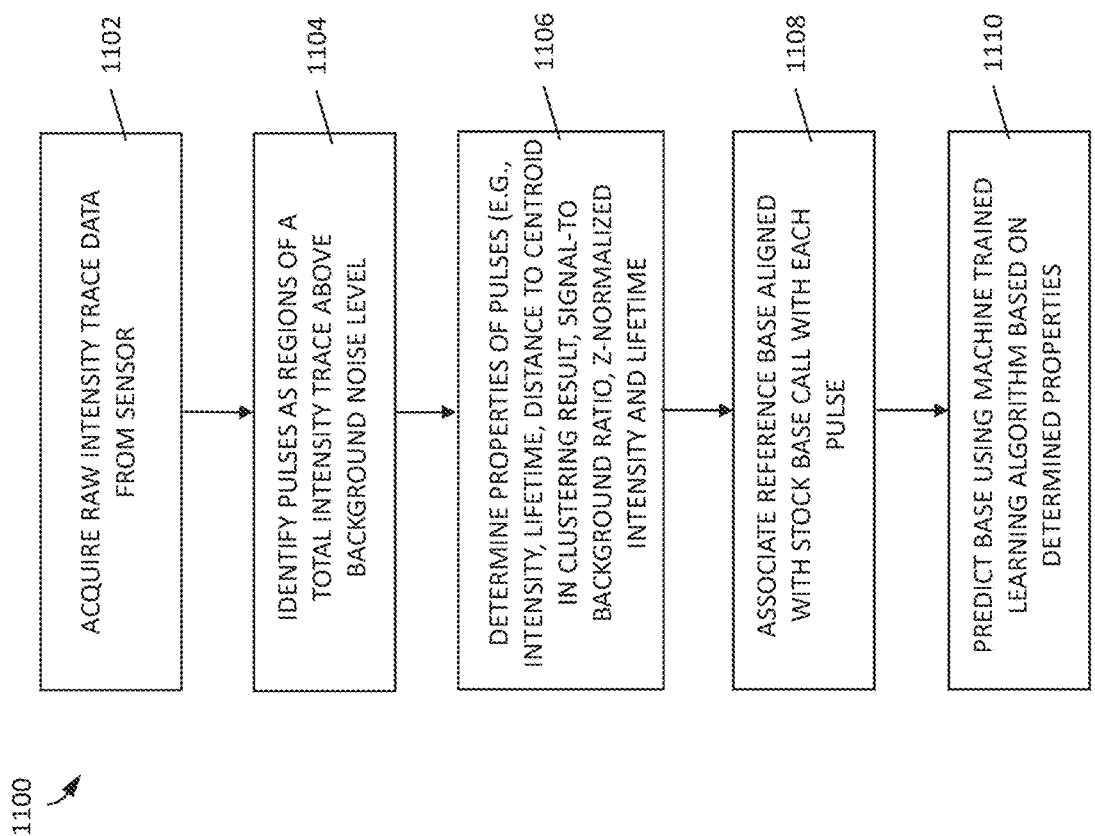
FIG. 11 is a flow diagram of a method of implementing a learning enabled base caller, according to an embodiment of the technology described herein.
Figure 12:
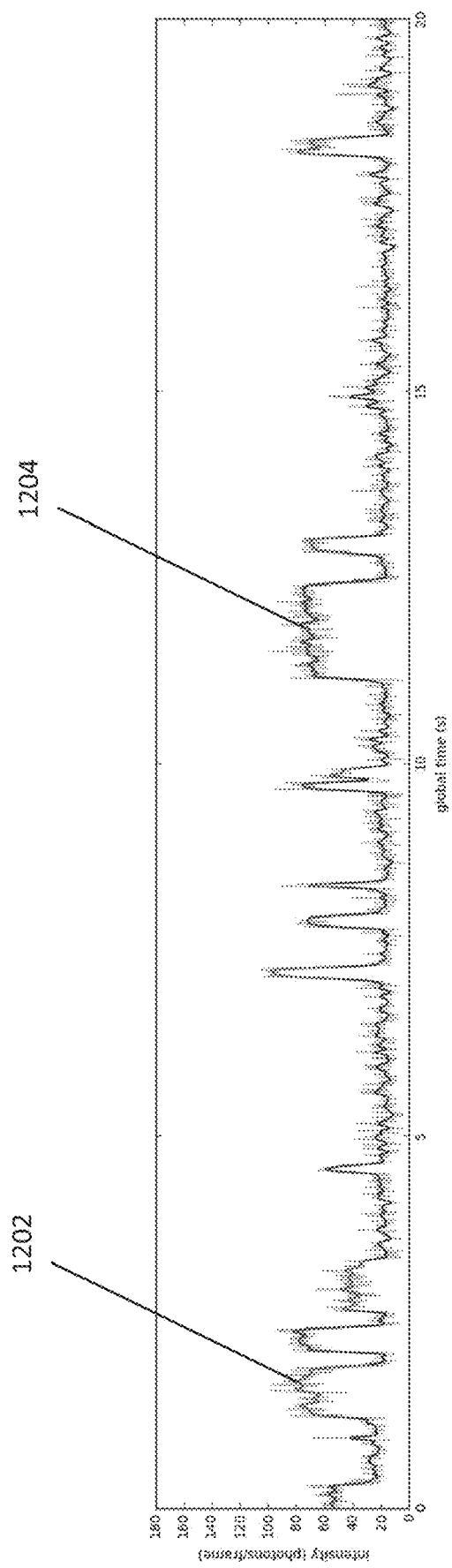
FIG. 12 is an example data trace that may be an input to the method of FIG. 11, in accordance with some embodiments of the technology described herein.

Referring now to FIG. 11, there is shown a flow diagram of a method 1100 of implementing a learning enabled base caller, according to an embodiment. As shown in FIG. 11, method 1100 begins at operation 1102 by acquisition of raw intensity trace data from a sensor. Using the raw intensity trace data, pulses may then be identified as regions of the total intensity trace above a background noise level, as indicated in operation 1104. This initial pulse calling operation may be performed in a manner similar to those techniques described above, and as illustrated for example by the trace shown in FIG. 12. Two such regions are indicated at 1202 and 1204 in FIG. 12, although it will be understood that this is not necessarily a complete annotation of all pulse regions present therein.

Figure 13:
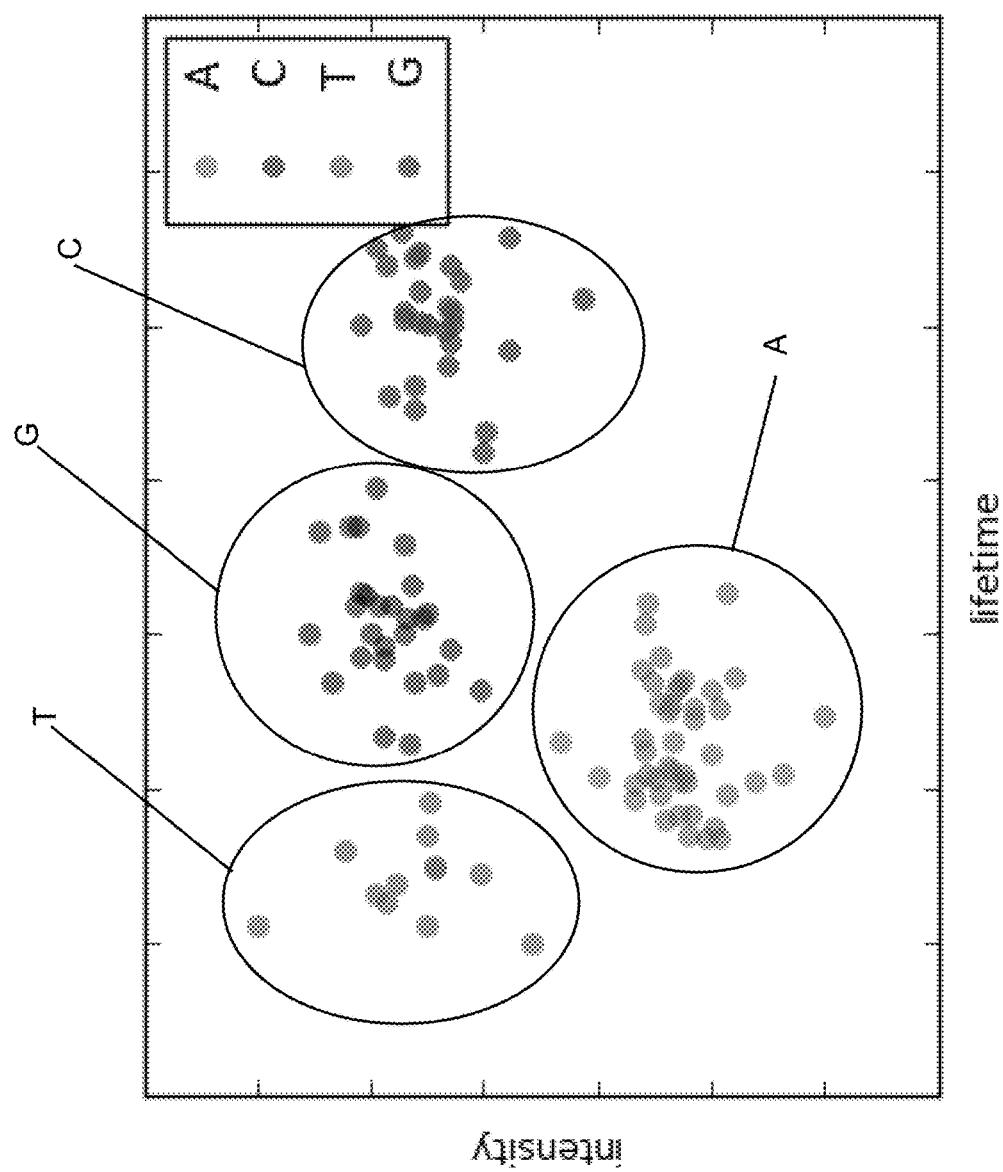
FIG. 13 is a two dimensional scatter plot of the pulse data in FIG. 12, in accordance with some embodiments of the technology described herein.

Using the pulse data, properties of the same may then be calculated or determined in order to enable base calling. As was described above, one way to process the pulse data in an unsupervised, algorithmic fashion is to calculate intensity and lifetime values and plot the resulting points in a two-dimensional scatter plot (as shown in FIG. 13 for example), and dividing the plot into four clusters to assign a base. However, in the present embodiment, other properties besides intensity and lifetime may also be used. Referring once again to FIG. 11, at operation 1106, method 1100 determines several properties of the identified pulses (e.g., intensity, lifetime, distance to each of 4 centroids in a clustering result, signal-to-background ratio, and z-normalized intensity and lifetime). Moreover, in lieu of clustering such property data in an algorithmic fashion, method 1100 then proceeds to operation 1108 to associate a reference base (that has been aligned with a stock base call) with each pulse. Then, as shown at operation 1110, a trained machine learning algorithm is used to predict a base, given the determined properties (features). It will be appreciated that the results achieved by the trained machine learning algorithm depend on the correctness of the alignments of the reference bases. Advantageously, as such an algorithm is trained on more data, it should get better at calling bases.

One noteworthy characteristic of a feature-based machine learning trained base caller such as described in conjunction with FIG. 11 is that it depends on knowing what features to extract from each pulse. Even in the case where the most important features are known (e.g., intensity and lifetime), there may be multiple ways to calculate or quantitatively determining the features (e.g., minimum values, maximum values, average values over the length of a pulse, etc.). Other aspects of a pulse trace might be summarized in ways that might be helpful to a machine learning trained algorithm, but it is conceivable that such summaries are only "guess work" at what information will actually be helpful to the algorithm. Accordingly, it may be advantageous to simply feed in the raw pulse trace values and let the algorithm determine how best to extract relevant features.

Such an approach may, for example, be implemented through the use of convolutional neural networks. For instance, in the field of image recognition (e.g., auto face-tagging on Facebook or obstacle detection for Tesla autopilot) several filters of defined height and width in pixels are scanned over an image and calculations are performed to summarize the content of each window. The use of these convolutional filters allows features to be calculated with proximal regions of the picture. A common application is face recognition, which demonstrates how deep neural networks can perform their own feature extraction. When training a net to distinguish objects, raw images are provided. One common example in this regard is distinguishing between cats and dogs. A convolutional neural network runs its filters over each of the individual images, and may thereby deduce features common to cats that distinguish them from dogs (e.g., eye shape, whiskers, etc.), though often the intermediate network representations will not be understandable by humans. Although these approaches are discussed in connection with image analysis, it should be appreciated that these techniques can be applied other types of data, including data represented as an array of values corresponding to pulse trace values generated by a photodetector. In such implementations, a convolutional neural network may be trained using sequencing data and extract features from the sequencing data that identify individual nucleotides, and the trained convolutional neural network may apply the extracted features to identify nucleotides in sequencing data, such as later acquired sequencing data.

Figures 38A, 38B:
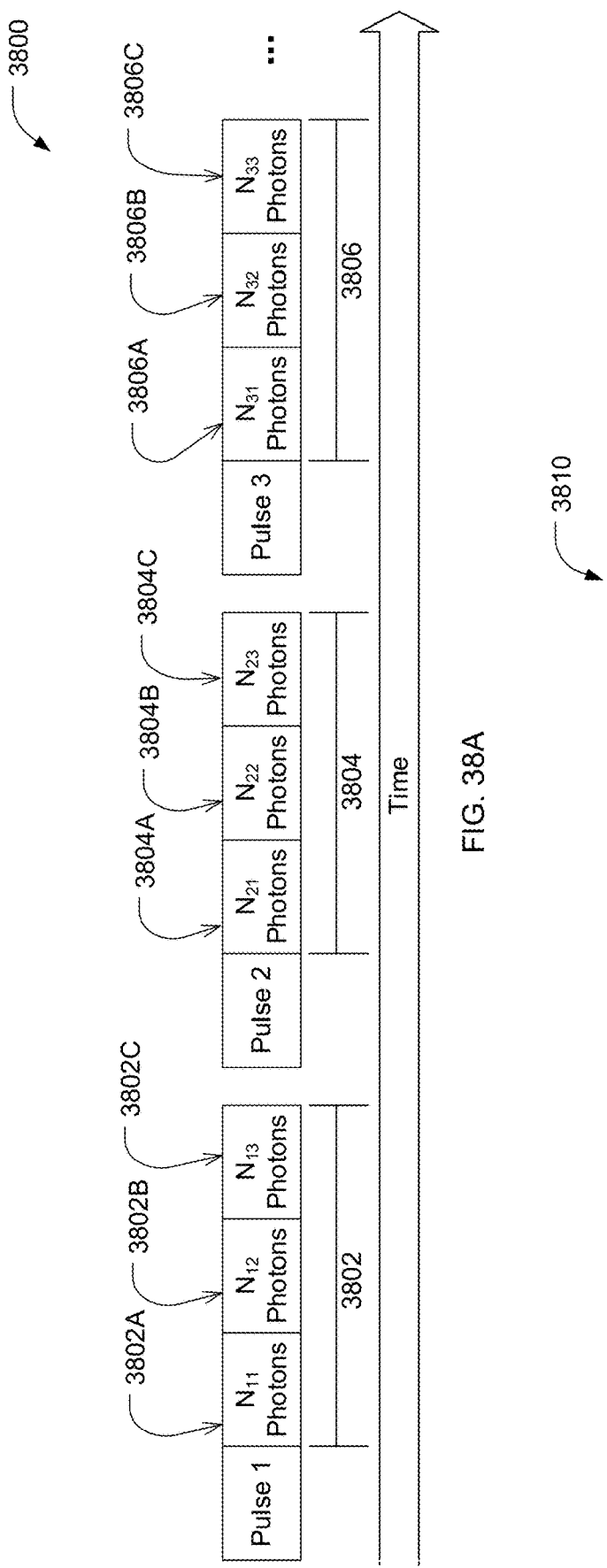
FIG. 38A illustrates exemplary data that may be obtained from nucleotide incorporation events for a nucleic acid, in accordance with some embodiments of the technology described herein.
FIG. 38B is an example data structure for arranging the data of FIG. 38A, in accordance with some embodiments of the technology described herein.

FIG. 38A illustrates an example of data 3800 that may be obtained from light emissions by luminescent labels associated with nucleotide incorporation events for a nucleic acid, in accordance with some embodiments of the technology described herein. For example, the data 3800 may be obtained by a sensor 310 of sequencing system 300 described above with reference to FIG. 3.

The data 3800 indicates a number of photons detected in each of multiple time intervals after a light pulse. A number of photons may also be referred to herein as a "photon count." In the example illustrated in FIG. 38A, the data 3800 includes numbers of photons detected (e.g., by sensor 310 of sequencing system 300) during time intervals after three pulses of light. A time interval may be referred to herein as a "bin" or a "time bin." In the example illustrated in FIG. 38A, the data 3800 includes: (1) a number of photons detected in a first time interval 3802A, a second time interval 3802B, and a third time interval 3802C of a time period 3802 after the first pulse; (2) a number of photons detected in a first time interval 3804A, a second time interval 3804B, and a third time interval 3804C of a time period 3804 after the second pulse; and (3) a number of photons detected in a first time interval 3806A, a second time interval 3806B, and a third time interval 3806C of a time period 3806 after the third pulse.

In some embodiments, each of the time intervals in a period of time after a pulse of light may be of equal or substantially equal duration. In some embodiments, the time intervals in the period of time after a pulse of light may have varying duration. In some embodiments, the data may include numbers of photons detected in a fixed number of time intervals after each pulse of light. Although the data includes three time intervals in each time period following a light pulse, the data may be binned into any suitable number of time intervals, as aspects of the technology described herein are not limited in this respect. Also, although the example of FIG. 38A shows data for three time periods following three light pulses, the data 3800 may include data collected during time periods after any suitable number of light pulses, as aspects of the technology described herein are not limited in this respect. Also, although the example of FIG. 38A shows that the intervals of a time period are disjointed, in some embodiments the intervals may overlap.

FIG. 38B illustrates an example arrangement of the data 3800 from FIG. 38A which may be provided as input to a machine learning model, according to some embodiments of the technology described herein. For example, the data structure 3810 may be generated as input to a deep learning model (e.g., a neural network) to obtain an output identifying nucleotides of a nucleic acid.

As illustrated in FIG. 38B, the numbers of photons from the data 3800 may be arranged into a data structure 3810 that includes multiple series of values. In some embodiments, the data structure 3810 may be a two-dimensional data structure encoding a matrix (e.g., an array, a set of linked lists, etc.). Each of the series of values may form a row or column of the matrix. As may be appreciated, the data structure 3810 may be considered as storing values of an image, where each "pixel" of the image corresponds to a respective time interval in a particular time period after a corresponding light pulse and the value of the pixel indicates the number of photons detected during the time interval.

In the example illustrated in FIG. 38B, the data structure 3810 includes multiple series of data in columns. Each column may also be referred to herein as a "frame." The data structure 3810 includes: (1) a first frame that specifies the numbers of photons $N_{11}$, $N_{12}$, $N_{13}$ detected in the time intervals 3802A-C of the time period 3802 after the first pulse of light; (2) a second frame that specifies the numbers of photons $N_{21}$, $N_{22}$, $N_{23}$ detected in the time intervals 3804A-C of the time period 3804 after the second pulse of light; and (3) a third frame that specifies the numbers of photons $N_{31}$, $N_{32}$, $N_{33}$ detected in the time intervals 3806A-C of the time period 3806 after the third pulse of light. Although the example illustrated in FIG. 38B shows three frames, the data structure 3810 may hold data from any suitable number of frames, as aspects of the technology described herein are not limited in this respect.

In the example illustrated in FIG. 38B, the data structure 3810 includes multiple series of data in rows. Each row specifies numbers of photons detected in a particular bin for each pulse of light. The data structure 3810 includes a first series of values that includes: (1) the number of photons ($N_{11}$) in the first interval 3802A in the time period 3802 after the first pulse of light; (2) the number of photons ($N_{21}$) in the first interval 3804A in the time period 3804 after the second pulse of light; and (3) the number of photons ($N_{31}$) in the first interval 3806A in the time period 3806 after the third pulse of light. The data structure 3810 includes a second series of values that includes: (1) the number of photons ($N_{12}$) in the second interval 3802B in the time period 3802 after the first pulse of light; (2) the number of photons ($N_{22}$) in the second interval 3804B in the time period 3804 after the second pulse of light; and (3) the number of photons ($N_{32}$) in the second interval 3806B in the time period 3806 after the third pulse of light. The data structure 3810 includes a third series of values that includes: (1) the number of photons ($N_{13}$) in the third interval 3802C in the time period 3802 after the first pulse of light; (2) the number of photons ($N_{23}$) in the third interval 3804C in the time period 3804 after the second pulse of light; and (3) the number of photons ($N_{33}$) in the third interval 3806C in the time period 3806 after the third pulse of light.

Figure 39A:
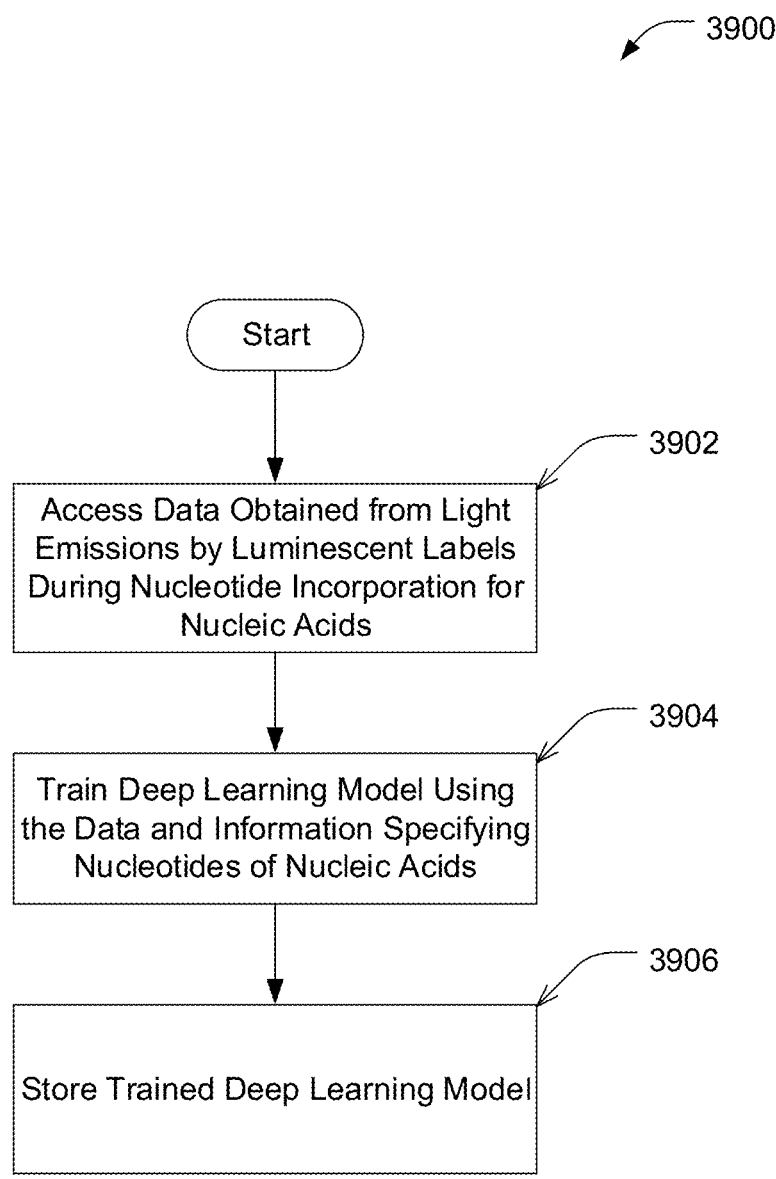
FIG. 39A is an example process for training a deep learning model for identifying nucleotides of a nucleic acid, in accordance with some embodiments of the technology described herein.

FIG. 39A illustrates an example process 3900 for training a deep learning model for identifying nucleotides of a nucleic acid, according to some embodiments of the technology described herein. Process 3900 may be performed by any suitable computer system. For example, process 3900 may be performed by workstation 108 described above with reference to FIG. 1. Process 3900 may be performed to train deep learning models described herein. For example, process 3900 may be performed to train convolutional neural network (CNN) 4000 described below in reference to FIG. 40. As another example, process 3900 may be performed to train connectionist temporal classification (CTC)-fitted neural network model 4100 described below in reference to FIG. 41.

In some embodiments, the deep learning model may be a neural network. For example, the deep learning model may be a convolutional neural network (CNN) that generates an output identifying a nucleotide for a set of data provided as input to the CNN. In some embodiments, portions of the neural network may be trained separately. For example, the deep learning model may have a first portion which encodes input data in values of one or more features. The deep learning model may include a second portion which receives the values of the feature(s) as input to generate an output identifying one or more nucleotides of a nucleic acid.

Process 3900 begins at block 3902, where the system executing process 3900 accesses training data obtained from light emissions by luminescent labels during nucleotide incorporation events for nucleic acids. In some embodiments, the data may be collected by one or more sensors (e.g., photodetector(s)) during incorporation of nucleotides into the nucleic acids by one or more sequencers. In some embodiments, the light emissions may be responsive to a series of light pulses. The data may include a number of photons detected in multiple time intervals of a time period after each of the light pulses. In some embodiments, the system may be configured to arrange the data in one or more data structures such as data structure 3810 described above with reference to FIG. 38B.

Next, process 3900 proceeds to block 3904 where the system trains a deep learning model using (1) the data accessed at block 3902; and (2) information specifying one or more nucleotides of the nucleic acids. Example deep learning models are discussed herein. In some embodiments, the information specifying one or more nucleotides of the nucleic acids may include a predetermined sequence of nucleotides for each of the nucleic acids. In some embodiments, the system may be configured to train the deep learning model by (1) providing the data accessed at block 3902 as input to the deep learning model to obtain output identifying nucleotides of the nucleic acids; and (2) training the deep learning model based on a difference between the nucleotides identified by the output and predetermined nucleotides of the nucleic acids. For example, the system may be configured to update one or more parameters of the deep learning model based on the determined difference.

In some embodiments, the system may be configured to train the deep learning model using supervised learning based on labeled training data. For example, the information specifying one or more nucleic acids may be labels for the data obtained at block 3902. In some embodiments, a portion of the data obtained at block 3902 may be provided as input to the deep learning model and the output of the deep learning model corresponding to the portion of data may be compared to a label for the portion of data. In turn, one or more parameters of the deep learning model may be updated based on the difference between the output of the deep learning model and the label for the portion of data provided as input to the deep learning model. The difference may provide a measure of how well the deep learning model performs in reproducing the label when configured with its current set of parameters. For example, the parameters of the deep learning model may be updated using stochastic gradient descent and/or any other iterative optimization technique suitable for training neural networks.

After training the deep learning model at block 3904, process 3900 proceeds to block 3906 where the system stores the trained deep learning model. The system may store value(s) of one or more trained parameters of the deep learning model. For example, the deep learning model may include one or more neural networks. The system may store values of trained weights of the neural network(s). The system may be configured to store the trained deep learning model for use in identifying nucleotides of a nucleic acid.

In some embodiments, the system may be configured to obtain new data to retrain the deep learning model. For example, the system may receive new training data (e.g., nucleic acid sequences and associated data) which the system may use to update parameters of the neural network.

In some embodiments, the system may be configured to retrain the deep learning model using one or more outputs generated by the trained deep learning model. For example, the output(s) generated by the model and corresponding input data may be used as training data. In some embodiments, the system may be configured to iteratively update the trained deep learning model using data and outputs identifying nucleic acids of nucleic acids (e.g., obtained from performing process 3910 described below in reference to FIG. 39B). For example, the system may be configured to provide input data to a first trained deep learning model (e.g., a teacher model), and obtain an output identifying one or more nucleotides of one or more nucleic acids. The system may then retrain the deep learning model using the input data and the output to obtain a second trained deep learning model (e.g., a student model).

In some embodiments, the system may be configured to train a separate deep learning model for each well of a sequencer (e.g., sequencer 304). A deep learning model may be trained for a respective well using data obtained from the well. The deep learning model may be tuned for characteristics of the well. In some embodiments, the system may be configured to train a generalized deep learning model that is to be used for identifying nucleic acids in multiple wells of a sequencer. The generalized deep learning model may be trained using data aggregated from multiple wells.

Figure 39B:
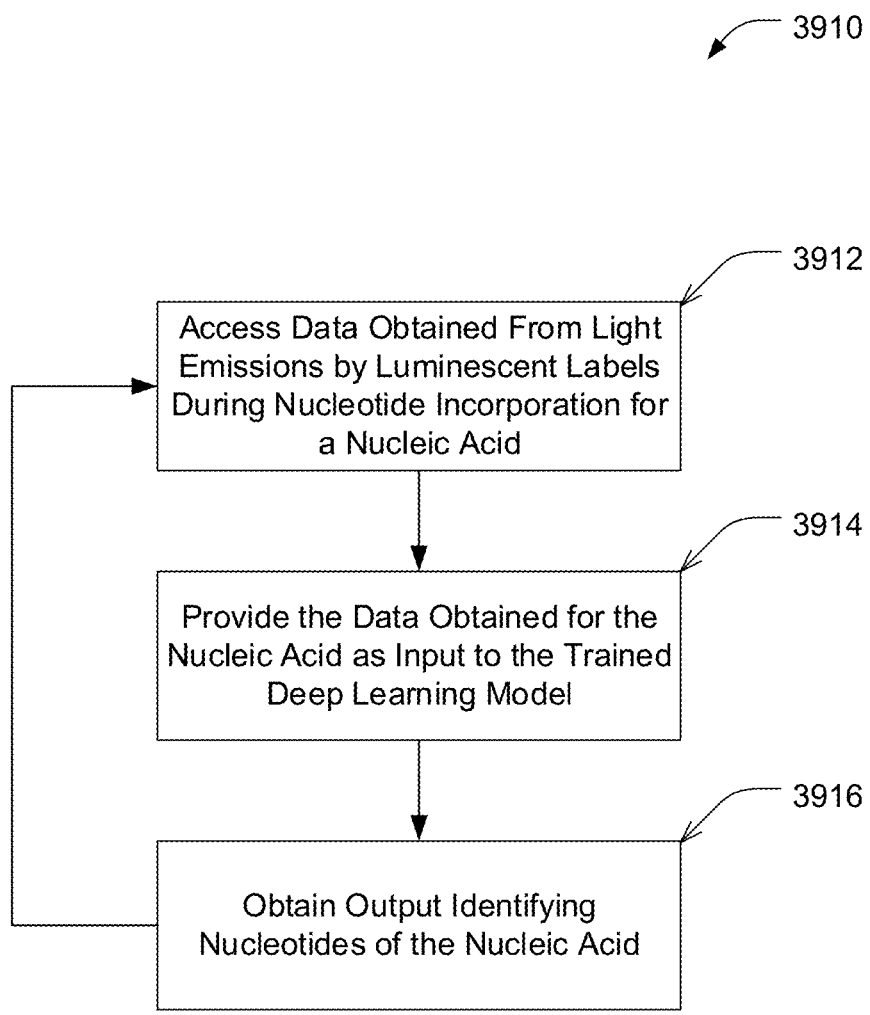
FIG. 39B is an example process for using a trained deep learning model for identifying nucleotides of a nucleic acid, in accordance with some embodiments of the technology described herein.

FIG. 39B illustrates an example process 3910 for using a trained deep learning model obtained from process 3900 for identifying nucleotides of a nucleic acid, according to some embodiments of the technology described herein. Process 3910 may be performed by any suitable computer system. For example, process 3910 may be performed by workstation 108 described above with reference to FIG. 1. Process 3910 may be performed using one or more trained deep learning models described herein. For example, process 3910 may be performed using convolutional neural network (CNN) 4000 described below in reference to FIG. 40. As another example, process 3900 may be performed using CTC-fitted neural network model 4100 described below in reference to FIG. 41.

Process 3910 begins at block 3912 where the system accesses data obtained from light emissions by luminescent labels during nucleotide incorporation events for the nucleic acid. In some embodiments, the data may be obtained from data collected by one or more sensors (e.g., photodetector(s)) during incorporation of nucleotides into the nucleic acid by a sequencer. In some embodiments, the light emissions may be responsive to a series of light pulses. The data may include a number of photons detected in multiple time intervals of a time period after each of the light pulses. For example, the data may be data 3800 described above with reference to FIG. 38A. In some embodiments, the system may be configured to arrange the data into a data structure 3810 described above with reference to FIG. 38B.

Next, process 3900 proceeds to block 3912 where the system provides the data accessed at block 3906 as input to the trained deep learning model. In some embodiments, the system may be configured to divide the data into multiple time periods and provide the data for each of the time periods as a series of inputs to the trained deep learning model to obtain a corresponding output for each input. For example, the system may provide each portion of the data as input to CNN 4000, and obtain an output identifying a nucleotide for the portion of data. In some embodiments, the system may be configured to provide the data as input without dividing it up by time period, and obtain an output identifying nucleotides of the nucleic acid. For example, the system may provide the data obtained at block 3912 as input to the CTC-fitted neural network model 4100, and obtain an output identifying a sequence of nucleotides of the nucleic acid.

Next, process 3900 proceeds to block 3916 where the system obtains an output identifying nucleotides of the nucleic acids. In some embodiments, the system may be configured to obtain an output for each of multiple time periods. The output may indicate a nucleotide incorporated into the nucleic acid during the time period. For example, the output may be values indicating probabilities of various nucleotides being incorporated into the nucleic acid during the timer period. In some embodiments, the system may be configured to obtain a single output identifying the nucleotides of the nucleic acid. For example, the system may receive a sequence of letters identifying the nucleotides of the nucleic acid. As another example, the system may receive a series of probabilities for each nucleotide. The system may be configured to use the probabilities to identify the nucleotides of the nucleic acid.

After obtaining the output from the trained deep learning model identifying nucleotides of the nucleic acid at block 3910, process 3900 returns to block 3912 where the system begins performing process 3910 again to identify nucleotides of another nucleic acid.

Figure 14:
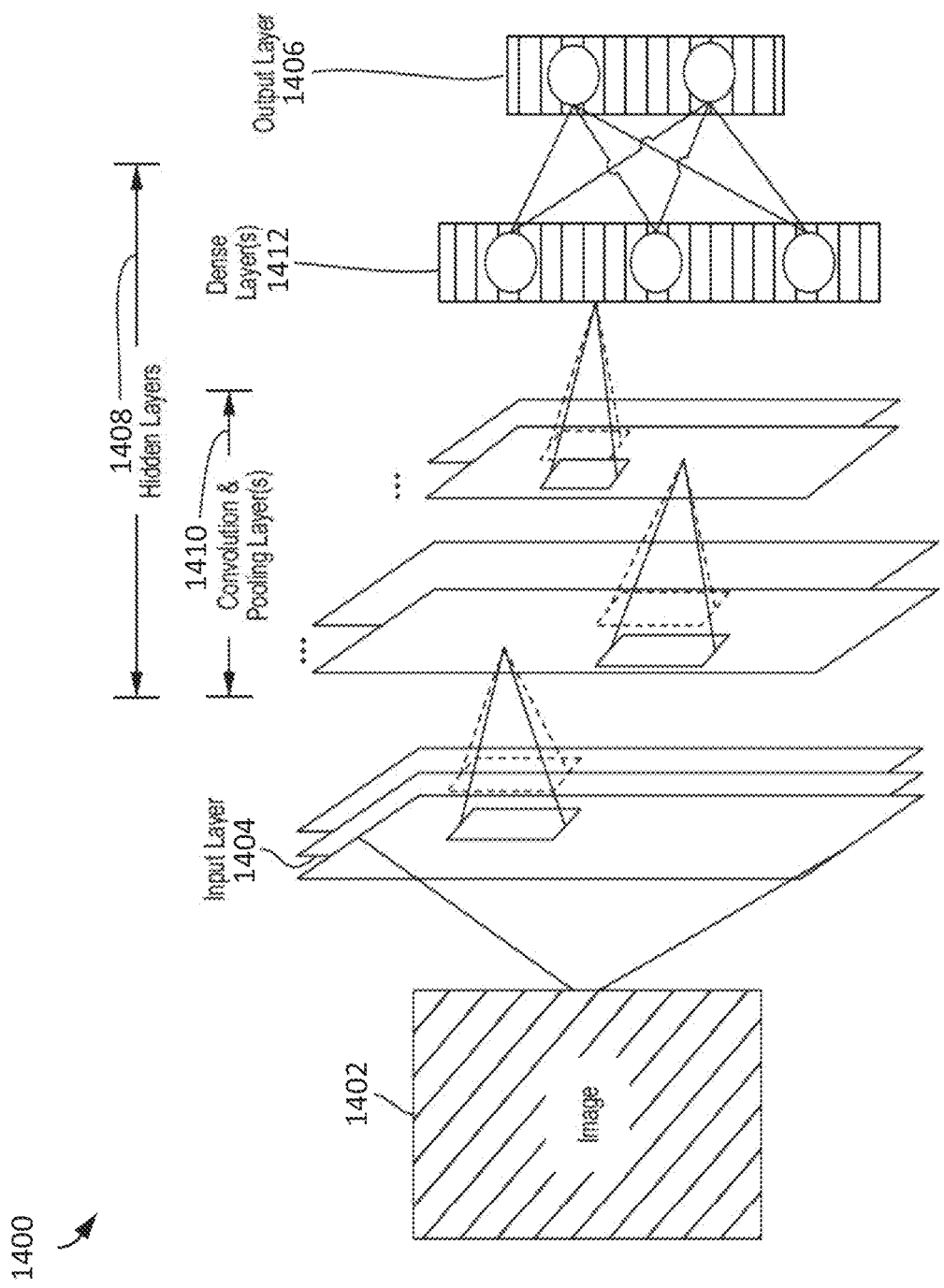
FIG. 14 is a schematic diagram illustrating layers of an exemplary convolutional neural network that is configured to analyze an image, in accordance with some embodiments of the technology described herein.

By way of further illustration, FIG. 14 is a schematic diagram illustrating layers of an exemplary convolutional neural network 1400 that is configured to analyze an image 1402. As shown, the convolutional neural network includes an input layer 1404 to receive the image 1402, an output layer 1406 to provide the output, and a plurality of hidden layers 1408 connected between the input layer 1404 and the output layer 1406. The plurality of hidden layers 1408 includes convolution and pooling layers 1410 and dense layers 1412.

The input layer 1404 may receive the input to the convolutional neural network 1400, which input to may be the image 1402. Image 1402 may have a matrix of values, such as a 2×N matrix of photon counts from two bins. Further, the input layer 1404 may be followed by one or more convolution and pooling layers 1410. A convolution layer may comprise a set of filters that are spatially smaller (e.g., have a smaller width and/or height) than the input to the convolution layer (e.g., the image 1402). Each of the filters may be convolved with the input to the convolution layer to produce an activation map (e.g., a 2-dimensional activation map) indicative of the responses of that filter at every spatial position. The convolution layer may be followed by a pooling layer that down-samples the output of a convolution layer to reduce its dimensions.

The convolution and pooling layers 1410 may be followed by dense layers 1412. The dense layers 1412 may comprise one or more layers each with one or more neurons that receives an input from a previous layer (e.g., a convolutional or pooling layer) and provides an output to a subsequent layer (e.g., the output layer 1406). The dense layers 1412 may be described as "dense" because each of the neurons in a given layer may receive an input from each neuron in a previous layer and provide an output to each neuron in a subsequent layer. The dense layers 1412 may be followed by an output layer 1406 that provides the output of the convolutional neural network. The output may be, for example, an indication of which class (e.g., a type of nucleotide), from a set of classes (e.g., different nucleotides), the image 1402 (or any portion of the image 1402) belongs to. In the context of nucleic acid sequencing, a class may correspond to a particular type of nucleotide (e.g., A, G, T, C).

It should be appreciated that the convolutional neural network 1400 shown in FIG. 14 is only one example implementation and that other implementations may be employed. For example, one or more layers may be added to or removed from the convolutional neural network shown in FIG. 14. Additional example layers that may be added to the convolutional neural network include: a rectified linear units (ReLU) layer, a pad layer, a concatenate layer, and an upscale layer. An upscale layer may be configured to upsample the input to the layer. An ReLU layer may be configured to apply a rectifier (sometimes referred to as a ramp function) as a transfer function to the input. A pad layer may be configured to change the size of the input to the layer by padding one or more dimensions of the input. A concatenate layer may be configured to combine multiple inputs (e.g., combine inputs from multiple layers) into a single output.

Figure 15:
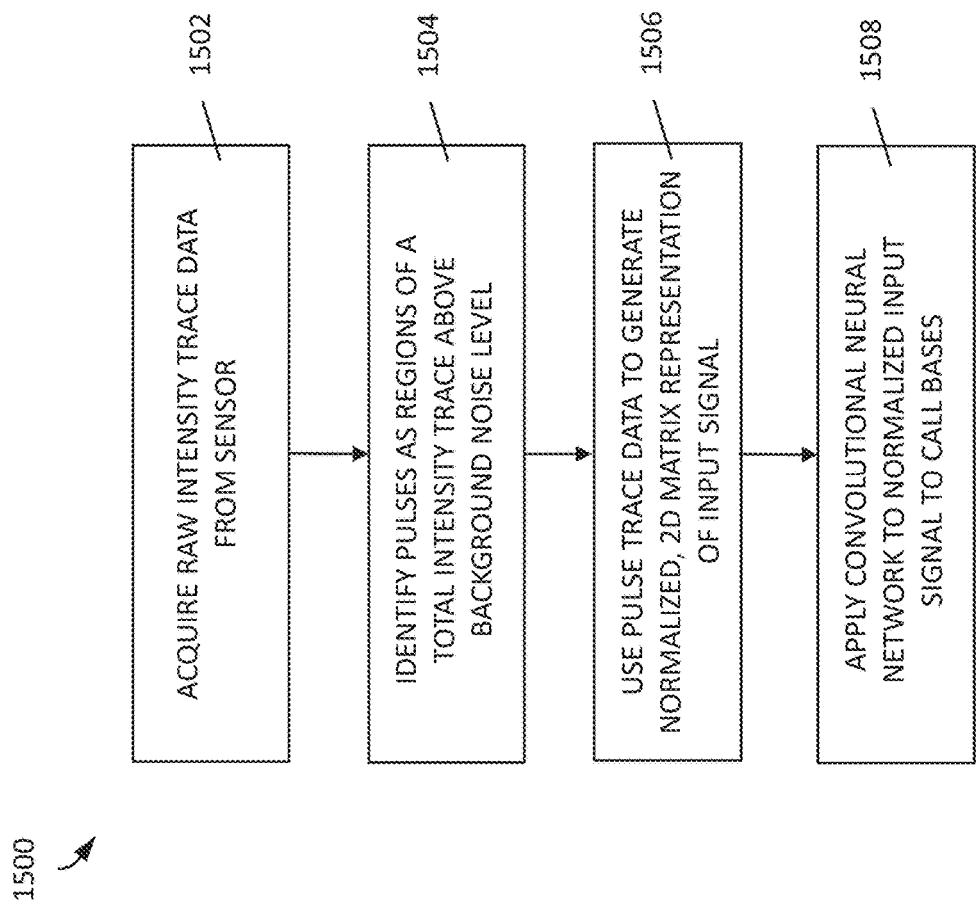
FIG. 15 is a flow diagram illustrating a method of implementing a learning enabled base caller, in accordance with some embodiments of the technology described herein.

With respect to base calling, FIG. 15 is a flow diagram illustrating a method 1500 of implementing a learning enabled base caller, according to another embodiment. Instead of determining and/or calculating specific properties of pulse trace data, the data is instead analyzed and treated in a manner similar to images, and fed to a convolutional neural network (e.g., network 1400 in FIG. 14) using four classes (A, T, C, G) of lower dimensional data; namely, photon counts in first and second time bins over a length of time. As shown in FIG. 15, method 1500 begins at operation 1502 by acquisition of raw intensity trace data from a sensor. Using the raw intensity trace data, pulses may then be identified as regions of the total intensity trace above a background noise level, as indicated in operation 1504. Notably, operations 1502 and 1504 may be respectively similar to operations 1102 and 1104 of FIG. 11, and in addition, the initial pulse calling operation may be performed in a manner similar to those techniques described above, and as illustrated for example by the trace shown in FIG. 12.

In operation 1506, the pulse trace data is normalized in order to generate a normalized, 2D matrix representation of the input signal, to be applied to a convolutional neural network (e.g., network 1400 in FIG. 14) for base calling as shown in operation 1508. With respect to normalization of the input signal it is contemplated that several approaches may be used to translate the raw traces to a normalized range. For example, normalization may take place linearly between 0 and 1, between −1 and 1, by counting the number of standard deviations from the mean (z-score) over all measurements in a trace, or any combination of these strategies (e.g., by first transforming via z-score and then scaling to the range −1 to 1). By way of further illustration, FIGS. 16A-16D are examples of the four classes (A, T, C, G, respectively) of lower dimensional data, each using first and second photon counts (time bin 1, time bin 2) over a length of time. More specifically, FIG. 16A illustrates four examples of normalized 2D matrix representations of pulse trace data (similar to images) characteristic of base signature A; FIG. 16B illustrates four examples of normalized 2D matrix representations of pulse trace data characteristic of base signature T; FIG. 16C illustrates four examples of normalized 2D matrix representations of pulse trace data characteristic of base signature C; and FIG. 16D illustrates four examples of normalized 2D matrix representations of pulse trace data characteristic of base signature G. The 2D matrix representation of pulse trace data may be considered as stacked vectors, where individual vectors correspond to different time bins of the photodetector and values in a vector correspond to photon counts over time. Applying convolution filter(s) of the neural network to the 2D matrix representation may involve passing one or more convolution filters along the time dimension, such as for individual time bins, and/or across different vectors, such as for values for different time bins that correspond to the same time. In embodiments that involve normalizing the 2D matrix representation, normalization may involve scaling a vector based on the minimum value and/or maximum value in the vector, which may account for different parameters (e.g., laser power used across different sequencing runs) used in obtaining the sequencing data such that the resulting normalized data is within a range of values.

Figures 17A, 17B, 17C, 17D:
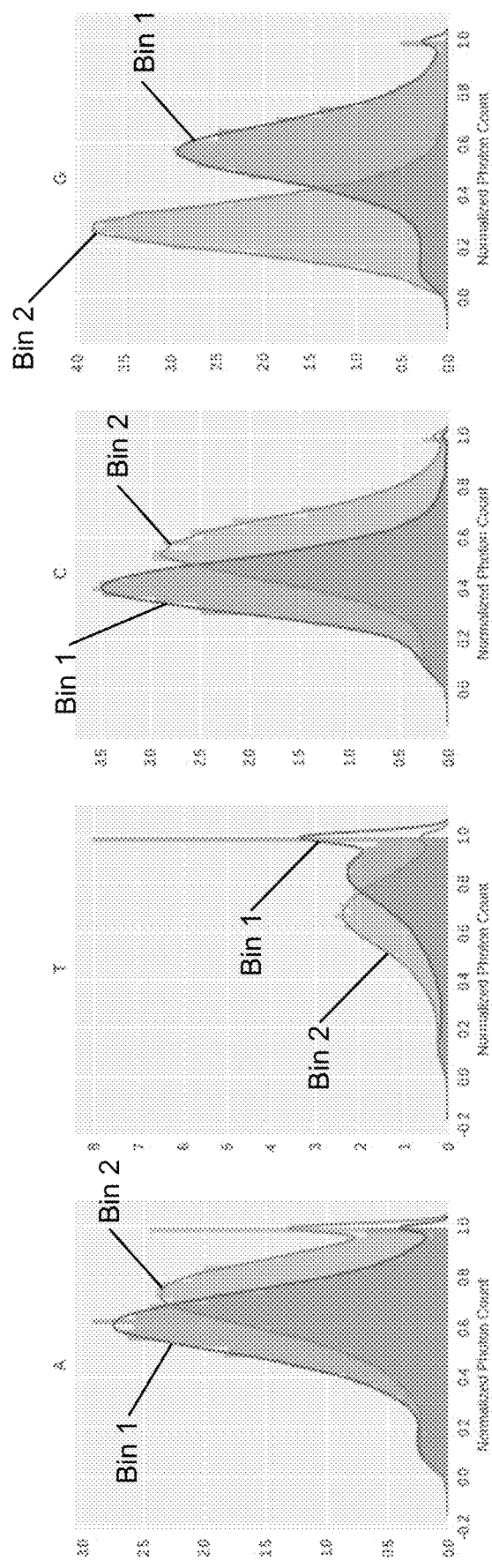
FIGS. 17A-17D illustrate shown a series of normalized time bin and time bin photon counts for each of the base signatures, in accordance with some embodiments of the technology described herein.

Referring now to FIGS. 17A-17D, there is shown a series of normalized time bin 1 and time bin 2 photon counts for each of the base signatures, wherein FIG. 17A illustrates a normalized photon count distribution for base signature A; FIG. 17B illustrates a normalized photon count distribution for base signature T; FIG. 17C illustrates a normalized photon count distribution for base signature C; and FIG. 17D illustrates a normalized photon count distribution for base signature G. FIGS. 17A, 17B, 17C, and 17D represent a summary of photon counts across all traces for each of the different nucleotides and are derived from data, including the data shown in FIGS. 16A, 16B, 16C, and 16D. As will be noted, that the distributions of normalized time bin 1 and time bin 2 photon counts reflect distinguishable base signatures. Although there are overlaps between the bins in these distributions calculated across many apertures, it will be noted that the individual pulse traces FIGS. 17A-17D typically maintain a good separation between these values that move up and down in absolute photon count in unison. Thus, they are likely signatures that can be learned by a convolutional neural network, particularly given that the trends are fairly easily by the human eye (which in turn is a good indicator that a DL algorithm will perform well).

With respect to the learning-enabled base calling embodiment in FIG. 11, the convolutional neural network "image" approach may have a higher performance ceiling and, as such, would benefit more from large amounts of raw data. That is, more data may be needed to train a convolution model because the algorithm not only has to learn how to predict labels, it also has to learn representations of features themselves. In a feature-based model, a trainer may feed the model features known to be informative, so therefore only labels need to be learned, thus using less data. On the other hand, a convolution-based DL model may be able to learn "better" features than human trainers can calculate up front, given enough data.

In sum, a deep-learning base calling algorithm featuring convolution neural nets may be used to perform a task somewhat similar to facial recognition techniques in order to identify bases in dual photon time bin space. This solution may be applied to raw pulse data by preprocessing the traces to extract pulse events and feeding a static snapshot of each pulse, cropped out of the trace, into an "image processing" neural network.

To this point, each of the above described automated pulse and base calling approaches (including those employing deep learning techniques and convolutional neural networks) have first incorporated some manner of pulse calling or pulse identification from the raw sensor data prior to base calling. Accordingly, further approaches described herein provide embodiments for performing pulse and base calling all in one step. This may allow, for example, a neural net to learn how to call pulses aided by information of what a pulse from each base (A, C, T, G) "looks" like. Such an approach may further help to eliminate any spurious flickers that cross a given intensity threshold, but that are not characteristic of a base.

Figure 18:
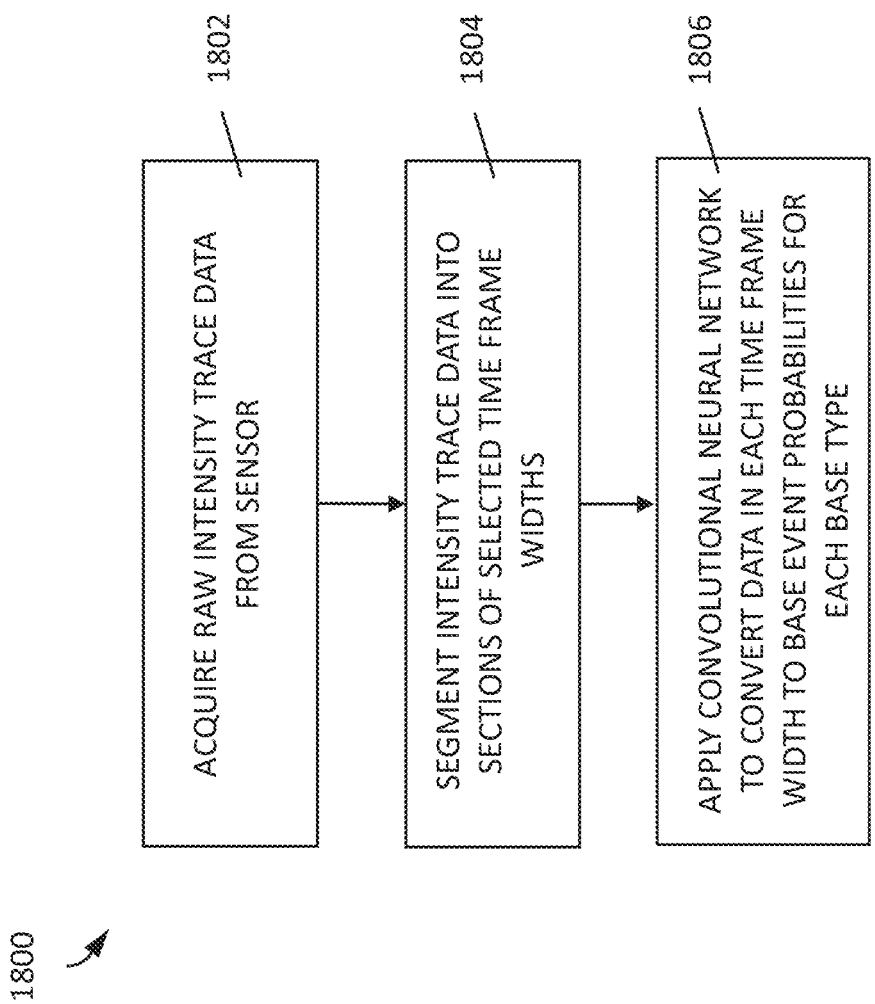
FIG. 18 is a flow diagram illustrating a method of implementing a learning enabled base caller, in accordance with some embodiments of the technology described herein.

Referring now to FIG. 18, there is shown a flow diagram illustrating a method 1800 of implementing a learning enabled base caller, according to another embodiment. Generally, a base calling convolutional neural network is applied directly to longer traces. Similar to previous embodiments, method 1800 begins at operation 1802 by acquisition of raw intensity trace data from a sensor. Because a neural network expects a certain "image" shape as input (e.g., the network is trained to recognize bases in a certain number of frame chunks), method proceeds to operation 1804 to first segment the intensity trace data into selected time frame width. In one embodiment, the data may be portioned into 50-frame chunks, although it should be appreciated that a greater or lesser number of frame chunks may be used. Then, within a given frame width, method 1800 applies a convolutional neural network at operation 1806 to convert the data into a running probability across the time domain of a base event for each base type.

Figure 40:
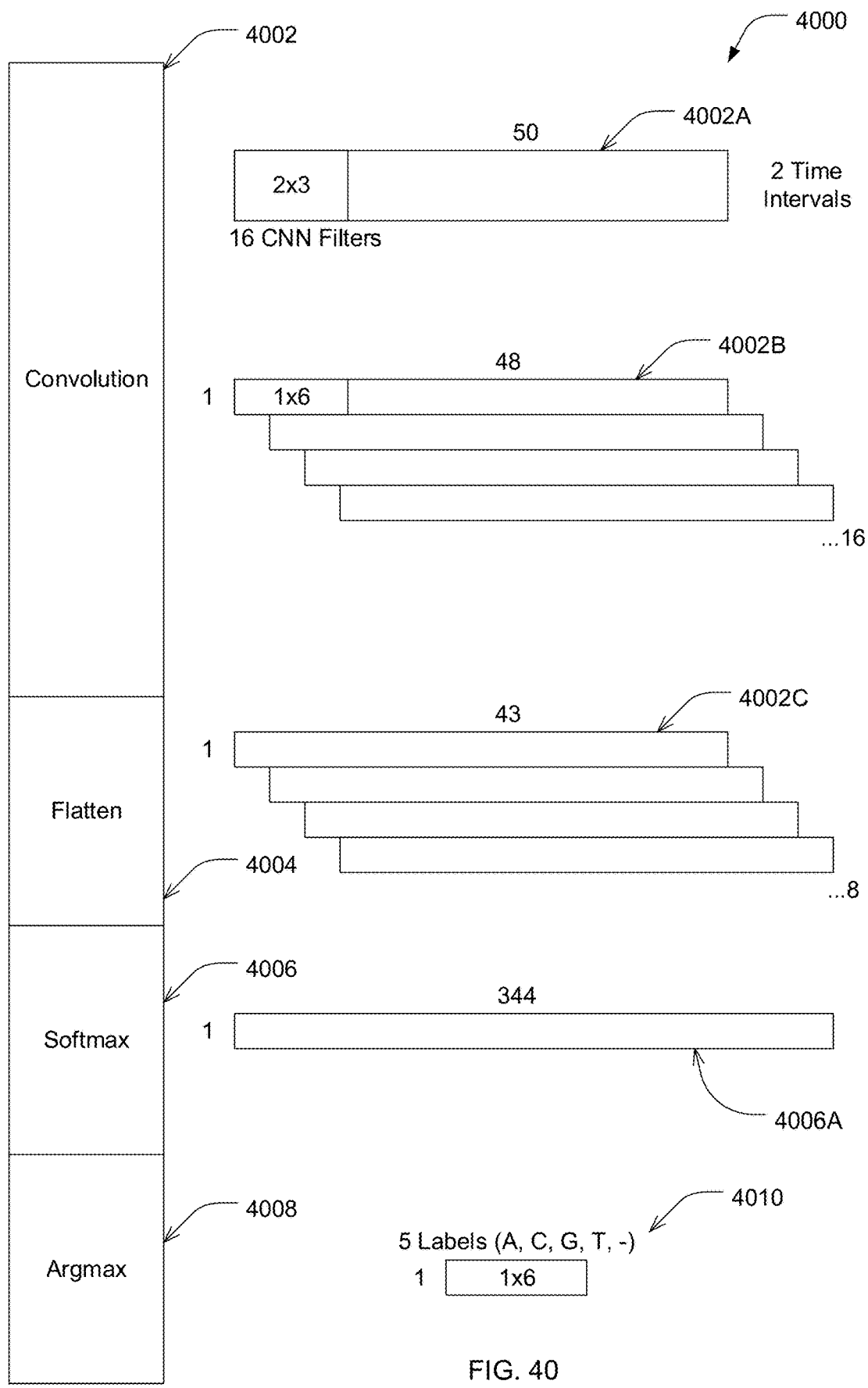
FIG. 40 is a structure of an exemplary convolutional neural network (CNN) for identifying nucleotides of a nucleic acid, in accordance with some embodiments of the technology described herein.

FIG. 40 illustrates an example structure of a convolutional neural network (CNN) 4000 for identifying nucleotides of a nucleic acid, according to some embodiments of the technology described herein. In some embodiments, the CNN 4000 may be trained by performing process 3900 described above with reference to FIG. 39A. In some embodiments, the trained CNN 4000 obtained from process 3900 may be used to perform process 3910 described above with reference to FIG. 39B. In some embodiments, the convolutional neural network 4000 may be used in process 1800 described above with reference to FIG. 18.

In the example embodiment of FIG. 40, the CNN 4000 receives an input 4002A. In some embodiments, the input 4002A may be a collection of frames specifying numbers of photons in time intervals of time period after light pulses. In some embodiments, the input 4002A may be arranged in a data structure such as data structure 3810 described above with reference to FIG. 38B. In the example embodiment of FIG. 40, the input 4002A includes 50 frames of data for two time intervals forming a 2×50 input matrix.

In some embodiments, the CNN 4000 includes one or more convolutional layers 4002 in which the input 4002A is convolved with one or more filters. In the example embodiment of FIG. 40, the input 4002A is convolved with a first series of 16 2×3 filters in a first convolution layer. The convolution with 16 filters results in an 16×48 output 4002B. In some embodiments, the CNN 4000 may include a pooling layer after the first convolutional layer. For example, the CNN 4000 may perform pooling by taking the maximum value in windows of the output of the first convolutional layer to obtain the output 4002B.

In the example embodiment of FIG. 40, the output 4002B of the first convolutional layer is then convolved with a second set of one or more filters in a second convolution layer. The output 4002B is convolved with a set of one or more 1×6 filters to obtain the output 4002C. In some embodiments, the CNN 4000 may include a pooling layer (e.g., a max pooling layer) after the second convolutional layer.

In the example embodiment of FIG. 40, the CNN 4000 includes a flattening step 4004 in which the output of the convolution 4002 is flattened to generate a flattened output 4006A. In some embodiments, the CNN 4000 may be configured to flatten the output 4002C by converting an 8×43 output matrix into a one dimensional vector. In the example embodiment of FIG. 40, the 8×43 output 4002C is converted into a 1×344 vector 4006A. The vector 4006A may be inputted into a fully connected layer to generate a score for each possible class. In the example embodiment of FIG. 40, the possible classes are the nucleotides Adenosine (A), Cytosine (C), Guanine (G), and Thymine (T), and blank (-). A softmax operation 4006 is then performed on the output of the fully connected layer to obtain the output 4010. In some embodiments, the softmax operation 4006 may convert the score for each of the classes into a respective probability. An argmax operation 4008 is then performed on the output 4010 to obtain a classification. The argmax operation 4008 may select the class having the highest probability in the output 4010. For example, the output may identify a nucleotide (e.g., A, C, G, or T) that was incorporated during a time period represented by the input 4002A. As another example, the output may identify that no nucleotide was incorporated into the nucleic acid during the time period by outputting a classification of blank (-).

Figure 19:
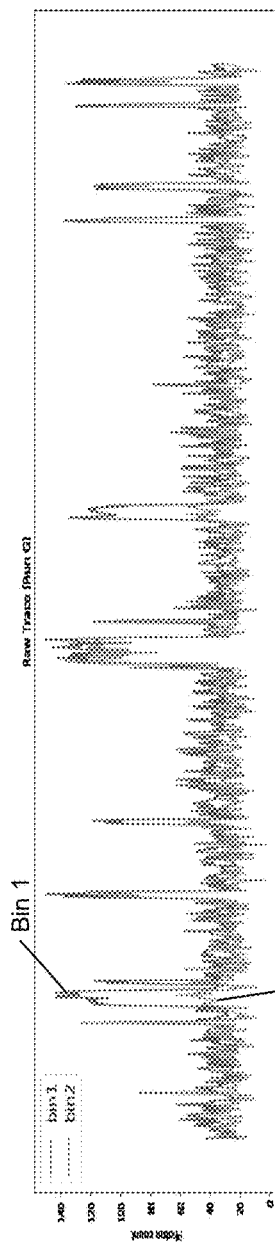
FIG. 19 is a plot that shows an example of raw trace of time bin 1 and time bin 2 photon counts used by the method of FIG. 18, in accordance with some embodiments of the technology described herein.
Figure 20A:
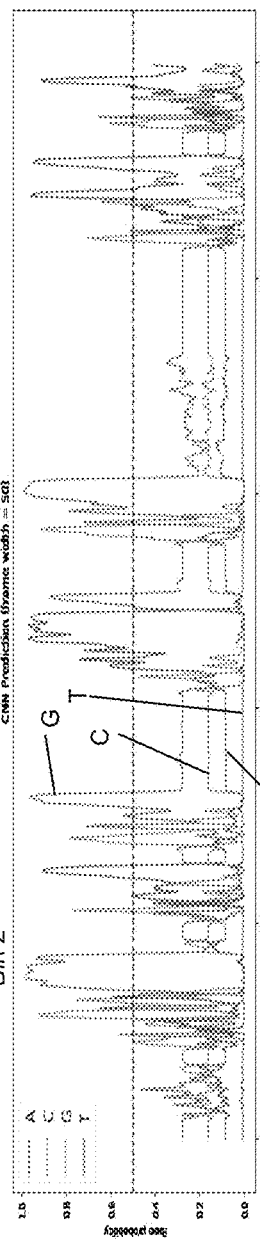
FIGS. 20A-20C are plots that show running base count probabilities produced by inputting the raw trace data of FIG. 19 to a convolutional neural network applied over different-sized windows, in accordance with some embodiments of the technology described herein.
Figure 20B:
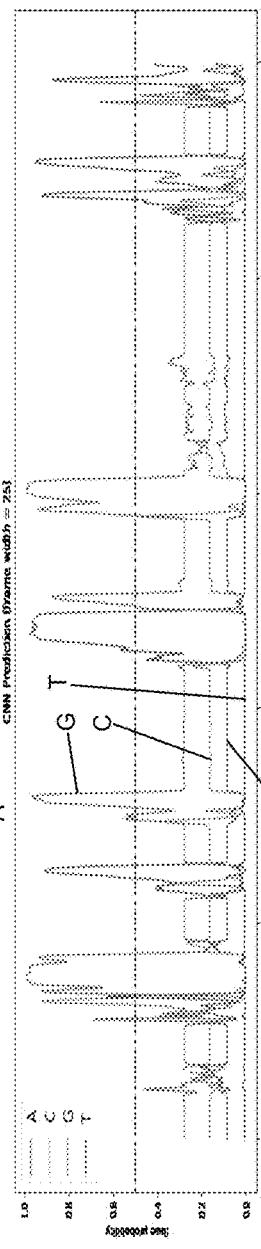
Figure 20C:
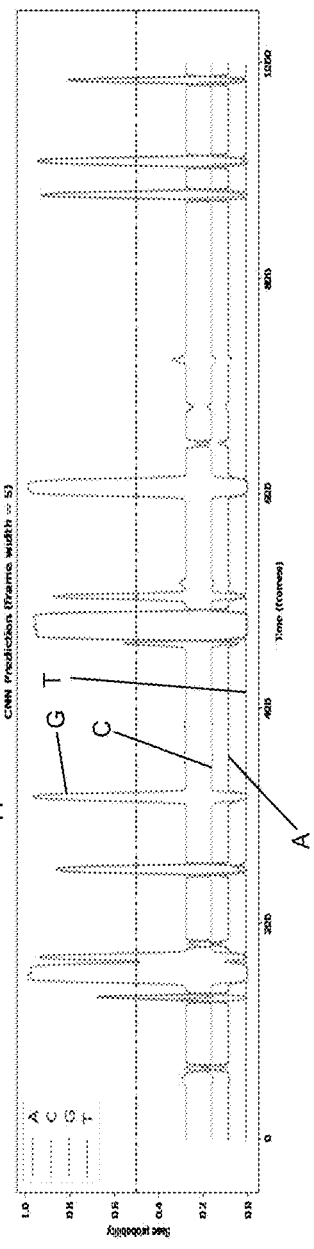

To further illustrate, FIG. 19 is a plot that shows a raw trace of time bin 1 and time bin 2 photon counts (e.g., as acquired from operation 1802). Then, with this data, FIGS. 20A-20C are plots that show running base count probabilities produced by inputting the raw trace data to a convolutional neural network applied over different-sized windows. In the specific examples illustrated, the plot of FIG. 20A uses a prediction frame width of 50 frames as discussed above. FIG. 20B uses a prediction frame width of 25, and FIG. 20C uses a prediction frame width of 5. From these examples, it will be noted that smaller windows actually produce cleaner probability peaks since it is less likely to confound the data by capturing more than one pulse in a single window. On the other hand, there is a trade off in that enough of a pulse needs to be captured in order to call the base accurately. As further shown in FIGS. 20A-20C, a simple thresholding at 50% probability (indicated by the dashed line) may be acceptable for base-calling use in that it produces an actual, alignable sequence, although the base-calling accuracy may be less than that achievable by the earlier described technique of pre-segmenting and identifying pulse calling traces from the raw sensor data. Alternatively, the peak-calling parameters in probability space may be tuned, with the tradeoff that it adds an extra step to the process (similar to a two-step pulse calling and base calling approach). Another advantage to performing pulse calling with convolution is that it allows the use of both time bin 1 and time bin 2 values separately to predict where pulses occur, rather than additive intensities across both bins, possibly leading to more accurate pulse calls, in addition to base calls.

Figure 21:
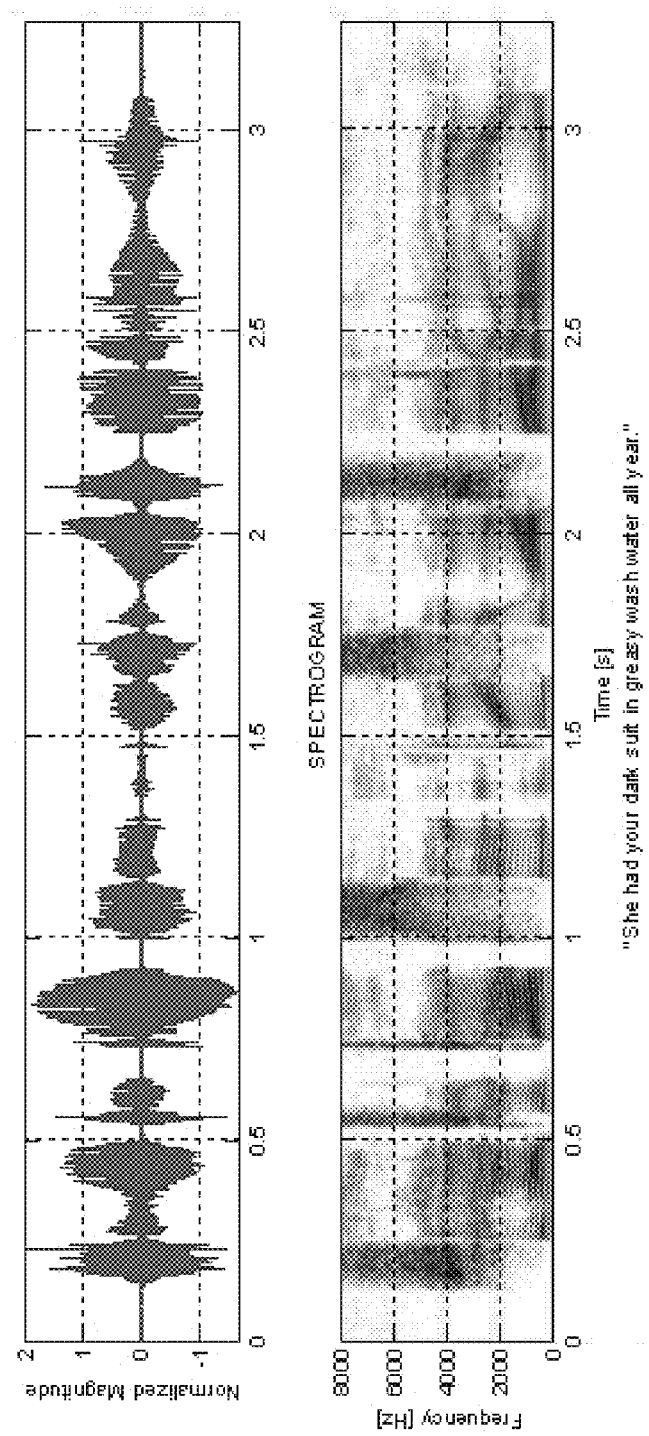
FIG. 21 illustrates a spectrogram plot and a normalized magnitude plot of the spectrogram plot, in accordance with some embodiments of the technology described herein.

Another possible approach to implementing a learning enabled base caller to directly call bases from a trace, without pre-segmenting pulses, utilizes models for speech recognition. Speech recognition is in many ways analogous to base-calling. For instance, connectionist temporal classification (CTC) models take as input snippets of speech (multidimensional wave-forms of indeterminate length) and labels as indeterminate lists of letters or phonemes. A special cost function allows the alignment/optimization of model output to these labels of unknown length. To illustrate this concept, FIG. 21 shows a pair of plots, with the lower plot being a spectrogram of the spoken phrase "She had your dark suit in greasy wash water all year" and the upper plot depicting a normalized magnitude of the spectrogram.

This is a very good analogy for a base calling problem, where it is desired for a network to learn a variable number of symbols (base calls) from waveforms of any length.

Further, the ability to feed an algorithm this type of data for training may relieve some of the problem of pre-aligning data to assign exact labels on a per-pulse basis, and instead assign labels on a per-window basis where it is reasonably certain that "anchor points" are established—meaning that base alignment to a reference sequence was good.

Figure 22:
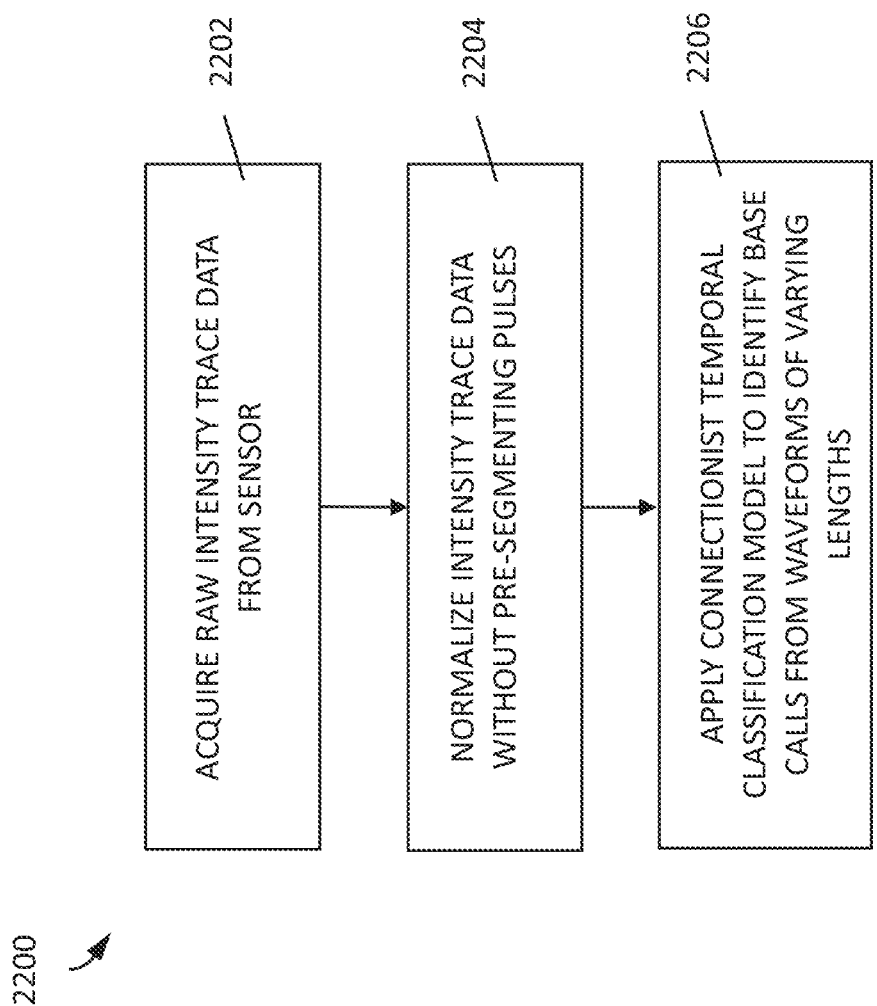
FIG. 22 is a flow diagram illustrating a method of implementing a learning enabled base caller, in accordance with some embodiments of the technology described herein.

In this regard, FIG. 22 is a flow diagram illustrating a method 2200 of implementing a learning enabled base caller, according to another embodiment. Similar to previous embodiments, method 2200 begins at operation 2202 by acquisition of raw intensity trace data from a sensor. Then in operation 2204, the intensity trace data is normalized without first being pre-segmented. The normalization process applied in operation 2204 may involve normalizing the intensity trace data such that the values in the data are within a range to account for variation between sequence runs and parameters used to obtain different sequence runs. A connectionist temporal classification model is then applied to the normalized intensity trace data to identify base calls from waveforms of varying lengths, as shown in operation 2206.

Figure 23:
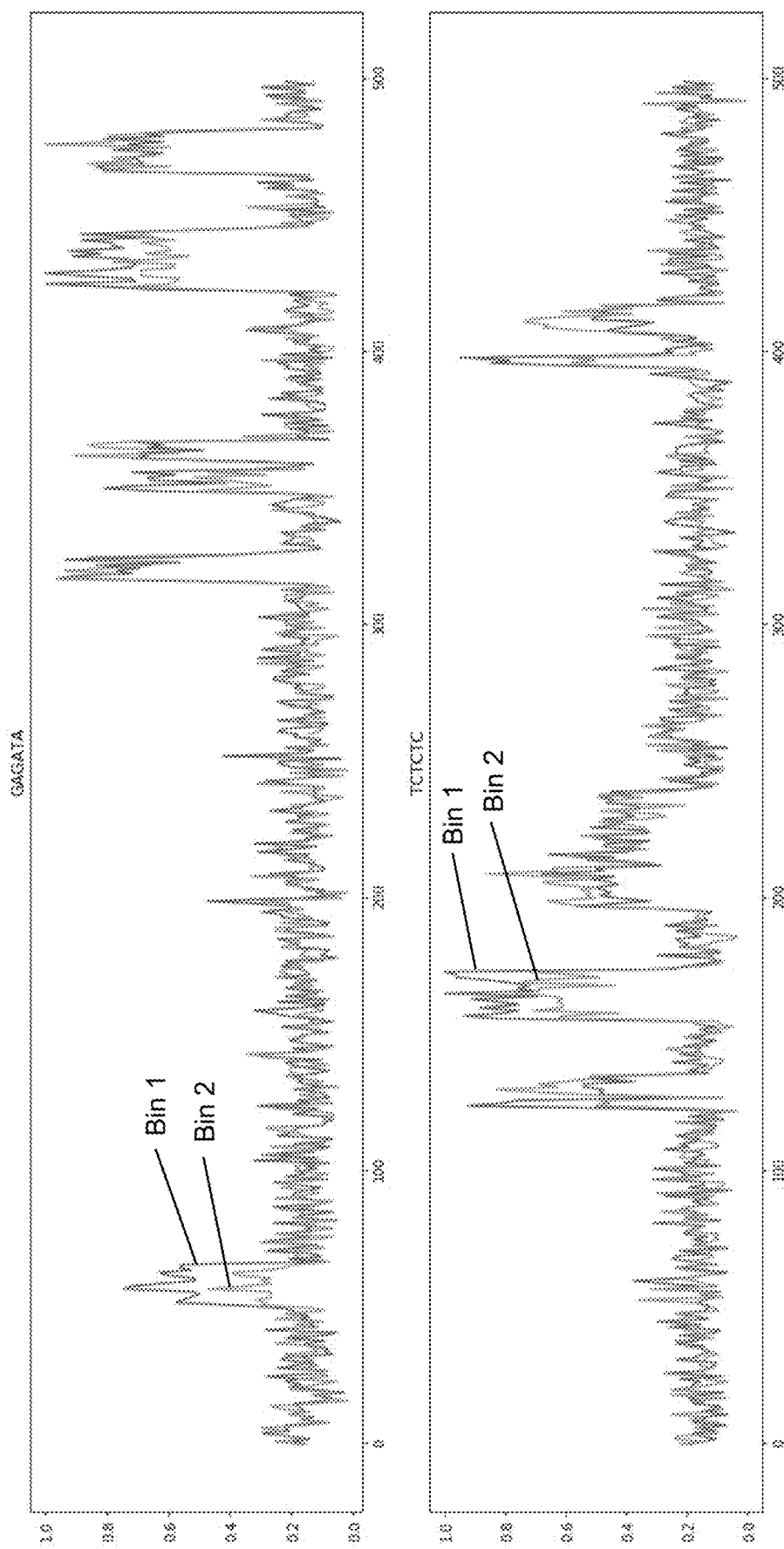
FIG. 23 illustrates a pair of single-photon avalanche diode (SPAM input data segments with associated base labels, in accordance with some embodiments of the technology described herein.
Figure 24:
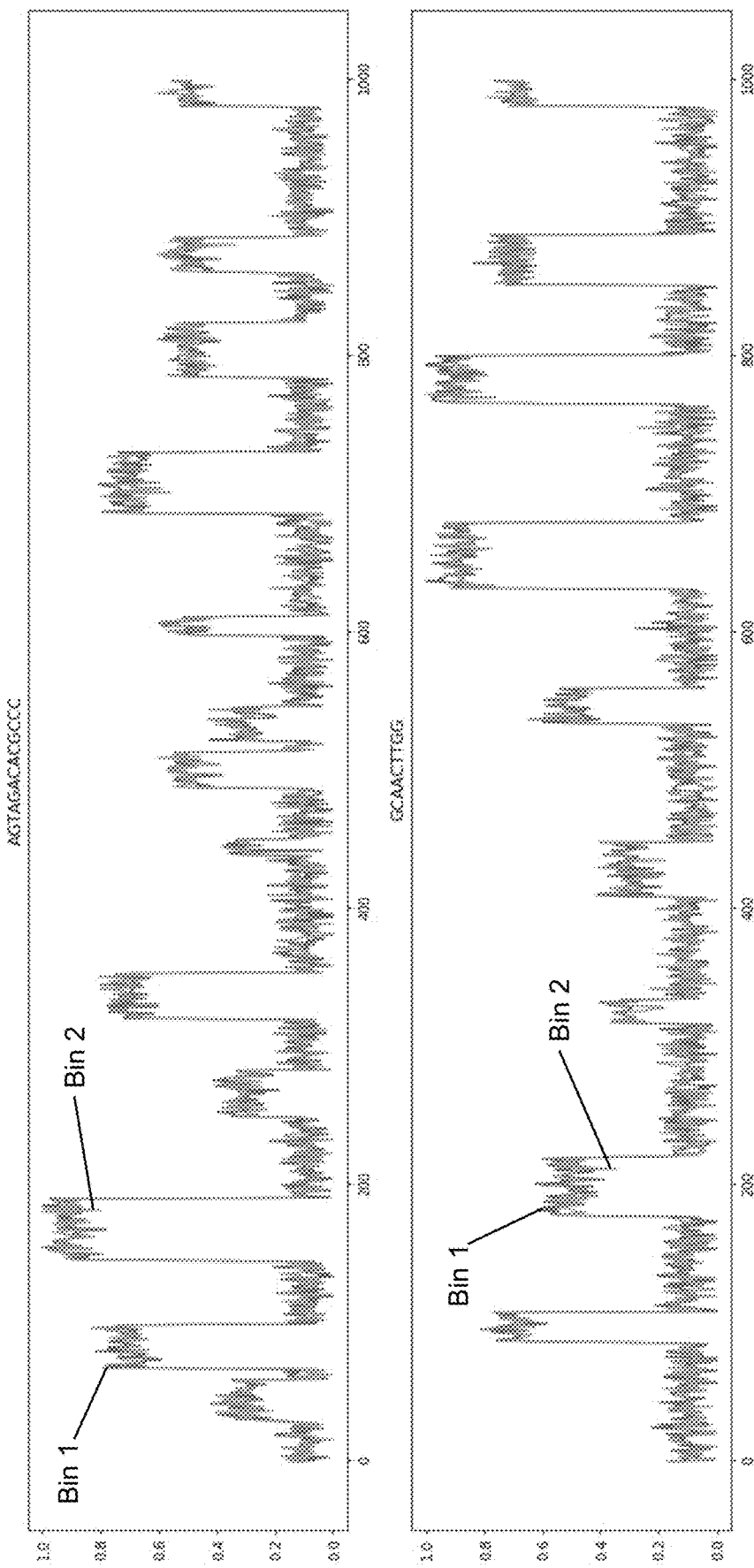
FIG. 24 illustrates a pair of simulated input data segments with associated base labels, in accordance with some embodiments of the technology described herein.

The inventors have successfully trained a model for base calling using segmented, single-photon avalanche diode (SPAD) input data for feeding such a model. FIG. 23 illustrates two such segments of SPAD input data with associated base labels. In addition, because CTC models can be very complex, it is also possible to simulate simplified data that, while not resembling real sequencing data, nonetheless matches all of the properties that matter for obtaining a preliminary solution using CTC. Here, a pair of exemplary simulated data segments is shown in FIG. 24. It will be noted that each base is simply assigned an intensity, with no difference between time bin 1 and time bin 2.

Figure 41:
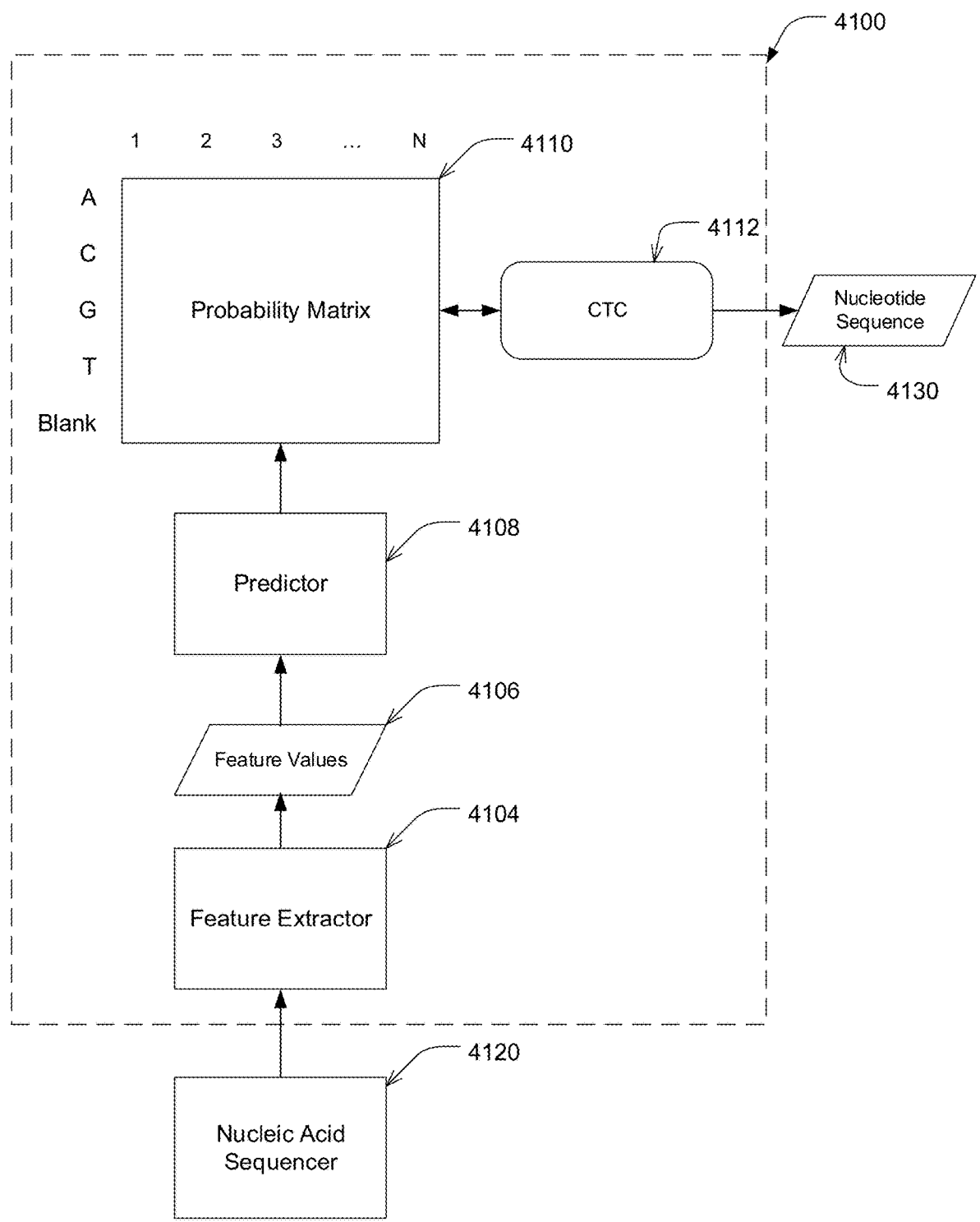
FIG. 41 is a block diagram of an exemplary connectionist temporal classification (CTC)-fitted model for identifying nucleotides of a nucleic acid, in accordance with some embodiments of the technology described herein.

FIG. 41 illustrates an example of a connectionist temporal classification (CTC)-fitted neural network model 4100 for identifying nucleotides of a nucleic acid, according to some embodiments of the technology described herein. In some embodiments, the CTC-fitted neural network model 4100 may be trained by performing process 3900 described above with reference to FIG. 39A. In some embodiments, the trained CTC-fitted neural network model 4100 obtained from process 3900 may be used to perform process 3910 described above with reference to FIG. 39B. In some embodiments, the CTC-fitted neural network model 4100 may be used in process 2200 described above with reference to FIG. 22.

In the example embodiment of FIG. 41, the model 4100 is configured to receive data from a nucleic acid sequencer 4120. For example, the sequencer 4120 may be sequencing system 300 described above with reference to FIG. 3. In some embodiments, the model 4100 may be configured to receive data generated by the sequencer 4120. The data may be accessed from detected light emissions by luminescent labels associated with nucleotides during incorporation of nucleotides for the nucleic acid. In some embodiments, the data may be arranged as multiple series of numbers of photons and/or frames as described above with reference to FIG. 38B. In some embodiments, portions of the data obtained from the sequencer 4120 may be provided as a series of inputs to the model 4100. For example, the model 4100 may be configured to receive a first 2×400 input specifying numbers of photons detected in two time intervals after each of 400 light pulses.

In the example embodiment of FIG. 41, the model 4100 includes a feature extractor 4104. In some embodiments, the feature extractor may be an encoder of a trained autoencoder. The autoencoder may be trained, and the decoder from the autoencoder may be implemented as the feature extractor 4104. The encoder may be configured to encode the input as values of one or more features 4106.

In the example embodiment of FIG. 41, the feature values 4106 determined by the feature extractor 4104 are input into a predictor 4108 which outputs a probability matrix 4110 indicating a series of probability values for each possible class. In the example embodiment of FIG. 41, the classes include nucleotides that can be incorporated into a nucleic acid (e.g., Adenine (A), Cytosine (C), Guanine (G), and Thymine (T), and blank (-)). As an example, the predictor 4108 may output a 5×50 matrix indicating a series of 50 probability values for each of the classes. The probability matrix 4110 may be used to generate an output 4130 identifying a sequence of nucleotides corresponding to data received from the nucleic acid sequencer 4120. In some embodiments, the sequence of nucleotides may be determined from the probability matrix 4110. For example, a beam search may be performed to obtain the output 4130 of nucleotides.

In some embodiments, the feature extractor 4104 may be trained separately from the predictor 4108. For example, the feature extractor 4104 may be obtained by training an autoencoder. The encoder from the autoencoder may then be used as the feature extractor 4104. In some embodiments, the predictor 4108 may be separately trained using the CTC loss function 4112. The CTC loss function 4112 may train the predictor 4108 to generate an output that can be used to generate the output 4130.

In some embodiments, multiple probability matrices may be combined. A second input may be accessed from data obtained from the sequencer 4120. The second input may be a second portion of the data obtained from the sequencer 4120. In some embodiments, the second input may be obtained by shifting by a number of points in the data obtained from the sequencer 4120. For example, the second input may be a second 400×2 input matrix obtained by shifting 8 points in the data obtained from the sequencer 420. A probability matrix corresponding to the second input may be obtained from the predictor 4108, and combined with a first probability matrix corresponding to a first input. For example, the second probability matrix may be added to the first probability matrix. As another example, the second probability matrix may be shifted and added to the first probability matrix. The combined probability matrices may then be used to obtain the output 4130 identifying a sequence of nucleotides of a nucleic acid.

In some embodiments, the feature extractor 4104 may be a neural network. In some embodiments, the neural network may be a convolutional neural network (CNN). In some embodiments, the CNN may include one or more convolutional layers and one or more pooling layers. The CNN may include a first convolutional layer in which the input from the sequencer 4120 is convolved with a set of filters. For example, the input may be convolved with a set of 16 10×2 filters using a stride of 1×1 to generate a 16×400×2 output. An activation function may be applied to the output of the first convolutional layer. For example, an ReLU activation function may be applied to the output of the first convolutional layer. In some embodiments, the CNN may include a first pooling layer after the first convolutional layer. In some embodiments, the CNN may apply a maxpool operation on the output of the first convolutional layer. For example, a 2×2 filter with a 1×1 stride may be applied to a 16×400×2 output to obtain a 200×1 output.

In some embodiments, the CNN may include a second convolutional layer. The second convolutional layer may receive the output of the first pooling layer as an input. For example, the second convolutional layer may receive the 200×1 output of the first pooling layer as input. The second convolutional layer may involve convolution with a second set of filters. For example, in the second convolutional layer, the 200×1 input may be convolved with a second set of 16 10×1 filters with a stride of 1×1 to generate a 16×200 output. An activation function may be applied to the output of the second convolutional layer. For example, an ReLU activation function may be applied to the output of the second convolutional layer. In some embodiments, the CNN may include a second pooling layer after the second convolutional layer. In some embodiments, the CNN may apply a maxpool operation on the output of the second convolution layer. For example, a 4×1 filter with a 4×1 stride may be applied to the 16×200 output of the second convolutional layer to obtain a 16×50 output.

In some embodiments, the feature extractor 4104 may be a recurrent neural network (RNN). For example, the feature extractor 4104 may be an RNN trained to encode data received from the sequencer 4120 as values of one or more features. In some embodiments, the feature extractor 4104 may be a long short-term memory (LSTM) network. In some embodiments, the feature extractor 4104 may be a gated recurrent unit (GRU) network.

In some embodiments, the predictor 4108 may be a neural network. In some embodiments the neural network may be a GRU network. In some embodiments, the GRU network may be bidirectional. As an example, the GRU network may receive the 16×50 output of the feature extractor 4104 which is provided as input to the GRU network. For example, the GRU network may have 64 hidden layers that generate a 50×128 output. In some embodiments, GRU network may use a tan h activation function. In some embodiments, predictor 4108 may include a fully connected layer. The output of the GRU network may be provided as input to the fully connected layer which generates a 5×50 output matrix. The 5×50 matrix may include a series of values for each possible output class. In some embodiments, the predictor 4108 may be configured to apply a softmax function on the output of the fully connected layer to obtain the probability matrix 4110.

There are potentially several benefits of a simulated dataset (whether simulated from real two-bin SPAD data or integrated chip data), including for example: (1) by helping to understand error modes, and components of the raw data produce such components "from the ground-up"; (2) the potential for unlimited data that can be used to create novel deep learning architectures; (3) the ability to train deep learning models with very simple data at the outset (e.g., high SNR, no artifacts), and then titrate in simulated sequencing errors and noise to gauge how a model may or may not be suited toward detecting specific types of signal artifacts; and (4) the potential to pre-train some deep learning models on simulated data, and thereafter train on real data to fine-tune the network weights. It should be appreciated, however, that simulated data is merely a tool and stand-in for exploring models and the capability to handle large and error-rich data prior to the availability of real data in quantity.

FIGS. 25-34 illustrate, in further detail, embodiments for producing a simulated trace. With specific reference to FIG. 25, a 400-frame segment of a real trace is illustrated, where it is desired to be able to produce something of a similar character (although not necessary having the exact base incorporations). To produce simulated data, distributions that describe various signal characteristics may be used and, for example, may be fit from real SPAD data. FIG. 26 and FIG. 27 are, respectively, examples of fitted distributions on background-subtracted time-bin ratio, and base intensity (as a ratio above baseline). As can be seen in the plot of FIG. 28, intersecting these two distributions provides better distinction between the four bases. However, there may be some overlap between A and C given a certain level of SNR.

Figure 29:
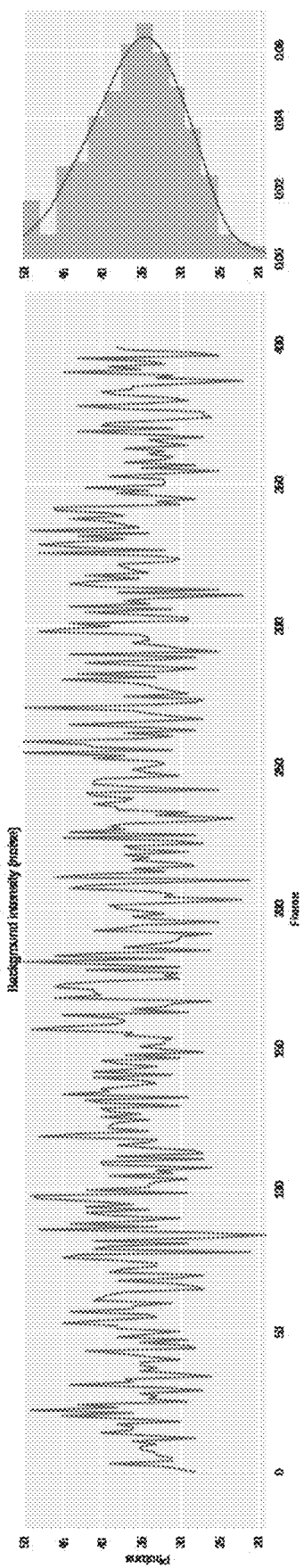
FIG. 29 is an exemplary plot of system noise over a 400-frame segment, in accordance with some embodiments of the technology described herein.
Figure 30:
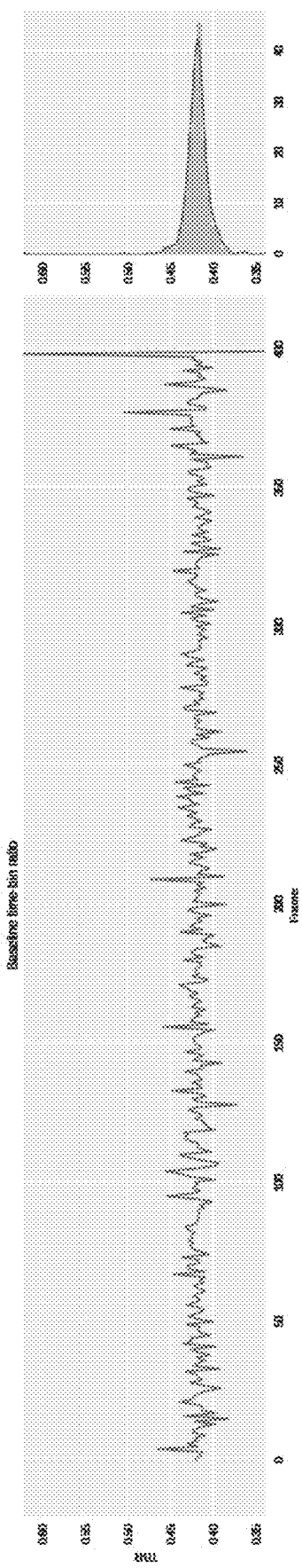
FIG. 30 is an exemplary plot that simulates time-bin ratio across the length of the 400-frame trace, in accordance with some embodiments of the technology described herein.
Figure 31:
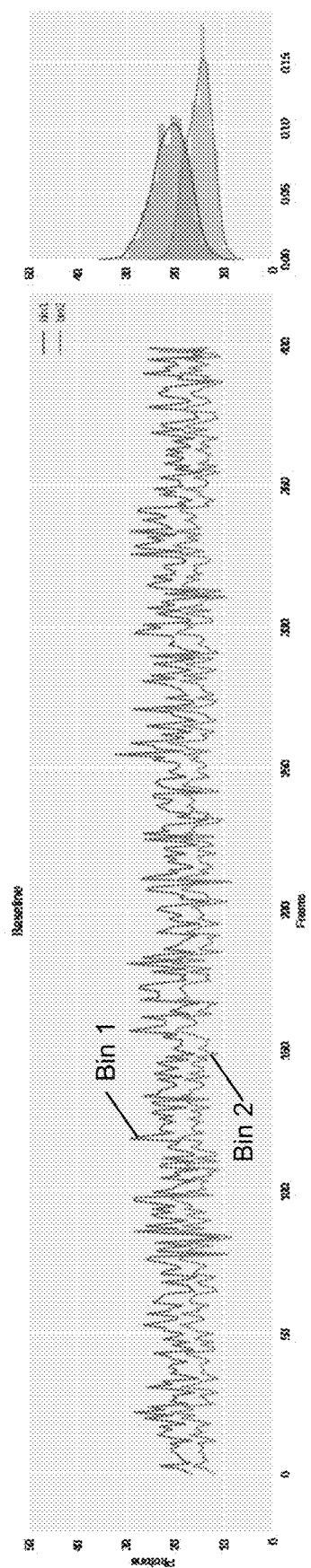
FIG. 31 is an exemplary plot that splits the system noise into bin 1 and bin 2 components, using the plots in FIG. 29 and FIG. 30, in accordance with some embodiments of the technology described herein.

Using these and other distributions, a trace may be constructed by layering on elements of a signal. Initially, system noise (also known as Poisson noise) is taken into account, which represents the photons that get read by the device sensor regardless of whether there is a base incorporation event. An exemplary plot of system noise over a 400-frame segment is illustrated in FIG. 29. In addition, the system noise with respect to time-bin ratio is taken into account. That is, background noise photons get split by the detecting circuit into bin 1 and bin 2, just as the photons from the incorporation signals do. However, there are no specific dye characteristics that guide the binning of noise photons. Thus, one approach is to fit a distribution to time-bin ratio (bin 2/(bin 1+bin 2)) outside of pulse events, and randomly draw from this distribution to simulate time-bin ratio across the length of the trace. An exemplary plot of this time-binning of system noise over a 400-frame segment is illustrated in FIG. 30. Given the intensity of the noise in the plot of FIG. 29 and the time bin ratio in the plot of FIG. 30, the system noise may then be split into its bin 1 and bin 2 components, as shown in the plot of FIG. 31.

Figure 32:
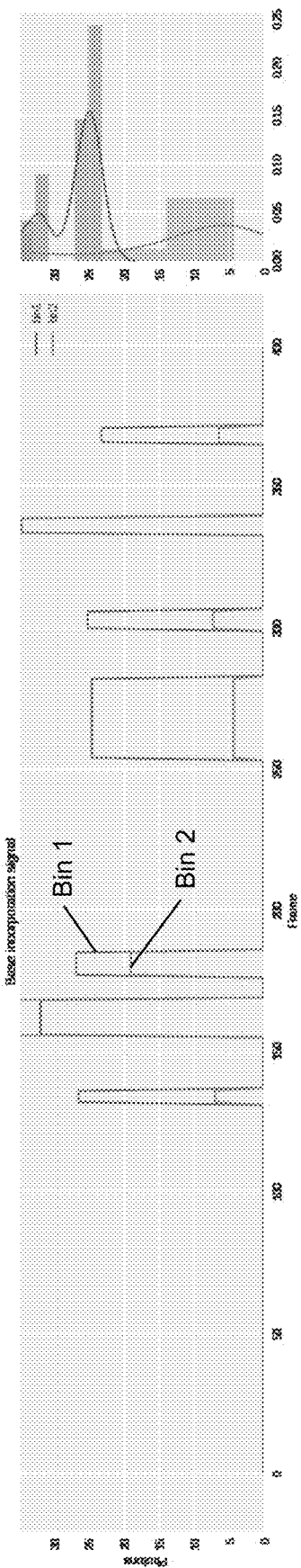
FIG. 32 is an exemplary plot of a clean base incorporation signal randomly placed on the 400-frame trace, in accordance with some embodiments of the technology described herein.
Figure 33:
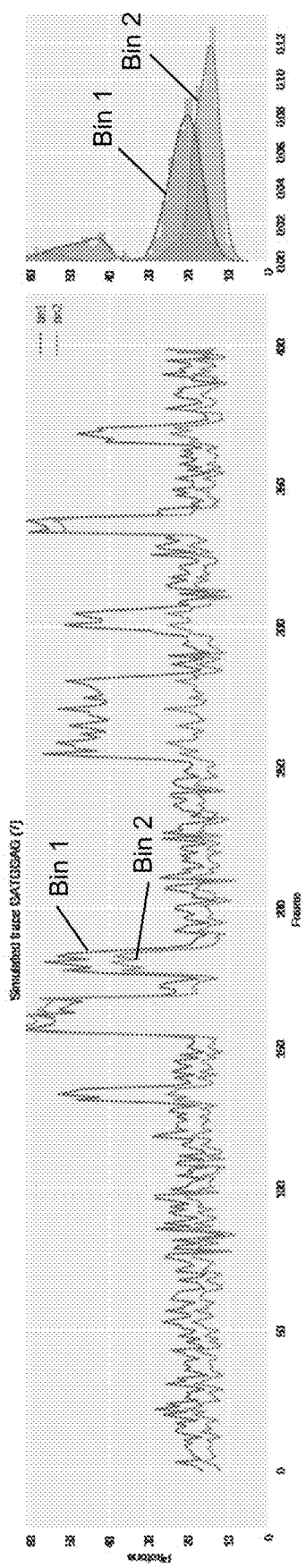
FIG. 33 is an exemplary plot of a simulated trace generated by adding the random clean signal trace of FIG. 32 to the baseline noise plot of FIG. 31, in accordance with some embodiments of the technology described herein.

In the absence of noise, each base incorporation should ideally produce essentially a square-wave signal. For a simulated trace, a random starting place on a given template, and generate the base calls. Then, durations and time-bin ratios of pulses, as well as inter-pulse durations may be simulated based on fitted distributions to real data. FIG. 32 illustrates an example plot of a clean base incorporation signal randomly placed on the 400-frame trace. In a real system, there will be both noise and signal simultaneously, with photons from each being additive in each bin. Therefore, a "clean" trace, without other artifacts besides baseline noise, will be a simple addition of signal and noise traces. FIG. 33 illustrates an example simulated trace generated by adding the random clean signal trace of FIG. 32 to the baseline noise plot of FIG. 31.

Figure 34:
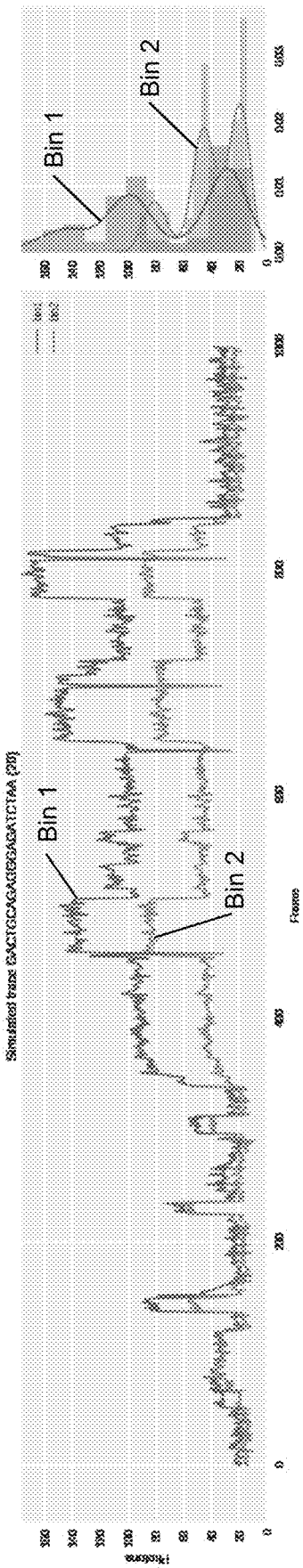
FIG. 34 is an exemplary plot of a simulated trace with artifacts applied to exaggerated levels, in accordance with some embodiments of the technology described herein.

Compared to the real data trace of FIG. 25, the simulated data trace of FIG. 33 compares favorably, and may be beneficial for model building purposes when clean data is required. On the other hand, it is also desirable to be able to learn in the presence of certain sequencing artifacts. Examples of such artifacts that may be simulated include, but are not necessarily limited to: dark dies (leading to missing or half-intensity pulses); fused pulses (no return to baseline between pulses); flickering pulses (pulse is interrupted midway and thereafter resumed); baseline jumps (e.g., due to dye sticking); laser drift (gradual baseline increase/decrease). Some of these artifacts may be additive (e.g., baseline jumps), while others may be multiplicative (e.g., laser drift). To further illustrate, FIG. 34 shows another segment of a simulated trace with each the above artifacts applied to exaggerated levels. However, it is likely more practical to only add one or two artifacts at a time to test a model's ability to operate in a regime of predictable artifacts.

As indicated above, one advantage of training a deep learning model that is optimized using the CTC loss function is the ability to eliminate the pulse calling step and predict bases directly from raw traces. Moreover, such a paradigm allows for the input and output size of the model to vary, which in turn allows for feeding the algorithm examples of windows of traces and corresponding windows of bases. In turn, feeding windows of bases improves labeling accuracy. Furthermore, after a model is exposed to several such examples of windows of traces and corresponding windows of bases, the model will learn how to call pulses and bases by optimizing on pulse and base calling at the same time. That is, a model may take properties of bases into account when it determines whether to call a pulse, in addition to properties of pulses into account when it calls a base. By tying this approach together into a single step, the algorithm has the ability to simply find As, Ts, Cs, and Gs directly in the signal, without the need to pulse call. One type of property of a base that may be used in deciding to call a pulse may include a time-bin photon count ratio. For example, if a potential pulse has a time bin photon count ratio similar to a time bin photon count ratio observed for a particular base (e.g., A, C, T, G), then the potential pulse may be identified by the model as being the particular base. However, if the potential pulse differs from or does not match a time bin photon count ration observed for a particular base, then the model may reject the potential pulse.

Figure 35:
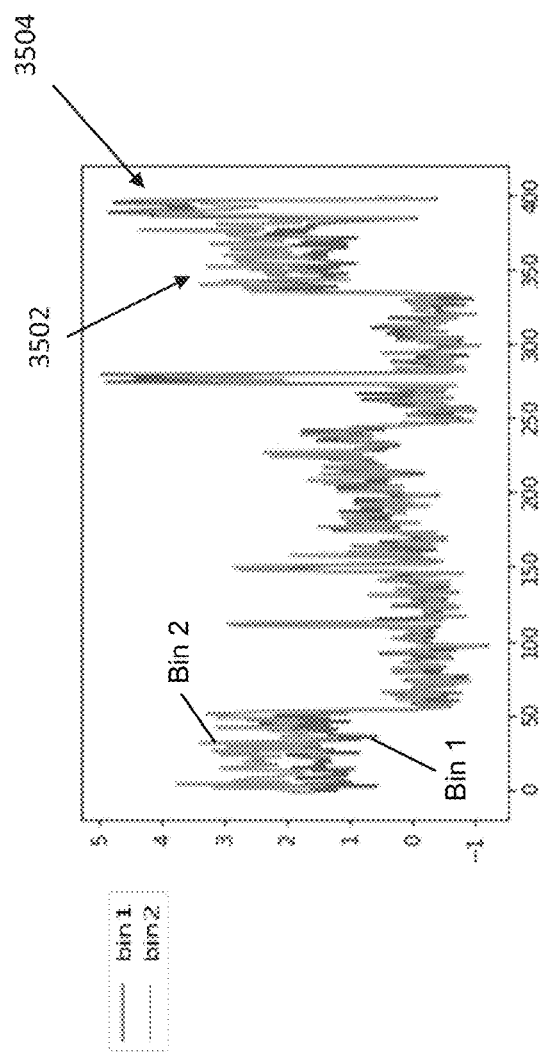
FIG. 35 is a plot that shows an example of raw trace of time bin 1 and time bin 2 photon counts that appears to depict a fused pulse, in accordance with some embodiments of the technology described herein.
Figure 36:
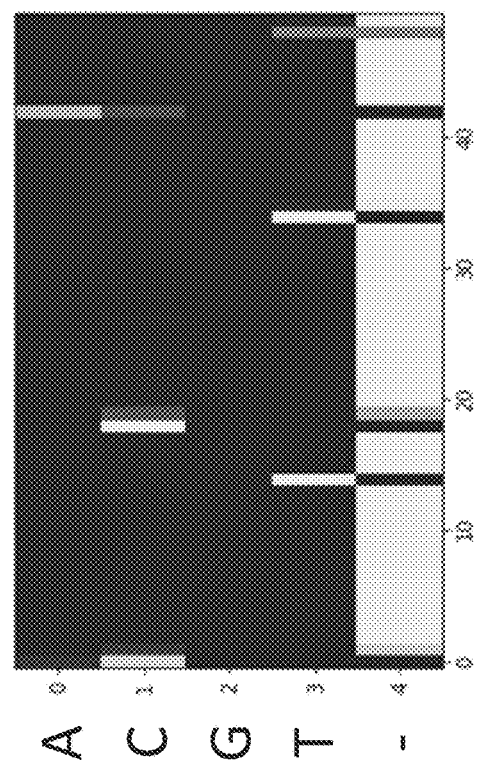
FIG. 36 is a probability distribution used to call bases directly from the FIG. 35 data using the CTC-based model of FIG. 22, in accordance with some embodiments of the technology described herein.

Still a further advantage of an all-in-one pulse/base-caller is that the model may more readily distinguish cases that may be difficult for a two-step pulse and base caller. For example, FIG. 35 illustrates raw sensor trace data having "fused" pulses, and FIG. 36 is a corresponding probability distribution (where 0=A, 1=C, 2=G, 3=T, and 4=no base) for calling bases directly from the FIG. 35 data using the CTC-based model. As will be noted from FIG. 35, that the last two pulses 3502, 3504, appear to be fused together, a case that would be difficult for a stand-alone pulse caller to handle (e.g., it may call the entire event as a single pulse). However, because the two individual pulses 3502, 3504 of this seemingly fused pulse have quite different time bin 1 and time bin 2 characteristics (time bin 1 is lower in the first pulse 3502 and higher in the second pulse 3504), the all-in-one pulse/base caller can distinguish this as two separate pulses (e.g., as two spikes in the probability distribution of FIG. 36 at different bases). Therefore, the model uses properties of bases to call pulses.

Figure 37:
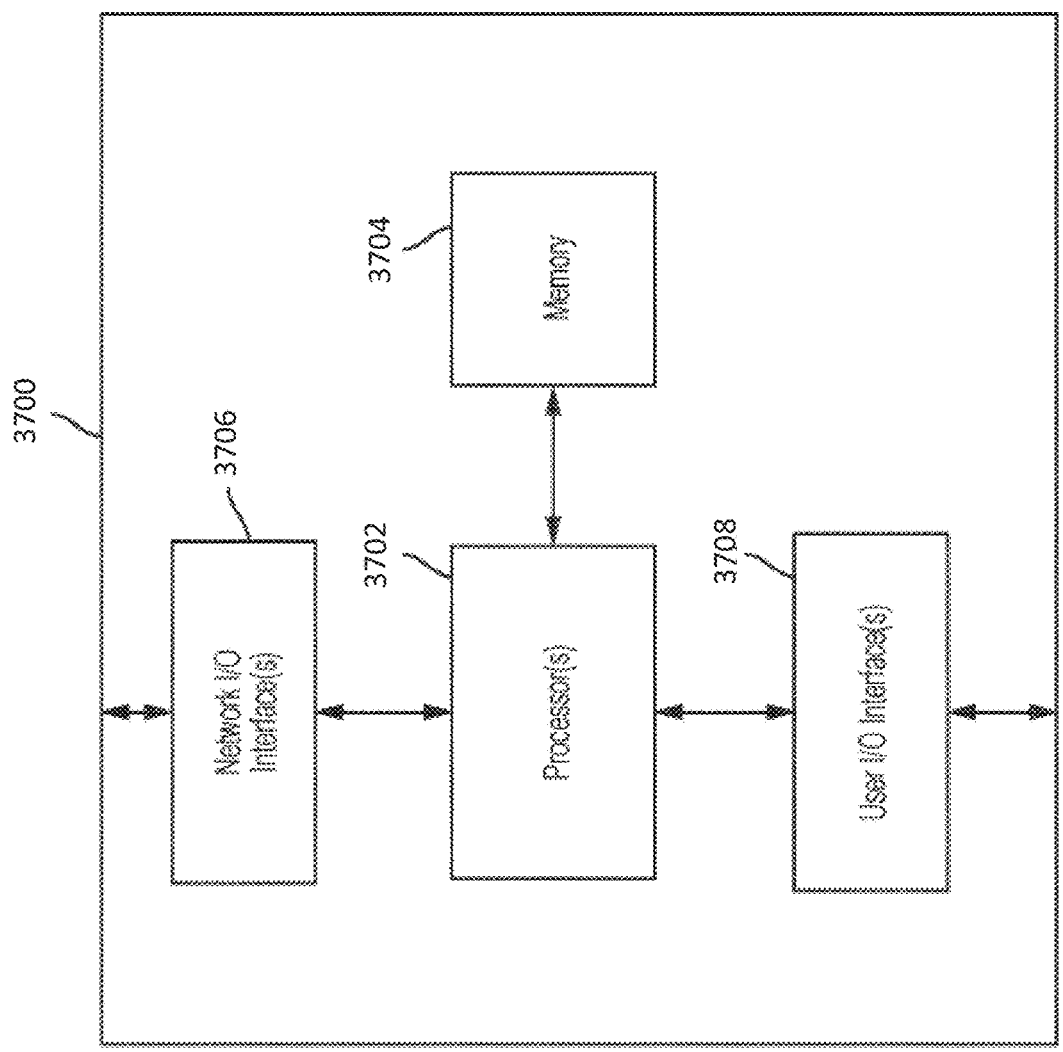
FIG. 37 is a block diagram of an illustrative computing device that may be used in implementing some embodiments of the technology described herein.

In some embodiments, techniques described herein may be carried out using one or more computing devices. Embodiments are not, however, limited to operating with any particular type of computing device. By way of further illustration, FIG. 37 is a block diagram of an illustrative computing device 3700. Computing device 3700 may include one or more processors 3702 and one or more tangible, non-transitory computer-readable storage media (e.g., memory 3704). Memory 3704 may store, in a tangible non-transitory computer-recordable medium, computer program instructions that, when executed, implement any of the above-described functionality. Processor(s) 3702 may be coupled to memory 3704 and may execute such computer program instructions to cause the functionality to be realized and performed.

Computing device 3700 may also include a network input/output (I/O) interface 3706 via which the computing device may communicate with other computing devices (e.g., over a network), and may also include one or more user I/O interfaces 3708, via which the computing device may provide output to and receive input from a user. The user I/O interfaces may include devices such as a keyboard, a mouse, a microphone, a display device (e.g., a monitor or touch screen), speakers, a camera, and/or various other types of I/O devices.

The above-described embodiments can be implemented in any of numerous ways. For example, the embodiments may be implemented using hardware, software or a combination thereof. When implemented in software, the software code can be executed on any suitable processor (e.g., a microprocessor) or collection of processors, whether provided in a single computing device or distributed among multiple computing devices. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of the embodiments described herein comprises at least one computer-readable storage medium (e.g., RAM, ROM, EEPROM, flash memory or other memory technology, CD-ROM, digital versatile disks (DVD) or other optical disk storage, magnetic cassettes, magnetic tape, magnetic disk storage or other magnetic storage devices, or other tangible, non-transitory computer-readable storage medium) encoded with a computer program (i.e., a plurality of executable instructions) that, when executed on one or more processors, performs the above-discussed functions of one or more embodiments. The computer-readable medium may be transportable such that the program stored thereon can be loaded onto any computing device to implement aspects of the techniques discussed herein. In addition, it should be appreciated that the reference to a computer program which, when executed, performs any of the above-discussed functions, is not limited to an application program running on a host computer. Rather, the terms computer program and software are used herein in a generic sense to reference any type of computer code (e.g., application software, firmware, microcode, or any other form of computer instruction) that can be employed to program one or more processors to implement aspects of the techniques discussed herein.

Various aspects of the technology described herein may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the technology described herein may be embodied as a method, of which examples have been provided as described above including with reference to FIGS. 2, 11, 15, 18, 22, and 39A-B. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

What is claimed is:

1. A method for identifying nucleotides of a nucleic acid, the method comprising:
   using at least one computer hardware processor to perform:
      accessing data obtained from detected light emissions by luminescent labels associated with nucleotides during nucleotide incorporation events for the nucleic acid, wherein the light emissions are responsive to a series of light pulses and the data includes numbers of photons detected after each of at least some of the light pulses; and
      providing the data as input to a trained deep learning model to obtain output identifying nucleotides of the nucleic acid, wherein providing the data as input to the trained deep learning model comprises arranging the data into a data structure having columns, wherein:
         a first column holds a number of photons in each of a first and second time interval in a first time period after a first light pulse in the series of light pulses; and
         a second column holds a number of photons in each of a first and second time interval in a second time period after a second light pulse in the series of light pulses.

2. The method of claim 1, wherein the deep learning model comprises a convolutional neural network.

3. The method of claim 1, wherein the deep learning model comprises a connectionist temporal classification (CTC)-fitted neural network model.

4. The method of claim 1, wherein the output identifying nucleotides of the nucleic acid comprises, for each of a plurality of nucleotides, a respective time series of values indicating probabilities that the nucleotide was incorporated into the nucleic acid.

5. The method of claim 1, further comprising:
   wherein the output identifying nucleotides of the nucleic acid comprises, for each of a plurality of nucleotides, a probability that the nucleotide was incorporated into the nucleic acid; and
   the method further comprises identifying a first one of the plurality of nucleotides in the nucleic acid when the probability that the first nucleotide was incorporated into the nucleic acid exceeds a threshold probability.

6. The method of claim 1, wherein providing the data as input to the trained deep learning model comprises:
   organizing the data into a plurality of time periods including the first time period and the second time period; and
   providing data for each of the plurality of time periods as an input to the trained deep learning model to obtain a corresponding output indicating at least one nucleotide of the nucleic acid.

7. The method of claim 6, wherein an output corresponding to a respective time period provided as input to the trained deep learning model indicates, for each of a plurality nucleotides, a value indicating a probability that the nucleotide was incorporated into the nucleic acid in the time period.

8. The method of claim 1, wherein providing the data as input to the trained deep learning model comprises:
   identifying a plurality of portions of the data, each portion corresponding to a respective one of the nucleotide incorporation events; and
   providing each of the plurality of portions of the data as an input to the trained deep learning model to obtain an output corresponding to the portion of the data.

9. The method of claim 8, wherein the output corresponding to the portion of the data identifies a nucleotide that was incorporated into the nucleic acid.

10. The method of claim 1, further comprising:
    accessing training data obtained from detected light emissions by luminescent labels associated with nucleotides during nucleotide incorporation events for a plurality of nucleic acids; and
    training a deep learning model using the training data and information specifying at least some of the nucleotides in the plurality of nucleic acids to obtain the trained deep learning model.

11. The method of claim 1, wherein the data includes, for each of at least some of the light pulses, a respective number of photons detected in each of a plurality of intervals of a time period after the light pulse.

12. A system for identifying nucleotides of a nucleic acid, the system comprising:
    at least computer hardware processor; and
    at least one non-transitory computer-readable storage medium storing instructions that, when executed by the at least one computer hardware processor, cause the at least one computer hardware processor to perform:
       accessing data obtained from detected light emissions by luminescent labels associated with nucleotides during nucleotide incorporation events for the nucleic acid, wherein the light emissions are responsive to a series of light pulses and the data includes numbers of photons detected after each of at least some of the light pulses; and
       providing the data as input to a trained deep learning model to obtain output identifying nucleotides of the nucleic acid, wherein providing the data as input to the trained deep learning model comprises arranging the data into a data structure having columns, wherein:
          a first column holds a number of photons in each of a first and second time interval in a first time period after a first light pulse in the series of light pulses; and
          a second column holds a number of photons in each of a first and second time interval in a second time period after a second light pulse in the series of light pulses.

13. At least one non-transitory computer-readable storage medium storing instructions that, when executed by at least one computer hardware processor, cause the at least one computer hardware processor to perform:
    accessing data obtained from detected light emissions by luminescent labels associated with nucleotides during nucleotide incorporation events for the nucleic acid, wherein the light emissions are responsive to a series of light pulses and the data includes numbers of photons detected after each of at least some of the light pulses; and providing the data as input to a trained deep learning model to obtain output identifying nucleotides of the nucleic acid, wherein providing the data as input to the trained deep learning model comprises arranging the data into a data structure having columns, wherein:
- a first column holds a number of photons in each of a first and second time interval in a first time period after a first light pulse in the series of light pulses; and
- a second column holds a number of photons in each of a first and second time interval in a second time period after a second light pulse in the series of light pulses.

14. A method for identifying nucleotides of a nucleic acid, the method comprising:

using at least one computer hardware processor to perform:
- accessing data obtained from detected light emissions by luminescent labels associated with nucleotides, the light emissions responsive to a series of light pulses, the data including, for each of at least some of the light pulses, a respective number of photons detected in each of a plurality of intervals in a time period after the light pulse; and
- providing the data as input to a trained machine learning model to obtain output identifying nucleotides of the nucleic acid, wherein providing the data as input to the trained machine learning model comprises arranging the data into a data structure having columns, wherein:
  - a first column holds a number of photons in each of a first and second time interval in a first time period after a first light pulse in the series of light pulses; and
  - a second column holds a number of photons in each of a first and second time interval in a second time period after a second light pulse in the series of light pulses.

15. The method of claim 14, wherein the data includes data indicating a respective number of photons in each of the first and second time interval in the first time period after the first light pulse in the series of light pulses.

16. The method of claim 15, wherein the data further includes a respective number of photons in each of the first and second time interval in the second time period after the second light pulse in the series of light pulses.

17. The method of claim 14, wherein providing the data as input to the trained machine learning model comprises arranging the data in an image, wherein each pixel of the image specifies a number of photons detected in an interval of a time period after one of the at least some pulses.

18. The method of claim 14, wherein providing the data as input to the trained machine learning model comprises arranging the data into a data structure having rows wherein each of the rows holds numbers of photons in a respective interval corresponding to the at least some light pulses.

19. The method of claim 14, wherein providing the data as input to the trained machine learning model comprises:
- identifying a plurality of portions of the data, each portion corresponding to a respective one of the nucleotides of the nucleic acid; and
- providing each of the plurality of portions of the data as an input to the trained machine learning model to obtain an output corresponding to the portion of the data.

20. The method of claim 19, wherein identifying a portion of the data as corresponding to a respective nucleotide of the nucleic acid comprises:
- comparing a number of photons in a particular one of the plurality of intervals in the portion of data to a number of photons in at least one of the plurality of intervals separate from the particular interval in the portion of data.

21. The method of claim 14, wherein the machine learning model comprises a deep learning model.

22. The method of claim 21, wherein the deep learning model comprises a convolutional neural network.

23. The method of claim 22, wherein the machine learning model comprises a connectionist temporal classification (CTC)-fitted neural network model.

24. The method of claim 14, further comprising:
- accessing training data obtained from detected light emissions by luminescent labels associated with nucleotides during nucleotide incorporation events for a plurality of nucleic acids; and
- training a machine learning model using the training data and information specifying at least some of the nucleotides in the plurality of nucleic acids to obtain the trained machine learning model.

* * * * *